US008187601B2

(12) United States Patent
Weng et al.

(10) Patent No.: US 8,187,601 B2
(45) Date of Patent: May 29, 2012

(54) FIBROBLAST GROWTH FACTOR RECEPTOR 3 (FGFR3) BINDING PROTEINS

(75) Inventors: Zhigang Weng, Brookline, MA (US); William M. Winston, Jr., Marlborough, MA (US); Lyne Breault, Roslindale, MA (US); Kristan Meetze, Walpole, MA (US); Solly Weiler, Newton, MA (US); Jeno Gyuris, Lincoln, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 284 days.

(21) Appl. No.: 12/494,965

(22) Filed: Jun. 30, 2009

(65) Prior Publication Data

US 2010/0003258 A1 Jan. 7, 2010

Related U.S. Application Data

(60) Provisional application No. 61/077,278, filed on Jul. 1, 2008.

(51) Int. Cl.
C07K 16/28 (2006.01)

(52) U.S. Cl. .................. 424/139.1; 530/387.9

(58) Field of Classification Search ............ 424/139.1; 530/387.9
See application file for complete search history.

(56) References Cited

U.S. PATENT DOCUMENTS

| 5,707,632 | A | 1/1998 | Williams et al. |
|---|---|---|---|
| 7,288,637 | B2 | 10/2007 | Solomon et al. |
| 7,319,139 | B2 | 1/2008 | Braslawsky et al. |
| 7,498,416 | B2 | 3/2009 | Yayon et al. |
| 2001/0029293 | A1 | 10/2001 | Gallatin et al. |
| 2002/0098189 | A1 | 7/2002 | Young et al. |
| 2002/0111302 | A1 | 8/2002 | Tang et al. |
| 2003/0077793 | A1 | 4/2003 | Landry |
| 2003/0152571 | A1 | 8/2003 | Jonak et al. |
| 2003/0206912 | A1 | 11/2003 | Yayon et al. |
| 2003/0211106 | A1 | 11/2003 | Tornetta et al. |
| 2004/0005643 | A1 | 1/2004 | De Santis et al. |
| 2004/0034888 | A1 | 2/2004 | Liu et al. |
| 2004/0038339 | A1 | 2/2004 | Kufer et al. |
| 2004/0043930 | A1 | 3/2004 | Anderson et al. |
| 2004/0044187 | A1 | 3/2004 | Sato et al. |
| 2004/0052783 | A1 | 3/2004 | Weiner et al. |
| 2004/0116330 | A1 | 6/2004 | Naito et al. |
| 2004/0175744 | A1 | 9/2004 | Hu et al. |
| 2004/0253606 | A1 | 12/2004 | Aziz et al. |
| 2005/0153878 | A1 | 7/2005 | Bange et al. |
| 2005/0208042 | A1 | 9/2005 | Co et al. |
| 2006/0030015 | A1 | 2/2006 | Uda et al. |
| 2006/0194265 | A1 | 8/2006 | Morris et al. |
| 2006/0263369 | A1 | 11/2006 | Bicknell et al. |
| 2006/0281130 | A1 | 12/2006 | Bock et al. |
| 2007/0025992 | A1 | 2/2007 | Takayama et al. |
| 2007/0059306 | A1 | 3/2007 | Grosmaire et al. |
| 2007/0092878 | A1 | 4/2007 | Martinez et al. |
| 2007/0148191 | A1 | 6/2007 | Krenn et al. |
| 2007/0178095 | A1 | 8/2007 | Smith et al. |
| 2007/0178102 | A1 | 8/2007 | Yarden et al. |
| 2007/0237770 | A1 | 10/2007 | Lai et al. |
| 2007/0248605 | A1 | 10/2007 | Hestir et al. |
| 2008/0003240 | A1 | 1/2008 | Fernandez-Salas et al. |
| 2008/0038257 | A1 | 2/2008 | Han et al. |
| 2008/0044419 | A1 | 2/2008 | Yayon |
| 2009/0202547 | A1 | 8/2009 | Yayon et al. |

FOREIGN PATENT DOCUMENTS

| JP | 2004121026 A | 4/2004 |
|---|---|---|
| WO | WO-94/21813 A1 | 9/1994 |
| WO | WO-96/34096 A1 | 10/1996 |
| WO | WO-00/68424 A2 | 11/2000 |
| WO | WO-01/36632 A2 | 5/2001 |
| WO | WO-03/025138 A2 | 3/2003 |
| WO | WO-03/083046 A2 | 10/2003 |
| WO | WO-2004/022095 A1 | 3/2004 |
| WO | WO-2005/031001 A2 | 4/2005 |
| WO | WO-2005/115363 A2 | 12/2005 |
| WO | WO-2006/048877 A2 | 5/2006 |
| WO | WO-2006/053788 A2 | 5/2006 |
| WO | WO-2006/110581 A2 | 10/2006 |
| WO | WO-2007/144893 A2 | 12/2007 |
| WO | WO-2008/020586 A1 | 2/2008 |
| WO | WO-2008/062063 A1 | 5/2008 |

OTHER PUBLICATIONS

International Search Report for International Application No. PCT/US09/49211, date of mailing, Mar. 31, 2010 (4 pages).

Written Opinion of the International Searching Authority for International Application No. PCT/US09/49211, date of mailing, Mar. 31, 2010 (5 pages).

Chang et al. (2005) "Immunohistochemistry accurately predicts FGFR3 aberrant expression and t(4;14) in multiple myeloma" Blood, vol. 106, No. 1, pp. 353-355.

Chellaiah et al. (1994) "Fibroblast Growth Factor Receptor (FGFR) 3, Alternative Splicing in Immunoglobulin-Like Domain III Creates a Receptor Highly Specific for Acidic FGF/FGF-1" J. of Biological Chemistry, vol. 269, No. 15, pp. 11620-11627.

Chellaiah et al. (1999) "Mapping Ligand Binding Domains in Chimeric Fibroblast Growth Factor Receptor Molecules, Multiple Regions Determine Ligand Binding Specificity" J. of Biological Chemistry, vol. 274, No. 49, pp. 34785-34794.

Delezoide et al. (1997) "Abnormal FGFR3 expression in cartilage of thanatophoric dysplasia fetuses" Human Molecular Genetics, vol. 6, No. 11, pp. 1899-1906. Eswarakumar et al. (2005) "Cellular signaling by fibroblast growth receptors" Cytokine Growth Factor Rev. 16(2) pp. 139-149.

Keegan et al. (1991) "Isolation of an additional member of the fibroblast growth factor receptor family, FGFR-3" Proc. Natl. Acad. Sci. USA. 88(4), pp. 1095-1099.

Gomez-Roman et al. (2005) "Fibroblast growth factor receptor 3 is overexpressed in urinary tract carcinomas and modulates the neoplastic cell growth" Clin. Cancer Res. 11(2 pt 1), pp. 459-465.

Lappi et al. (1995) "Tumor targeting through fibroblast growth factor receptors" Semin. Cancer Biol. 6(5, pp. 279-288.

(Continued)

Primary Examiner — Lynn Bristol
(74) Attorney, Agent, or Firm — Goodwin Procter LLP

(57) ABSTRACT

Monoclonal antibodies that bind and inhibit activation of fibroblast growth factor receptor 3 (FGFR3) are disclosed. The antibodies can be used to treat cell proliferative diseases and disorders, including certain forms of cancer, associated with activation of FGFR3.

11 Claims, 10 Drawing Sheets

OTHER PUBLICATIONS

Martinez-Torrecuadrada et al. (2005) "Targeting the extracellular domain of fibroblast growth factor receptor 3 with human single-chain Fv antibodies inhibits bladder carcinoma cell line proliferation" Clin. Cancer Res. 11(17), pp. 6280-6290.

Rauchenberger et al. (2003) "Human combinatorial Fab library yielding specific and functional antibodies against the human fibroblast growth factor receptor 3" J. Biol. Chem. 278(40), pp. 38194-38205.

Johnston et al. (1995) "Fibroblast growth factor receptors (FGFRs) localize in different cellular compartments. A splice variant of FGFR-3 localizes to the nucleus" J. Biol. Chem. 270(51), pp. 30643-30650.

Scotet et al. (1995) "The choice between alternative IIIb and IIIc exons of the FGFR-3 gene is not strictly tissue-specific" Biochim. Biophys. Acta. 1264(2), pp. 238-242.

Siegall (1994) "Targeted toxins as anticancer agents" Cancer 74(3 Suppl), pp. 1006-1012.

Trudel et al. (2006) "The inhibitory anti-FGFR3 antibody, PRO-001, is cytotoxic to t(4;14) multilple myeloma cells" Blood 107(10), pp. 4039-4046.

Venkateswaran et al. (1992) "Production of anti-fibroblast growth factor receptor monoclonal antibodies by in vitro immunization" Hybridoma 11(6), pp. 729-739.

Lee et al. (2000) "Maintenance of Vascular Integrity in the Embryo Requires Signaling through the Fibroblast Growth Factor Receptor," The Journal of Biological Chemistry, 275(43):33679-33687.

Ornitz et al. (1996) "Receptor Specificity of the Fibroblast Growth Factor Family," The Journal of Biological Chemistry, 271(25):15292-15297.

Complete Heavy Chain Variable Region Amino Acid Alignments

```
Antibody    1                                                                    70
                                    CDR1                       CDR2
  15D8      EIQLQQSGPELVKPGASVKVSCKASGYAFT SYNMY WVKQSHGKSLEWIG YIDPYNGGTsYNQKFKG KATL
  27H2      EIQLQQSGPELVKPGASVKVSCKASGYAFT SYNMY WVKQSHGKSLEWIG YIDPYNGGTRYNQKFKG KATM
   2G4      EIQLQQSGPELVKPGASVKVSCKASGYAFT SYNMY WVKQSHGKSLEWIG YIDPYNGGTRdNQKFKG KATL
  4E7 (7D12) EIQLQQSGPELVKPGASVKVSCKASGYAFT SYNMY WVKQSHGKSLEWIG YIDPYNGGTRYNQKFKG KATL
  20B4      EIQLQQSGPELVKPGASVKVSCKASGYSLT DYNMY WVKQSHGKSLEWIG YIDPYNGGTSYNQKFKG KATL 71                                            CDR3               120
 (15D8 cont.)  TVDKSSSSTAYMHLNSLTSEDSAVYYCAR EGGNYEAWFAY WGQGTLVTVSA  (SEQ ID NO: 2)
 (27H2 cont.)  TVDKSSSSTAYMHLNSLTSEDSAVYYCAR EGGNYEAWFAY WGQGTLVTVSA  (SEQ ID NO: 6)
 (2G4 cont.)   TVDKSSSSTAYMHLNSLTSEDSAVYYCAR EGGNYEAWFAY WGQGTLVTVSA  (SEQ ID NO: 10)
 (7D12) cont.) TVDKSSSSTAYMHLNSLTSEDSAVYYCAR EGGNYEAWFAY WGQGTLVTVSA  (SEQ ID NO: 12)
 (20B4 cont.)  TVDKSSSSTAFMHLNSLTSEDSAVYYCAR SLG---PDFDY WGQGTTLTVSS  (SEQ ID NO: 14)
```

Fig.2

Heavy Chain CDR Amino Acid Alignments

| Antibody | CDR1 | | CDR2 | | CDR3 | |
|---|---|---|---|---|---|---|
| 15D8 | SYNMY | (SEQ ID NO: 17) | YIDPYNGGTSYNQKFKG | (SEQ ID NO: 18) | EGGNYEAWFAY | (SEQ ID NO: 19) |
| 15D8-2 | SYNMY | (SEQ ID NO: 17) | YIDPYNGGTSYNPSFQG | (SEQ ID NO: 20) | EGGNYEAWFAY | (SEQ ID NO: 19) |
| 15D8-3 | SYNMY | (SEQ ID NO: 17) | YIDPYNGGTSYNPKFKG | (SEQ ID NO: 21) | EGGNYEAWFAY | (SEQ ID NO: 19) |
| 27H2 | SYNMY | (SEQ ID NO: 17) | YIDPYNGGTRYNQKFKG | (SEQ ID NO: 25) | EGGNYEAWFAY | (SEQ ID NO: 19) |
| 2G4 | SYNMY | (SEQ ID NO: 17) | YIDPYNGGTRDNQKFKG | (SEQ ID NO: 28) | EGGNYEAWFAY | (SEQ ID NO: 19) |
| 4E7(7D12) | SYNMY | (SEQ ID NO: 17) | YIDPYNGGTRYNQKFKG | (SEQ ID NO: 25) | EGGNYEAWFAY | (SEQ ID NO: 19) |
| 20B4 | DYNMY | (SEQ ID NO: 29) | YIDPYNGGTSYNQKFKG | (SEQ ID NO: 18) | SLG---PDFDY | (SEQ ID NO: 30) |

Fig.3

Complete Light (Kappa) Chain Variable Region Amino Acid Alignments

| Antibody | CDR1 | CDR2 |
|---|---|---|
| | 1 | 70 |
| 15D8 | QIVLTQSPALMSASPGEKVTMTC SASSSVSYMY WYQQKPRSSPKPWIY LTSYLAS GVPARFSGSGSGTSY |
| 27H2 | QIVLTQSPALMSASPGEKVTMTC SASSSVSYMY WYQQKPRSSPKPWIY LTSNLAS GVPARFSGSGSGTSY |
| 2G4 | QIVLTQSPALMSASPGEKVTMTC SASSSVSYMY WYQQKPRSSPKPWIY LTSYLAS GVPARFSGSGSGTSY |
| 4E7 (and 7D12) | QIVLTQSPALMSASPGEKVTMTC SASSSVSYMY WYQQKPRSSPKPWIY LTSNLAS GVPARFSGSGSGTSY |
| 20B4 | QIVLTQSPAIMSASPGEKVTMTC SASSSVNYMH WYQQKSGTSPKRWIY DTSKLAS GVPARFSGSGSGTSY |

CDR3

| | 71 | 106 | |
|---|---|---|---|
| (15D8 cont.) | SLTISSMEAEDAATYYC QQWSSYPLT FGAGTKLELK | (SEQ ID NO: 4) |
| (27H2 cont.) | SLTISSMEAEDAATYYC QQWSSNPLT FGAGTKLELK | (SEQ ID NO: 8) |
| (2G4 cont.) | SLTISSMEAEDAATYYC QQWSSNPLT FGAGTKLELK | (SEQ ID NO: 8) |
| (4E7 (7D12) cont.) | SLTISSMEAEDAATYYC QQWSSNPLT FGAGTKLELK | (SEQ ID NO: 8) |
| (20B4 cont.) | SLTISSMEAEDTATYYC QQWNSNPLT FGAGTKLELK | (SEQ ID NO: 16) |

Fig.4

Light (Kappa) Chain CDR Amino Acid Alignments

| Antibody | CDR1 | CDR2 | CDR3 |
|---|---|---|---|
| 15D8 | SASSSVSYMY (SEQ ID NO: 22) | LTSYLAS (SEQ ID NO: 23) | QQWSSYPLT (SEQ ID NO: 24) |
| 27H2 | SASSSVSYMY (SEQ ID NO: 22) | LTSNLAS (SEQ ID NO: 26) | QQWSSNPLT (SEQ ID NO: 27) |
| 2G4 | SASSSVSYMY (SEQ ID NO: 22) | LTSNLAS (SEQ ID NO: 26) | QQWSSNPLT (SEQ ID NO: 27) |
| 4E7 (7D12) | SASSSVSYMY (SEQ ID NO: 22) | LTSNLAS (SEQ ID NO: 26) | QQWSSNPLT (SEQ ID NO: 27) |
| 20B4 | SASSSVNYMH (SEQ ID NO: 31) | DTSKLAS (SEQ ID NO: 32) | QQWNSNPLT (SEQ ID NO: 33) |

Fig.5

SEQUENCE LISTING

```
<160> NUMBER OF SEQ ID NOS: 89

<210> SEQ ID NO 1
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gagatccagc tgcagcagtc tggacctgag ctggtgaagc ctggggcttc agtgaaggta      60
tcctgcaagg cttctggtta tgcattcact agctacaaca tgtactgggt gaagcagagc     120
catggaaaga gccttgagtg gattggatat attgatcctt acaatggtgg tactagctac     180
aaccagaagt tcaagggcaa ggccacattg actgttgaca agtcctccag cacagcctac     240
atgcatctca cagcctgac atctgaggac tctgcagtct attactgtgc aagagagggg     300
ggtaactacg aggcctggtt tgcttactgg ggccaaggga ctctggtcac tgtctctgca     360

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2
```

-continued

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Glu Gly Gly Asn Tyr Glu Ala Trp Phe Ala Tyr Trp Gly Gln
            100                 105                 110

Gly Thr Leu Val Thr Val Ser Ala
        115                 120

<210> SEQ ID NO 3
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
caaattgttc tcacccagtc tccagcactc atgtctgcat ctccagggga gaaggtcacc        60
atgacctgca gtgccagctc aagtgtaagt tacatgtact ggtaccagca gaagccaaga       120
tcctccccca aaccctggat ttatctcaca tcctacctgg cttctggagt ccctgctcgc       180
ttcagtggca gtggatctgg gacctcttac tctctcacaa tcagcagcat ggaggctgaa       240
gatgctgcca cttattactg ccagcagtgg agtagttacc cgctcacgtt cggtgctgga       300
accaagctgg agctgaaa                                                     318

<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Tyr Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Leu Lys
            100                 105

<210> SEQ ID NO 5
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gagatccagc tgcagcagtc tggacctgag ctggtgaagc ctggggcttc agtgaaggta      60
tcctgcaagg cttctggtta tgcattcact agctacaaca tgtactgggt gaagcagagc     120
catggaaaga gccttgagtg gattggatat attgatcctt acaatggtgg tactaggtac     180
aaccagaagt tcaagggcaa ggccacaatg actgttgaca gtcctccag cacagcctac      240 atgcatctca acagcctgac atctgaggac tctgcagtct attactgtgc aagagagggg     300
ggtaactacg aggcctggtt tgcttactgg ggccaaggga ctctggtcac tgtctctgca     360

<210> SEQ ID NO 6
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Arg Tyr Asn Gln Lys Phe
    50                  55                  60

Lys Gly Lys Ala Thr Met Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Glu Gly Gly Asn Tyr Glu Ala Trp Phe Ala Tyr Trp Gly Gln
            100                 105                 110

Gly Thr Leu Val Thr Val Ser Ala
        115                 120

<210> SEQ ID NO 7
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
caaattgttc tcacccagtc tccagcactc atgtctgcat ctccagggga gaaggtcacc      60
atgacctgca gtgccagctc aagtgtaagt tacatgtact ggtaccagca gaagccaaga     120
tcctccccca aacctggat ttatctcaca tccaacctgg cttctggagt ccctgctcgc      180
ttcagtggca gtgggtctgg gacctcttac tctctcacaa tcagcagcat ggaggctgaa     240
gatgctgcca cttattactg ccagcagtgg agtagtaacc cgctcacgtt cggtgctggg     300
accaagctgg agctgaaa                                                   318

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met Tyr
                20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 9
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gagatccagc tgcagcagtc tggacctgag ctggtgaagc ctggggcttc agtgaaggta       60
tcctgcaagg cttctggtta tgcattcaca agctacaaca tgtactgggt gaagcagagc      120
catggaaaga gccttgagtg gattggatat attgatcctt acaatggtgg tactagggac      180
aaccagaagt tcaagggcaa ggccacattg actgttgaca gtcctccag tacagcctac       240 atgcatctca cagcctgac atctgaggac tctgcagtct attactgtgc aagagagggg       300
ggtaactacg aggcctggtt tgcttactgg ggccaaggga ctctggtcac tgtctctgca      360

<210> SEQ ID NO 10
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
                20                  25                  30

Asn Met Tyr Trp Val Lys Gln Ser His Gly Lys Ser Leu Glu Trp Ile
            35                  40                  45

Gly Tyr Ile Asp Pro Tyr Asn Gly Gly Thr Arg Asp Asn Gln Lys Phe
        50                  55                  60

Lys Gly Lys Ala Thr Leu Thr Val Asp Lys Ser Ser Ser Thr Ala Tyr

```
                    65                  70                  75                  80
Met His Leu Asn Ser Leu Thr Ser Glu Asp Ser Ala Val Tyr Tyr Cys
                        85                  90                  95

Ala Arg Glu Gly Gly Asn Tyr Glu Ala Trp Phe Ala Tyr Trp Gly Gln
                100                 105                 110

Gly Thr Leu Val Thr Val Ser Ala
                115                 120

<210> SEQ ID NO 11
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gagatccagc tgcagcagtc tggacctgag ctggtgaagc ctggggcttc agtgaaggta     60
tcctgcaagg cttctggtta cattcact agctacaaca tgtactgggt gaagcagagc     120
catggaaaga gccttgagtg gattggatat attgatcctt acaatggtgg tactaggtac    180
aaccagaagt tcaagggcaa ggccacattg actgttgaca agtcctccag cacagcctac    240
atgcatctca acagcctgac atctgaggac tctgcagtct attactgtgc aagagagggg    300
ggtaactacg aggcctggtt tgcttactgg ggccaaggga ctctggtcac tgtctctgca    360

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
                20                  25                  30

Asn Met Tyr Trp Val Lys Gln Ser His Gly Lys Ser Leu Glu Trp Ile
            35                  40                  45

Gly Tyr Ile Asp Pro Tyr Asn Gly Gly Thr Arg Tyr Asn Gln Lys Phe
        50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Glu Gly Gly Asn Tyr Glu Ala Trp Phe Ala Tyr Trp Gly Gln
                100                 105                 110

Gly Thr Leu Val Thr Val Ser Ala
                115                 120

<210> SEQ ID NO 13
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
```

```
gagatccagc tgcagcagtc tggacctgag ctggtgaagc ctggggcttc agtgaaggta      60
tcctgcaagg cttctggtta ctcactcact gactacaaca tgtactgggt gaagcagagc     120
catggaaaga gccttgagtg gattggatat attgatcctt acaatggtgg tactagctac     180
aaccagaagt tcaagggcaa ggccacattg actgttgaca gtcctccag cacagccttc      240 atgcatctca acagcctgac atctgaggac tctgcagtct attactgtgc aagatcgttg     300
ggacctgatt ttgactactg gggccaaggc accactctca cagtctcctc a              351

<210> SEQ ID NO 14
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Leu Thr Asp Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Phe
65                  70                  75                  80

Met His Leu Asn Ser Leu Thr Ser Glu Asp Ser Ala Val Tyr Tyr Cys
                85                  90                  95

Ala Arg Ser Leu Gly Pro Asp Phe Asp Tyr Trp Gly Gln Gly Thr Thr
            100                 105                 110

Leu Thr Val Ser Ser
        115

<210> SEQ ID NO 15
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
caaattgttc tcacccagtc tccagcaatc atgtctgcat ctccagggga aaggtcacc      60 atgacctgca gtgccagctc aagtgtaaat tacatgcact ggtaccagca gaagtcaggc    120
acctccccca aaagatggat ttatgacaca tccaaactgg cttctggagt ccctgctcgc    180
ttcagtggca gtgggtctgg gacctcttac tctctcacaa tcagcagcat ggaggctgaa    240
gatactgcca cttattactg tcaacagtgg aatagtaacc cactcacgtt cggtgcgggg    300
accaagctgg agctgaaa                                                  318

<210> SEQ ID NO 16
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16
```

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Asn Tyr Met
                20                  25                  30

His Trp Tyr Gln Gln Lys Ser Gly Thr Ser Pro Lys Arg Trp Ile Tyr
                35                  40                  45

Asp Thr Ser Lys Leu Ala Ser Gly Val Pro Ala Arg Phe Ser Gly Ser
            50                  55                  60

Gly Ser Gly Thr Ser Tyr Ser Leu Thr Ile Ser Ser Met Glu Ala Glu
65              70                  75                  80

Asp Thr Ala Thr Tyr Tyr Cys Gln Gln Trp Asn Ser Asn Pro Leu Thr
                85                  90                  95

Phe Gly Ala Gly Thr Lys Leu Glu Leu Lys
            100                 105

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Tyr Asn Met Tyr
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Ile Asp Pro Tyr Asn Gly Gly Thr Ser Tyr Asn Gln Lys Phe Lys
1               5                   10                  15

Gly

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Gly Gly Asn Tyr Glu Ala Trp Phe Ala Tyr
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Ile Asp Pro Tyr Asn Gly Gly Thr Ser Tyr Asn Pro Ser Phe Gln
1               5                   10                  15
```

-continued

Gly

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Ile Asp Pro Tyr Asn Gly Gly Thr Ser Tyr Asn Pro Lys Phe Lys
1               5                   10                  15
Gly

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ala Ser Ser Ser Val Ser Tyr Met Tyr
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Thr Ser Tyr Leu Ala Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln Trp Ser Ser Tyr Pro Leu Thr
1               5

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Ile Asp Pro Tyr Asn Gly Gly Thr Arg Tyr Asn Gln Lys Phe Lys
1               5                   10                  15
Gly

<210> SEQ ID NO 26
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 26

Leu Thr Ser Asn Leu Ala Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Gln Trp Ser Ser Asn Pro Leu Thr
1               5

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Ile Asp Pro Tyr Asn Gly Gly Thr Arg Asp Asn Gln Lys Phe Lys
1               5                   10                  15

Gly

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Tyr Asn Met Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Leu Gly Pro Asp Phe Asp Tyr
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Ala Ser Ser Ser Val Asn Tyr Met His
```

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Asp Thr Ser Lys Leu Ala Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gln Gln Trp Asn Ser Asn Pro Leu Thr
1               5

<210> SEQ ID NO 34
<211> LENGTH: 972
<212> TYPE: DNA
<213> ORGANISM: Mus sp.

<400> SEQUENCE: 34

```
gccaaaacga cacccccatc tgtctatcca ctggccccctg gatctgctgc ccaaactaac      60
tccatggtga ccctgggatg cctggtcaag ggctatttcc ctgagccagt gacagtgacc     120
tggaactctg gatccctgtc cagcggtgtg cacaccttcc cagctgtcct gcagtctgac     180
ctctacactc tgagcagctc agtgactgtc ccctccagca cctggcccag cgagaccgtc     240
acctgcaacg ttgcccaccc ggccagcagc accaaggtgg acaagaaaat tgtgcccagg     300
gattgtggtt gtaagccttg catatgtaca gtcccagaag tatcatctgt cttcatcttc     360
cccccaaagc ccaaggatgt gctcaccatt actctgactc ctaaggtcac gtgtgttgtg     420
gtagacatca gcaaggatga tcccgaggtc cagttcagct ggtttgtaga tgatgtggag     480
gtgcacacag ctcagacgca accccgggag gagcagttca acagcacttt ccgctcagtc     540
agtgaacttc ccatcatgca ccaggactgg ctcaatggca aggagttcaa atgcagggtc     600
aacagtgcag ctttccctgc ccccatcgag aaaaccatct ccaaaaccaa aggcagaccg     660
aaggctccac aggtgtacac cattccacct cccaaggagc agatggccaa ggataaagtc     720
agtctgacct gcatgataac agacttcttc cctgaagaca ttactgtgga gtggcagtgg     780
aatgggcagc cagcggagaa ctacaagaac actcagccca tcatggacac agatggctct     840
tacttcgtct acagcaagct caatgtgcag aagagcaact gggaggcagg aaatactttc     900
acctgctctg tgttacatga gggcctgcac aaccaccata ctgagaagag cctctcccac     960
tctcctggta aa                                                        972
```

<210> SEQ ID NO 35
<211> LENGTH: 324
<212> TYPE: PRT
<213> ORGANISM: Mus sp.

<400> SEQUENCE: 35

```
Ala Lys Thr Thr Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
290                 295                 300

Leu His Glu Gly Leu His Asn His His Thr Glu Lys Ser Leu Ser His
305                 310                 315                 320

Ser Pro Gly Lys

<210> SEQ ID NO 36
<211> LENGTH: 321
<212> TYPE: DNA
<213> ORGANISM: Mus sp.

<400> SEQUENCE: 36
cgggctgatg ctgcaccaac tgtatccatc ttcccaccat ccagtgagca gttaacatct     60
ggaggtgcct cagtcgtgtg cttcttgaac aacttctacc ccaaagacat caatgtcaag    120
tggaagattg atggcagtga acgacaaaat ggcgtcctga cagttggac tgatcaggac    180 agcaaagaca gcacctacag catgagcagc accctcacgt tgaccaagga cgagtatgaa    240
cgacataaca gctatacctg tgaggccact cacaagacat caacttcacc cattgtcaag    300
```
agcttcaaca ggaatgagtg t                                              321

<210> SEQ ID NO 37
<211> LENGTH: 107
<212> TYPE: PRT
<213> ORGANISM: Mus sp.

<400> SEQUENCE: 37

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 38
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gagatccagc tgcagcagtc tggacctgag ctggtgaagc ctggggcttc agtgaaggta    60
tcctgcaagg cttctggtta tgcattcact agctacaaca tgtactgggt gaagcagagc   120
catggaaaga gccttgagtg gattggatat attgatcctt acaatggtgg tactagctac   180
aaccagaagt tcaagggcaa ggccacattg actgttgaca gtcctccag cacagcctac    240 atgcatctca acagcctgac atctgaggac tctgcagtct attactgtgc aagagagggg   300
ggtaactacg aggcctggtt tgcttactgg ggccaaggga ctctggtcac tgtctctgca   360
gccaaaacga cacccccatc tgtctatcca ctggcccctg gatctgctgc ccaaactaac   420
tccatggtga ccctgggatg cctggtcaag ggctatttcc ctgagccagt gacagtgacc   480
tggaactctg gatccctgtc agcggtgtg cacaccttcc cagctgtcct gcagtctgac    540
ctctacactc tgagcagctc agtgactgtc ccctccagca cctggcccag cgagaccgtc   600
acctgcaacg ttgcccaccc ggccagcagc accaaggtgg acaagaaaat tgtgcccagg   660
gattgtggtt gtaagccttg catatgtaca gtcccagaag tatcatctgt cttcatcttc   720
cccccaaagc ccaaggatgt gctcaccatt actctgactc ctaaggtcac gtgtgttgtg   780
gtagacatca gcaaggatga tcccgaggtc cagttcagct ggtttgtaga tgatgtggag   840
gtgcacacag ctcagacgca accccgggag gagcagttca acagcacttt ccgctcagtc   900
agtgaacttc ccatcatgca ccaggactgg ctcaatggca aggagttcaa atgcagggtc   960
aacagtgcag cttttcctgc ccccatcgag aaaaccatct ccaaaaccaa aggcagaccg  1020
aaggctccac aggtgtacac cattccacct cccaaggagc agatggccaa ggataaagtc  1080
agtctgacct gcatgataac agacttcttc cctgaagaca ttactgtgga gtggcagtgg  1140

-continued

```
aatgggcagc cagcggagaa ctacaagaac actcagccca tcatggacac agatggctct    1200
tacttcgtct acagcaagct caatgtgcag aagagcaact gggaggcagg aaatactttc    1260
acctgctctg tgttacatga gggcctgcac aaccaccata ctgagaagag cctctcccac    1320
tctcctggta aa                                                        1332
```

<210> SEQ ID NO 39
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Glu Gly Gly Asn Tyr Glu Ala Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
```

```
                    325                 330                 335
Lys Gly Arg Pro Lys Ala Pro Gln Val Tyr Thr Ile Pro Pro Lys
                340                 345                 350

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Lys
                435                 440
```

<210> SEQ ID NO 40
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
caaattgttc tcacccagtc tccagcactc atgtctgcat ctccagggga gaaggtcacc      60
atgacctgca gtgccagctc aagtgtaagt tacatgtact ggtaccagca gaagccaaga     120
tcctccccca aaccctggat ttatctcaca tcctacctgg cttctggagt ccctgctcgc     180
ttcagtggca gtggatctgg gacctcttac tctctcacaa tcagcagcat ggaggctgaa     240
gatgctgcca cttattactg ccagcagtgg agtagttacc cgctcacgtt cggtgctgga     300
accaagctgg agctgaaacg ggctgatgct gcaccaactg tatccatctt cccaccatcc     360
agtgagcagt taacatctgg aggtgcctca gtcgtgtgct tcttgaacaa cttctacccc     420
aaagacatca atgtcaagtg gaagattgat ggcagtgaac gacaaaatgg cgtcctgaac     480
agttggactg atcaggacag caaagacagc acctacagca tgagcagcac cctcacgttg     540
accaaggacg agtatgaacg acataacagc tatacctgtg aggccactca caagacatca     600
acttcaccca ttgtcaagag cttcaacagg aatgagtgt                           639
```

<210> SEQ ID NO 41
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Tyr Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
```

```
                65                  70                  75                  80
Asp Ala Ala Thr Tyr Tyr Cys Gln Gln Trp Ser Ser Tyr Pro Leu Thr
                    85                  90                  95
Phe Gly Ala Gly Thr Lys Leu Glu Leu Lys Arg Ala Asp Ala Ala Pro
                100                 105                 110
Thr Val Ser Ile Phe Pro Pro Ser Glu Gln Leu Thr Ser Gly Gly
        115                 120                 125
Ala Ser Val Val Cys Phe Leu Asn Asn Phe Tyr Pro Lys Asp Ile Asn
    130                 135                 140
Val Lys Trp Lys Ile Asp Gly Ser Glu Arg Gln Asn Gly Val Leu Asn
145                 150                 155                 160
Ser Trp Thr Asp Gln Asp Ser Lys Asp Ser Thr Tyr Ser Met Ser Ser
                165                 170                 175
Thr Leu Thr Leu Thr Lys Asp Glu Tyr Glu Arg His Asn Ser Tyr Thr
                180                 185                 190
Cys Glu Ala Thr His Lys Thr Ser Thr Ser Pro Ile Val Lys Ser Phe
            195                 200                 205
Asn Arg Asn Glu Cys
    210

<210> SEQ ID NO 42
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gagatccagc tgcagcagtc tggacctgag ctggtgaagc ctggggcttc agtgaaggta      60
tcctgcaagg cttctggtta tgcattcact agctacaaca tgtactgggt gaagcagagc     120
catggaaaga gccttgagtg gattggatat attgatcctt acaatggtgg tactaggtac     180
aaccagaagt tcaagggcaa ggccacaatg actgttgaca gtcctccag cacagcctac      240 atgcatctca cagcctgac atctgaggac tctgcagtct attactgtgc aagagaggggg     300 ggtaactacg aggcctggtt tgcttactgg ggccaaggga ctctggtcac tgtctctgca     360
gccaaaacga cacccccatc tgtctatcca ctggcccctg gatctgctgc ccaaactaac     420
tccatggtga ccctgggatg cctggtcaag gctatttcc ctgagccagt gacagtgacc      480
tggaactctg gatccctgtc cagcggtgtg cacaccttcc cagctgtcct gcagtctgac     540
ctctacactc tgagcagctc agtgactgtc cctccagca cctggcccag cgagaccgtc      600
acctgcaacg ttgcccaccc ggccagcagc accaaggtgg acaagaaaat tgtgcccagg     660
gattgtggtt gtaagccttg catatgtaca gtcccagaag tatcatctgt cttcatcttc     720
cccccaaagc ccaaggatgt gctcaccatt actctgactc ctaaggtcac gtgtgttgtg     780
gtagacatca gcaaggatga tcccgaggtc cagttcagct ggtttgtaga tgatgtggag     840
gtgcacacag ctcagacgca accccgggag gagcagttca acagcacttt ccgctcagtc     900
agtgaacttc ccatcatgca ccaggactgg ctcaatggca aggagttcaa atgcagggtc     960
aacagtgcag ctttccctgc ccccatcgag aaaaccatct ccaaaaccaa aggcagaccg    1020
aaggctccac aggtgtacac cattccacct cccaaggagc agatggccaa ggataaagtc    1080
agtctgacct gcatgataac agacttcttc cctgaagaca ttactgtgga gtggcagtgg    1140
aatgggcagc cagcggagaa ctacaagaac actcagccca tcatggacac agatggctct    1200
```

```
tacttcgtct acagcaagct caatgtgcag aagagcaact gggaggcagg aaatactttc      1260
acctgctctg tgttacatga gggcctgcac aaccaccata ctgagaagag cctctcccac      1320
tctcctggta aa                                                          1332
```

<210> SEQ ID NO 43
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Arg Tyr Asn Gln Lys Phe
    50                  55                  60

Lys Gly Lys Ala Thr Met Thr Val Asp Lys Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Glu Gly Gly Asn Tyr Glu Ala Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335
```

Lys Gly Arg Pro Lys Ala Pro Gln Val Tyr Thr Ile Pro Pro Pro Lys
              340                 345                 350

Glu Gln Met Ala Lys Asp Lys Val Ser Leu Thr Cys Met Ile Thr Asp
              355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
              405                 410                 415

Gly Asn Thr Phe Thr Cys Ser Val Leu His Glu Gly Leu His Asn His
              420                 425                 430

His Thr Glu Lys Ser Leu Ser His Ser Pro Gly Lys
              435                 440

<210> SEQ ID NO 44
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
caaattgttc tcacccagtc tccagcactc atgtctgcat ctccagggga gaaggtcacc      60
atgacctgca gtgccagctc aagtgtaagt tacatgtact ggtaccagca gaagccaaga     120 tcctcccca aaccctggat ttatctcaca tccaacctgg cttctggagt ccctgctcgc     180
ttcagtggca gtgggtctgg gacctcttac tctctcacaa tcagcagcat ggaggctgaa     240
gatgctgcca cttattactg ccagcagtgg agtagtaacc cgctcacgtt cggtgctggg     300
accaagctgg agctgaaacg ggctgatgct gcaccaactg tatccatctt cccaccatcc     360
agtgagcagt taacatctgg aggtgcctca gtcgtgtgct tcttgaacaa cttctacccc     420
aaagacatca atgtcaagtg gaagattgat ggcagtgaac gacaaaatgg cgtcctgaac     480
agttggactg atcaggacag caaagacagc acctacagca tgagcagcac cctcacgttg     540
accaaggacg agtatgaacg acataacagc tatacctgtg aggccactca caagacatca     600
acttcaccca ttgtcaagag cttcaacagg aatgagtgt                             639

<210> SEQ ID NO 45
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
              20                  25                  30

Tyr Trp Tyr Gln Gln Lys Pro Arg Ser Ser Pro Lys Pro Trp Ile Tyr
          35                  40                  45

Leu Thr Ser Asn Leu Ala Ser Gly Val Pro Ala Arg Phe Ser Gly Ser
      50                  55                  60

Gly Ser Gly Thr Ser Tyr Ser Leu Thr Ile Ser Ser Met Glu Ala Glu
65                  70                  75                  80

```
Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Ala Asp Ala Ala Pro
        100                 105                 110

Thr Val Ser Ile Phe Pro Pro Ser Ser Glu Gln Leu Thr Ser Gly Gly
    115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 46
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

| | |
|---|---|
| gagatccagc tgcagcagtc tggacctgag ctggtgaagc ctggggcttc agtgaaggta | 60 |
| tcctgcaagg cttctggtta tgcattcaca agctacaaca tgtactgggt gaagcagagc | 120 |
| catggaaaga gccttgagtg gattggatat attgatcctt acaatggtgg tactagggac | 180 |
| aaccagaagt tcaagggcaa ggccacattg actgttgaca gtcctccag tacagcctac | 240 |
| atgcatctca acagcctgac atctgaggac tctgcagtct attactgtgc aagagaggg | 300 |
| ggtaactacg aggcctggtt tgcttactgg ggccaaggga ctctggtcac tgtctctgca | 360 |
| gccaaaacga cacccccatc tgtctatcca ctggcccctg gatctgctgc ccaaactaac | 420 |
| tccatggtga ccctgggatg cctggtcaag ggctatttcc ctgagccagt gacagtgacc | 480 |
| tggaactctg gatccctgtc agcggtgtg cacaccttcc cagctgtcct gcagtctgac | 540 |
| ctctacactc tgagcagctc agtgactgtc cctccagca cctggcccag cgagaccgtc | 600 |
| acctgcaacg ttgcccaccc ggccagcagc accaaggtgg acaagaaaat tgtgcccagg | 660 |
| gattgtggtt gtaagccttg catatgtaca gtcccagaag tatcatctgt cttcatcttc | 720 |
| cccccaaagc ccaaggatgt gctcaccatt actctgactc ctaaggtcac gtgtgttgtg | 780 |
| gtagacatca gcaaggatga tcccgaggtc cagttcagct ggtttgtaga tgatgtggag | 840 |
| gtgcacacag ctcagacgca accccgggag gagcagttca acagcacttt ccgctcagtc | 900 |
| agtgaacttc ccatcatgca ccaggactgg ctcaatggca aggagttcaa atgcagggtc | 960 |
| aacagtgcag ctttccctgc ccccatcgag aaaaccatct ccaaaaccaa aggcagaccg | 1020 |
| aaggctccac aggtgtacac cattccacct cccaaggagc agatggccaa ggataaagtc | 1080 |
| agtctgacct gcatgataac agacttcttc cctgaagaca ttactgtgga gtggcagtgg | 1140 |
| aatgggcagc cagcggagaa ctacaagaac actcagccca tcatggacac agatggctct | 1200 |
| tacttcgtct acagcaagct caatgtgcag aagagcaact gggaggcagg aaatactttc | 1260 |

```
acctgctctg tgttacatga gggcctgcac aaccaccata ctgagaagag cctctcccac    1320
tctcctggta aa                                                        1332
```

<210> SEQ ID NO 47
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
                20                  25                  30

Asn Met Tyr Trp Val Lys Gln Ser His Gly Lys Ser Leu Glu Trp Ile
            35                  40                  45

Gly Tyr Ile Asp Pro Tyr Asn Gly Gly Thr Arg Asp Asn Gln Lys Phe
        50                  55                  60

Lys Gly Lys Ala Thr Leu Thr Val Asp Lys Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Glu Gly Gly Asn Tyr Glu Ala Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350
```

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
            435                 440

<210> SEQ ID NO 48
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
caaattgttc tcacccagtc tccagcactc atgtctgcat ctccagggga gaaggtcacc    60
atgacctgca gtgccagctc aagtgtaagt tacatgtact ggtaccagca gaagccaaga   120
tcctccccca aaccctggat ttatctcaca tccaacctgg cttctggagt ccctgctcgc   180
ttcagtggca gtgggtctgg gacctcttac tctctcacaa tcagcagcat ggaggctgaa   240
gatgctgcca cttattactg ccagcagtgg agtagtaacc cgctcacgtt cggtgctggg   300
accaagctgg agctgaaacg ggctgatgct gcaccaactg tatccatctt cccaccatcc   360
agtgagcagt taacatctgg aggtgcctca gtcgtgtgct tcttgaacaa cttctacccc   420
aaagacatca atgtcaagtg gaagattgat ggcagtgaac gacaaaatgg cgtcctgaac   480
agttggactg atcaggacag caaagacagc acctacagca tgagcagcac cctcacgttg   540
accaaggacg agtatgaacg acataacagc tatacctgtg aggccactca caagacatca   600
acttcaccca ttgtcaagag cttcaacagg aatgagtgt                          639

<210> SEQ ID NO 49
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 50
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gagatccagc tgcagcagtc tggacctgag ctggtgaagc ctggggcttc agtgaaggta     60
tcctgcaagg cttctggtta tgcattcact agctacaaca tgtactgggt gaagcagagc    120
catggaaaga gccttgagtg gattggatat attgatcctt acaatggtgg tactaggtac    180
aaccagaagt tcaagggcaa ggccacattg actgttgaca gtcctccag cacagcctac     240 atgcatctca acagcctgac atctgaggac tctgcagtct attactgtgc aagagagggg    300
ggtaactacg aggcctggtt tgcttactgg ggccaaggga ctctggtcac tgtctctgca    360
gccaaaacga caccccccatc tgtctatcca ctggccctg atctgctgc ccaaactaac      420 tccatggtga ccctgggatg cctggtcaag ggctatttcc ctgagccagt gacagtgacc    480
tggaactctg gatccctgtc cagcggtgtg cacaccttcc cagctgtcct gcagtctgac    540
ctctacactc tgagcagctc agtgactgtc ccctccagca cctggcccag cgagaccgtc    600
acctgcaacg ttgcccaccc ggccagcagc accaaggtgg acaagaaaat tgtgcccagg    660
gattgtggtt gtaagccttg catatgtaca gtcccagaag tatcatctgt cttcatcttc    720
cccccaaagc ccaaggatgt gctcaccatt actctgactc ctaaggtcac gtgtgttgtg    780
gtagacatca gcaaggatga tcccgaggtc cagttcagct ggtttgtaga tgatgtggag    840
gtgcacacag ctcagacgca accccgggag gagcagttca acagcacttt ccgctcagtc    900
agtgaacttc ccatcatgca ccaggactgg ctcaatggca aggagttcaa atgcagggtc    960
aacagtgcag ctttccctgc ccccatcgag aaaaccatct ccaaaaccaa aggcagaccg   1020
aaggctccac aggtgtacac cattccacct cccaaggagc agatggccaa ggataaagtc   1080
agtctgacct gcatgataac agacttcttc cctgaagaca ttactgtgga gtggcagtgg   1140
aatgggcagc cagcggagaa ctacaagaac actcagccca tcatggacac agatggctct   1200
tacttcgtct acagcaagct caatgtgcag aagagcaact gggaggcagg aaatactttc   1260
acctgctctg tgttacatga gggcctgcac aaccaccata ctgagaagag cctctcccac   1320
tctcctggta aa 1332

<210> SEQ ID NO 51
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Glu Ile Gln Leu Gln Gln Ser Gly Pro Glu Leu Val Lys Pro Gly Ala
 1               5                  10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Glu Gly Gly Asn Tyr Glu Ala Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
```

355                 360                 365
Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Lys
                435                 440

<210> SEQ ID NO 52
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
caaattgttc tcacccagtc tccagcactc atgtctgcat ctccagggga gaaggtcacc      60
atgacctgca gtgccagctc aagtgtaagt tacatgtact ggtaccagca gaagccaaga     120
tcctccccca aaccctggat ttatctcaca tccaacctgg cttctggagt ccctgctcgc     180
ttcagtggca gtgggtctgg gacctcttac tctctcacaa tcagcagcat ggaggctgaa     240
gatgctgcca cttattactg ccagcagtgg agtagtaacc cgctcacgtt cggtgctggg     300
accaagctgg agctgaaacg ggctgatgct gcaccaactg tatccatctt cccaccatcc     360
agtgagcagt taacatctgg aggtgcctca gtcgtgtgct tcttgaacaa cttctacccc     420
aaagacatca atgtcaagtg gaagattgat ggcagtgaac gacaaaatgg cgtcctgaac     480
agttggactg atcaggacag caaagacagc acctacagca tgagcagcac cctcacgttg     540
accaaggacg agtatgaacg acataacagc tatacctgtg aggccactca caagacatca     600
acttcaccca ttgtcaagag cttcaacagg aatgagtgt                           639

<210> SEQ ID NO 53
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Ala Asp Ala Ala Pro

```
          100             105                 110
Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 54
<211> LENGTH: 1323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
gagatccagc tgcagcagtc tggacctgag ctggtgaagc ctggggcttc agtgaaggta    60
tcctgcaagg cttctggtta ctcactcact gactacaaca tgtactgggt gaagcagagc   120
catggaaaga gccttgagtg gattggatat attgatcctt acaatggtgg tactagctac   180
aaccagaagt tcaagggcaa ggccacattg actgttgaca agtcctccag cacagccttc   240
atgcatctca cagcctgac atctgaggac tctgcagtct attactgtgc aagatcgttg   300
ggacctgatt ttgactactg gggccaaggc accactctca cagtctcctc agccaaaacg   360
acacccccat ctgtctatcc actggcccct ggatctgctg cccaaactaa ctccatggtg   420
accctgggat gcctggtcaa gggctatttc cctgagccag tgacagtgac ctggaactct   480
ggatccctgt ccagcggtgt gcacaccttc ccagctgtcc tgcagtctga cctctacact   540
ctgagcagct cagtgactgt cccctccagc acctggccca gcgagaccgt cacctgcaac   600
gttgcccacc cggccagcag caccaaggtg gacaagaaaa ttgtgcccag ggattgtggt   660
tgtaagcctt gcatatgtac agtcccagaa gtatcatctg tcttcatctt ccccccaaag   720
cccaaggatg tgctcaccat tactctgact cctaaggtca cgtgtgttgt ggtagacatc   780
agcaaggatg atcccgaggt ccagttcagc tggtttgtag atgatgtgga ggtgcacaca   840
gctcagacgc aaccccggga ggagcagttc aacagcactt tccgctcagt cagtgaactt   900
cccatcatgc accaggactg gctcaatggc aaggagttca atgcagggt caacagtgca   960 gctttccctg cccccatcga gaaaaccatc tccaaaacca aggcagacc gaaggctcca  1020 caggtgtaca ccattccacc tcccaaggag cagatggcca aggataaagt cagtctgacc  1080
tgcatgataa cagacttctt ccctgaagac attactgtgg agtggcagtg gaatgggcag  1140
ccagcggaga actacaagaa cactcagccc atcatggaca gatggctc ttacttcgtc  1200 tacagcaagc tcaatgtgca gaagagcaac tgggaggcag gaaatacttt cacctgctct  1260
gtgttacatg agggcctgca caaccaccat actgagaaga gcctctccca ctctcctggt  1320
aaa                                                                1323
```

<210> SEQ ID NO 55
<211> LENGTH: 441
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Leu Thr Asp Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Ser Tyr Asn Gln Lys Phe
    50                  55                  60

Lys Gly Lys Ala Thr Leu Thr Val Asp Lys Ser Ser Thr Ala Phe
65                  70                  75                  80

Met His Leu Asn Ser Leu Thr Ser Glu Asp Ser Ala Val Tyr Tyr Cys
                85                  90                  95

Ala Arg Ser Leu Gly Pro Asp Phe Asp Tyr Trp Gly Gln Gly Thr Thr
            100                 105                 110

Leu Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
        355                 360                 365
```

Glu Asp Ile Thr Val Glu Trp Gln Trp Asn Gly Gln Pro Ala Glu Asn
370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
                420                 425                 430

Lys Ser Leu Ser His Ser Pro Gly Lys
                435                 440

<210> SEQ ID NO 56
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
caaattgttc tcacccagtc tccagcaatc atgtctgcat ctccagggga gaaggtcacc     60
atgacctgca gtgccagctc aagtgtaaat tacatgcact ggtaccagca gaagtcaggc    120
acctccccca aaagatggat ttatgacaca tccaaactgg cttctggagt ccctgctcgc    180
ttcagtggca gtgggtctgg gacctcttac tctctcacaa tcagcagcat ggaggctgaa    240
gatactgcca cttattactg tcaacagtgg aatagtaacc cactcacgtt cggtgcgggg    300
accaagctgg agctgaaacg ggctgatgct gcaccaactg tatccatctt cccaccatcc    360
agtgagcagt taacatctgg aggtgcctca gtcgtgtgct tcttgaacaa cttctacccc    420
aaagacatca atgtcaagtg gaagattgat ggcagtgaac gacaaaatgg cgtcctgaac    480
agttggactg atcaggacag caaagacagc acctacagca tgagcagcac cctcacgttg    540
accaaggacg agtatgaacg acataacagc tatacctgtg aggccactca caagacatca    600
acttcaccca ttgtcaagag cttcaacagg aatgagtgt                           639

<210> SEQ ID NO 57
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Thr Ala Thr Tyr Tyr Cys Gln Gln Trp Asn Ser Asn Pro Leu Thr
                85                  90                  95

Phe Gly Ala Gly Thr Lys Leu Glu Leu Lys Arg Ala Asp Ala Ala Pro
                100                 105                 110

```
Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cgactggagc acgaggacac tga                                            23

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tatgcaaggc ttacaaccac a                                              21

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gccagtggat agacagatgg gggtgtcg                                       28

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ctcattcctg ttgaagctct tgacaat                                        27

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                                      primer

<400> SEQUENCE: 62
cgactgaggc acctccagat gtt                                             23

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gtaaaacgac ggccagt                                                    17

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
caggaaacag ctatgacc                                                   18

<210> SEQ ID NO 65
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gagatccagc tgcagcagtc tggacctgag ctggtgaagc ctggggcttc agtgaaggta     60
tcctgcaagg cttctggtta tgcattcact agctacaaca tgtactgggt gaagcagagc    120
catggaaaga gccttgagtg gattggatat attgatcctt acaatggtgg tactagctac    180
aaccagaagt tcaagggcaa ggccacattg actgttgaca gtcctccag cacagcctac     240 atgcatctca cagcctgac atctgaggac tctgcagtct attactgtgc aagagagggg     300
ggtaactacg aggcctggtt tgcttactgg ggccaaggga ctctggtcac tgtctctgca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcggggagga gcagtacaac    900 agcacgtacc gtgtggtcag cgtcctcacc gtcctgcacc aggactggct gaatggcaag    960
gagtacaagt gcaaggtctc caacaaagcc ctcccagccc ccatcgagaa gaccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
```
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                     1350

<210> SEQ ID NO 66
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Glu Gly Gly Asn Tyr Glu Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 67
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
caaattgttc tcacccagtc tccagcactc atgtctgcat ctccagggga gaaggtcacc      60
atgacctgca gtgccagctc aagtgtaagt tacatgtact ggtaccagca gaagccaaga     120
tcctccccca aaccctggat ttatctcaca tcctacctgg cttctggagt ccctgctcgc     180
ttcagtggca gtggatctgg gacctcttac tctctcacaa tcagcagcat ggaggctgaa     240
gatgctgcca cttattactg ccagcagtgg agtagttacc cgctcacgtt cggtgctgga     300
accaagctgg agctgaaacg aactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgt                            639

<210> SEQ ID NO 68
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45
```

-continued

Leu Thr Ser Tyr Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Tyr Pro Leu Thr
                 85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 69
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
gaggtccaac tggtgcaatc tggggctgag gtcaagaaac ccggggaatc tctcaaaatt      60
tcatgcaaag ttctggttac agtttcacc tcatataaca tgtactgggt taggcagatg      120
cctggtaaag gcttggagtg gatggggtac attgatccct ataacggcgg cactagttac      180
aatcagaagt tcaagggcaa ggccacattg actgttgaca gtccatctc aactgcttac      240 ctgcaatggt cctctctcaa agccagcgac actgctatgt actactgcgc aagggaggga      300
ggcaattacg aggcttggtt cgcttattgg ggacaaggca ctcttgtcac cgtctcctca      360

<210> SEQ ID NO 70
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30

Asn Met Tyr Trp Val Arg Gln Met Pro Gly Lys Gly Leu Glu Trp Met
             35                  40                  45

Gly Tyr Ile Asp Pro Tyr Asn Gly Gly Thr Ser Tyr Asn Gln Lys Phe
     50                  55                  60

Lys Gly Lys Ala Thr Leu Thr Val Asp Lys Ser Ile Ser Thr Ala Tyr

```
                65                  70                  75                  80
Leu Gln Trp Ser Ser Leu Lys Ala Ser Asp Thr Ala Met Tyr Tyr Cys
                        85                  90                  95

Ala Arg Glu Gly Gly Asn Tyr Glu Ala Trp Phe Ala Tyr Trp Gly Gln
                100                 105                 110

Gly Thr Leu Val Thr Val Ser Ser
            115                 120

<210> SEQ ID NO 71
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gatatccaac tcacccagtc cccttcatcc ctgtctgcat cagtcgggga cagagtgaca      60
attacttgtt ccgccagctc tagtgtctca tacatgtatt ggtttcagca aaagccagga    120
aaagctccca aaccctgat ctatctgacc agctatctgg caagcggcgt gccttctcgg     180
ttcagtggat cagggtccgg tacagacttt accctgacta ttagcagtct gcaaccagag    240
gacttcgcca cttattactg ccaacagtgg agttcatatc ccctgacttt tggcggaggg    300
accaaggtcg agatcaag                                                   318

<210> SEQ ID NO 72
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Phe Gln Gln Lys Pro Gly Lys Ala Pro Lys Pro Leu Ile Tyr
        35                  40                  45

Leu Thr Ser Tyr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Tyr Pro Leu Thr
                85                  90                  95

Phe Gly Gly Gly Thr Lys Val Glu Ile Lys
            100                 105

<210> SEQ ID NO 73
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gaggtccaac tggtgcaatc tggggctgag gtcaagaaac cggggaatc tctcaaaatt      60 tcatgcaaag gttctggtta cagtttcacc tcatataaca tgtactgggt taggcagatg    120
```

```
cctggtaaag gcttggagtg gatggggtac attgatccct ataacggcgg cactagttac    180
aatcagaagt tcaagggcaa ggccacattg actgttgaca agtccatctc aactgcttac    240
ctgcaatggt cctctctcaa agccagcgac actgctatgt actactgcgc aagggaggga    300
ggcaattacg aggcttggtt cgcttattgg ggacaaggca ctcttgtcac cgtctcctca    360
gcctcaacaa aaggaccaag tgtgttccca ctcgccccta gcagcaagag tacatccggg    420
ggcactgcag cactcggctg cctcgtcaag gattattttc cagagccagt aaccgtgagc    480
tggaacagtg gagcactcac ttctggtgtc catactttc ctgctgtcct gcaaagctct     540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg ccctgaact tctgggcggt     720 cccagcgtct ttttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac cccccagtg    1200 ctggatagtg acgggtcttt ctttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350
```

<210> SEQ ID NO 74
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Asn Met Tyr Trp Val Arg Gln Met Pro Gly Lys Gly Leu Glu Trp Met
        35                  40                  45

Gly Tyr Ile Asp Pro Tyr Asn Gly Gly Thr Ser Tyr Asn Gln Lys Phe
    50                  55                  60

Lys Gly Lys Ala Thr Leu Thr Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Gly Gly Asn Tyr Glu Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

-continued

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
450

<210> SEQ ID NO 75
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gatatccaac tcacccagtc cccttcatcc ctgtctgcat cagtcgggga cagagtgaca      60
attacttgtt ccgccagctc tagtgtctca tacatgtatt ggtttcagca aaagccagga     120
aaagctccca aaccccctga tctatctgac cagctatctg gcaagcggcg tgccttctcgg     180 ttcagtggat cagggtccgg tacagacttt accctgacta ttagcagtct gcaaccagag     240
```

```
gacttcgcca cttattactg ccaacagtgg agttcatatc ccctgacttt tggcggaggg    300
accaaggtcg agatcaagcg cacagtcgcc gctccctccg tgttcatctt tccaccaagt    360
gatgagcaac tgaagtctgg tactgcttca gtcgtgtgtc tgctgaacaa tttctaccct    420
cgagaagcca aagtccaatg gaaggtagac aacgcactgc agtccggcaa tagccaagaa    480
tcagttaccg aacaggattc aaaggacagt acatattccc tgagcagcac tctgaccctg    540 tcaaggccg attacgagaa acacaaggtc tatgcttgcg aagtgacaca tcagggactg    600
tccagcccag tgacaaaatc ttttaaccgt ggggagtgt                           639
```

<210> SEQ ID NO 76
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Phe Gln Gln Lys Pro Gly Lys Ala Pro Lys Pro Leu Ile Tyr
        35                  40                  45

Leu Thr Ser Tyr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Tyr Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 77
<211> LENGTH: 990
<212> TYPE: DNA
<213> ORGANISM: Homo sapiens

<400> SEQUENCE: 77

```
gcctccacca agggcccatc ggtcttcccc ctggcaccct cctccaagag cacctctggg    60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
```

```
ggactctact ccctcagcag cgtggtgacc gtgccctcca gcagcttggg cacccagacc    240
tacatctgca acgtgaatca caagcccagc aacaccaagg tggacaagag agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa gaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                    990
```

<210> SEQ ID NO 78
<211> LENGTH: 330
<212> TYPE: PRT
<213> ORGANISM: Homo sapiens

<400> SEQUENCE: 78

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
```

```
                225                 230                 235                 240
Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330

<210> SEQ ID NO 79
<211> LENGTH: 321
<212> TYPE: DNA
<213> ORGANISM: Homo sapiens

<400> SEQUENCE: 79
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                                321

<210> SEQ ID NO 80
<211> LENGTH: 107
<212> TYPE: PRT
<213> ORGANISM: Homo sapiens

<400> SEQUENCE: 80

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

-continued

<223> OTHER INFORMATION: Asp or Ser

<400> SEQUENCE: 81

Xaa Tyr Asn Met Tyr
1               5

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Arg or Ser
<220> FEATURE:
<221> NAME/KEY: MOD_RES
<222> LOCATION: (11)..(11)
<223> OTHER INFORMATION: Asp or Tyr
<220> FEATURE:
<221> NAME/KEY: MOD_RES
<222> LOCATION: (13)..(13)
<223> OTHER INFORMATION: Gln or Pro
<220> FEATURE:
<221> NAME/KEY: MOD_RES
<222> LOCATION: (14)..(14)
<223> OTHER INFORMATION: Lys or Ser
<220> FEATURE:
<221> NAME/KEY: MOD_RES
<222> LOCATION: (16)..(16)
<223> OTHER INFORMATION: Lys or Gln

<400> SEQUENCE: 82

Tyr Ile Asp Pro Tyr Asn Gly Gly Thr Xaa Xaa Asn Xaa Xaa Phe Xaa
1               5                   10                  15

Gly

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
<222> LOCATION: (10)..(10)
<223> OTHER INFORMATION: Tyr or His

<400> SEQUENCE: 83

Ser Ala Ser Ser Ser Val Xaa Tyr Met Xaa
1               5                   10

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Asp
<220> FEATURE:
<221> NAME/KEY: MOD_RES
<222> LOCATION: (4)..(4)

<223> OTHER INFORMATION: Asn, Lys or Tyr

<400> SEQUENCE: 84

Xaa Thr Ser Xaa Leu Ala Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Asn
<220> FEATURE:
<221> NAME/KEY: MOD_RES
<222> LOCATION: (6)..(6)
<223> OTHER INFORMATION: Asn or Tyr

<400> SEQUENCE: 85

Gln Gln Trp Xaa Ser Xaa Pro Leu Thr
1               5

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Arg or Ser
<220> FEATURE:
<221> NAME/KEY: MOD_RES
<222> LOCATION: (11)..(11)
<223> OTHER INFORMATION: Asp or Tyr
<220> FEATURE:
<221> NAME/KEY: MOD_RES
<222> LOCATION: (13)..(13)
<223> OTHER INFORMATION: Gln or Pro
<220> FEATURE:
<221> NAME/KEY: MOD_RES
<222> LOCATION: (14)..(14)
<223> OTHER INFORMATION: Lys or Ser
<220> FEATURE:
<221> NAME/KEY: MOD_RES
<222> LOCATION: (16)..(16)
<223> OTHER INFORMATION: Lys or Gln

<400> SEQUENCE: 86

Tyr Ile Asp Pro Tyr Asn Gly Gly Thr Xaa Xaa Asn Xaa Xaa Phe Xaa
1               5                   10                  15

Gly

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asn or Tyr

<400> SEQUENCE: 87

```
Leu Thr Ser Xaa Leu Ala Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asn or Tyr

<400> SEQUENCE: 88

Gln Gln Trp Ser Ser Xaa Pro Leu Thr
1               5

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Ser
<220> FEATURE:
<221> NAME/KEY: MOD_RES
<222> LOCATION: (2)..(2)
<223> OTHER INFORMATION: Gly or Leu
<220> FEATURE:
<221> NAME/KEY: MOD_RES
<222> LOCATION: (4)..(4)
<223> OTHER INFORMATION: Asn or not present
<220> FEATURE:
<221> NAME/KEY: MOD_RES
<222> LOCATION: (5)..(5)
<223> OTHER INFORMATION: Tyr or not present
<220> FEATURE:
<221> NAME/KEY: MOD_RES
<222> LOCATION: (6)..(6)
<223> OTHER INFORMATION: Glu or not present
<220> FEATURE:
<221> NAME/KEY: MOD_RES
<222> LOCATION: (7)..(7)
<223> OTHER INFORMATION: Ala or Pro
<220> FEATURE:
<221> NAME/KEY: MOD_RES
<222> LOCATION: (8)..(8)
<223> OTHER INFORMATION: Trp or Asp
<220> FEATURE:
<221> NAME/KEY: MOD_RES
<222> LOCATION: (10)..(10)
<223> OTHER INFORMATION: Ala or Asp

<400> SEQUENCE: 89

Xaa Xaa Gly Asn Tyr Glu Xaa Xaa Phe Xaa Tyr
1               5                   10
```

FIBROBLAST GROWTH FACTOR RECEPTOR 3 (FGFR3) BINDING PROTEINS

RELATED APPLICATIONS

This application claims the benefit and priority of U.S. Provisional Application No. 61/077,278, filed Jul. 1, 2008, the entire contents of which are incorporated herein by reference.

FIELD OF INVENTION

The field of the invention is molecular biology, immunology and oncology. More particularly, the field is antibody-based binding proteins that bind human fibroblast growth factor receptor 3 (FGFR3).

BACKGROUND

Fibroblast Growth Factor Receptor 3 (FGFR3) is one member of a family of receptor tyrosine kinases (FGFR1, FGFR2, FGFR3, FGFR4) that binds fibroblast growth factors (FGFs) (Keegan et al. (1991) PROC. NATL. ACAD. SCI. USA 88:1095-1099). FGF receptors are characterized as having three extracellular immunoglobulin-like domains, a transmembrane domain, and a cytoplasmic tyrosine kinase domain. FGF ligand binding induces FGF receptor dimerization and tyrosine autophosphorylation resulting in cell proliferation, differentiation, and migration (Gomez-Roman et al. (2005) CLIN. CANCER RES. 11:459-65; Chang et al. (2005) BLOOD 106:353-6; Eswarakumar et al. (2005) CYTOKINE GROWTH FACTOR REV. 16(2): 139-49).

Alternative splicing of the FGFR3 transcript results in two isoforms, IIIb and IIIc. The FGFR3 isoforms are differentially expressed with epithelial cells expressing predominantly the IIIb isoform, whereas fibroblast cells express a mixture of IIIb and IIIc transcripts (Scotet et al. (1995) BIOCHIM. BIOPHYS. ACTA 1264:238-42). In addition, the IIIb and IIIc splice variants differ in their specificity for FGF ligand. The IIIb splice variant has high affinity for FGF1 (acidic FGF) ligand and lower affinity for FGF8 (androgen-induced growth factor) and FGF9 (glial activating factor) (Chellaiah et al. (1999) J. BIOL. CHEM. 274:34785-94; Gomez-Roman et al. (2005) supra). The IIIc splice variant is characterized as a promiscuous receptor binding numerous FGF ligands including FGF1, FGF2, FGF4, FGF8, FGF9, FGF16, FGF17, FGF18, FGF19, FGF20, FGF21, and FGF23 (Chellaiah et al. (1994) J. BIOL. CHEM. 269:11620-7; Gomez-Roman et al. (2005) supra; Ornitz et al. (1996) J. BIOL. CHEM. 271(25): 15292-7; Lee et al. (2000) J. BIOL. CHEM. 275(43):33679-87).

The FGFR3-FGF signaling pathway plays a role in the differentiation of adipocytes, chondrocytes and neurons, wound healing, angiogenesis, embryo development, and malignancies (Keegan et al. (1991) supra). Activating mutations of FGFR3 have been associated with cancer and skeletal disorders including dwarfism, achondroplasia, and hypochondroplasia (Gomez-Roman et al. (2005) supra; Delezoide et al. (1997) HUMAN MOL. GENETICS 6:1899-1906). Certain FGFR3 antibodies are known. See, e.g., U.S. 2005/0147612 (Yayon).

Antibodies are multimeric proteins that contain four polypeptide chains (FIG. 1). Two of the polypeptide chains are called heavy chains (H chains), and two of the polypeptide chains are called light chains (L chains). The immunoglobulin heavy and light chains are connected by an interchain disulfide bond. The immunoglobulin heavy chains are connected by interchain disulfide bonds. A light chain consists of one variable region ($V_L$ in FIG. 1) and one constant region ($C_L$ in FIG. 1). The heavy chain consists of one variable region ($V_H$ in FIG. 1) and at least three constant regions ($CH_1$, $CH_2$ and $CH_3$ in FIG. 1). The variable regions determine the specificity of the antibody.

Each variable region comprises three hypervariable regions also known as complementarity determining regions (CDRs) flanked by four relatively conserved framework regions (FRs). The three CDRs, referred to as $CDR_1$, $CDR_2$, and $CDR_3$, contribute to the antibody binding specificity.

Although certain anti-FGFR3 antibodies are known in the art, there is still a need for additional FGFR3 modulators that can be used as therapeutic and diagnostic agents.

SUMMARY OF THE INVENTION

The invention is based, in part, upon the discovery of a family of binding proteins that specifically bind human FGFR3. The binding proteins contain FGFR3 binding sites based on the CDRs of a family of antibodies that specifically bind FGFR3. The binding proteins can be used as diagnostic and therapeutic agents. When used as a therapeutic agent, the binding proteins are engineered, e.g., humanized, to reduce or eliminate an immune response when administered to a human patient.

The binding proteins prevent or inhibit the activation of (i.e., neutralize) human FGFR3. In some embodiments, the binding proteins prevent FGFR3 from binding to a ligand, e.g., FGF1, thereby neutralizing FGFR3 activation. The binding proteins can be used to inhibit the proliferation of tumor cells or stimulate the proliferation of chondrocytes. Furthermore, when administered to a mammal, the binding proteins can inhibit or reduce tumor growth in the mammal.

These and other aspects and advantages of the invention will become apparent upon consideration of the following figures, detailed description, and claims. As used herein, "including" means without limitation, and examples cited are non-limiting.

DESCRIPTION OF THE DRAWINGS

The invention can be more completely understood with reference to the following drawings.

FIG. 2 is a schematic diagram showing the amino acid sequence of the complete immunoglobulin heavy chain variable region of antibodies 15D8, 27H2, 2G4, 4E7 (7D12), and 20B4. The amino acid sequences for each antibody are aligned against one another, and $CDR_1$, $CDR_2$, and $CDR_3$ are identified in boxes. The unboxed sequences represent framework (FR) sequences.

FIG. 3 is a schematic diagram showing the $CDR_1$, $CDR_2$, and $CDR_3$ sequences for each of the immunoglobulin heavy chain variable region sequences in FIG. 2. For antibody 15D8, three alternative $CDR_2$ sequences are shown (15D8, 15D8-2, and 15D8-3).

FIG. 4 is a schematic diagram showing the amino acid sequence of the complete immunoglobulin light chain variable region of antibodies 15D8, 27H2, 2G4, 4E7 (7D12), and 20B4. The amino acid sequences for each antibody are aligned against one another, and $CDR_1$, $CDR_2$, and $CDR_3$ are identified in boxes. The unboxed sequences represent framework (FR) sequences.

FIG. 5 is a schematic diagram showing the $CDR_1$, $CDR_2$, and $CDR_3$ sequences for each of the immunoglobulin light chain variable region sequences in FIG. 4.

DETAILED DESCRIPTION

Figure 1:
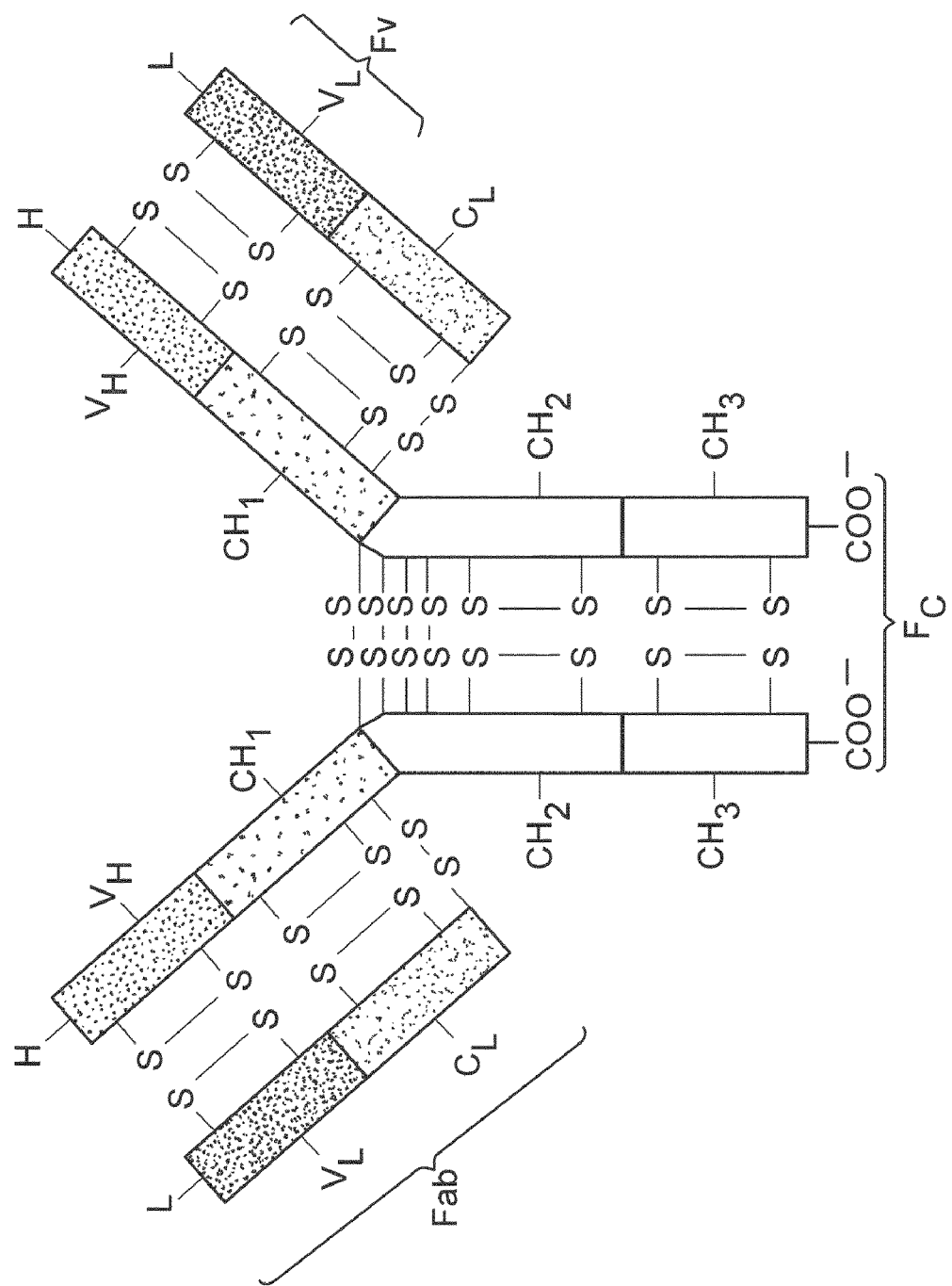
FIG. 1 (prior art) is a schematic representation of a typical antibody.

The invention is based, in part, upon the discovery of a family of binding proteins that specifically bind and neutralize the activity of human FGFR3. The binding proteins can be used in a variety of diagnostic and therapeutic applications. The binding proteins are based upon the antigen binding sites of certain monoclonal antibodies that have been selected for their ability to bind and neutralize the activity of FGFR3. The binding proteins contain immunoglobulin variable region CDR sequences that define a binding site for FGFR3.

In view of the neutralizing activity of these antibodies, they are useful for modulating the growth and/or proliferation of certain cancer cells. When used as a therapeutic agent, the binding proteins can be engineered to minimize or eliminate an immune response when administered to a human patient. In some embodiments of the invention, the binding proteins are fused or conjugated to other moieties, such as detectable labels (e.g., radiolabels) or effector molecules (e.g., other proteins or small molecule therapeutics). Various features and aspects of the invention are discussed in more detail below.

I—Binding Proteins That Bind FGFR3

In certain embodiments of the invention, the binding protein comprises (i) an immunoglobulin heavy chain variable region comprising the structure $CDR_{H1}$-$CDR_{H2}$-$CDR_{H3}$ and (ii) an immunoglobulin light chain variable region comprising three complementarity determining regions (CDRs), wherein the immunoglobulin heavy chain variable region and the immunoglobulin light chain variable region together define a single binding site for binding human FGFR3. $CDR_{H1}$ comprises the amino acid sequence $X_1$ Tyr Asn Met Tyr (SEQ ID NO: 81), wherein amino acid $X_1$ is Asp or Ser. $CDR_{H2}$ comprises the amino acid sequence Tyr Ile Asp Pro Tyr Asn Gly Gly Thr $X_2$ $X_3$ Asn $X_4$ $X_5$ Phe $X_6$ Gly (SEQ ID NO: 82), wherein amino acid $X_2$ is Arg or Ser, amino acid $X_3$ is Asp or Tyr, amino acid $X_4$ is Gln or Pro, amino acid $X_5$ is Lys or Ser, and amino acid $X_6$ is Lys or Gln. $CDR_{H3}$ comprises the amino acid sequence $X_7$ $X_8$ Gly $X_9$ $X_{10}$ $X_{11}$ $X_{12}$ $X_{13}$ Phe $X_{14}$ Tyr (SEQ ID NO: 89), wherein amino acid $X_7$ is Glu or Ser, amino acid $X_8$ is Gly or Leu, amino acid $X_9$ is Asn or a peptide bond, amino acid $X_{10}$ is Tyr or a peptide bond, amino acid $X_{11}$ is Glu or a peptide bond, amino acid $X_{12}$ is Ala or Pro, amino acid $X_{13}$ is Trp or Asp, and amino acid $X_{14}$ is Ala or Asp.

In some embodiments of the invention, the binding protein comprises (i) an immunoglobulin light chain variable region comprising the structure $CDR_{L1}$-$CDR_{L2}$-$CDR_{L3}$ and (ii) an immunoglobulin heavy chain variable region comprising three CDRs, wherein the immunoglobulin heavy chain variable region and the immunoglobulin light chain variable region together define a single binding site for binding human FGFR3. $CDR_{L1}$ comprises the amino acid sequence Ser Ala Ser Ser Ser Val $X_{15}$ Tyr Met $X_{16}$ (SEQ ID NO: 83), wherein amino acid $X_{15}$ is Ser or Asn, and $X_{16}$ is Tyr or His. $CDR_{L2}$ comprises the amino acid sequence $X_{17}$ Thr Ser $X_{18}$ Leu Ala Ser (SEQ ID NO: 84), wherein the amino acid $X_{17}$ is Leu or Asp, and the amino acid $X_{18}$ is Asn, Lys, or Tyr. $CDR_{L3}$ comprises the amino acid sequence Gln Gln Trp $X_{19}$ Ser $X_{20}$ Pro Leu Thr (SEQ ID NO: 85), wherein the amino acid $X_{19}$ is Ser or Asn, and the amino acid $X_{20}$ is Asn or Tyr.

In some embodiments, the binding protein comprises an immunoglobulin heavy chain variable region comprising the structure $CDR_{H1}$-$CDR_{H2}$-$CDR_{H3}$, wherein (i) $CDR_{H1}$ comprises the amino acid sequence Ser Tyr Asn Met Tyr (SEQ ID NO: 17), (ii) $CDR_{H2}$ comprises the amino acid sequence Tyr Ile Asp Pro Tyr Asn Gly Gly Thr $X_1$ $X_2$ Asn $X_3$ $X_4$ Phe $X_5$ Gly (SEQ ID NO: 86), wherein amino acid $X_1$ is Arg or Ser, amino acid $X_2$ is Asp or Tyr, amino acid $X_3$ is Gln or Pro, amino acid $X_4$ is Lys or Ser, and amino acid $X_5$ is Lys or Gln, and (iii) $CDR_{H3}$ comprises the amino acid sequence Glu Gly Gly Asn Tyr Glu Ala Trp Phe Ala Tyr (SEQ ID NO: 19), and an immunoglobulin light chain variable region comprising the structure $CDR_{L1}$-$CDR_{L2}$-$CDR_{L3}$, wherein (i) $CDR_{L1}$ comprises the amino acid sequence Ser Ala Ser Ser Ser Val Ser Tyr Met Tyr (SEQ ID NO: 22), (ii) $CDR_{L2}$ comprises the amino acid sequence Leu Thr Ser $X_6$ Leu Ala Ser (SEQ ID NO: 87), wherein the amino acid $X_6$ is Asn or Tyr, and (iii) $CDR_{L3}$ comprises the amino acid sequence Gln Gln Trp Ser Ser $X_7$ Pro Leu Thr (SEQ ID NO: 88), wherein the amino acid $X_7$ is Asn or Tyr.

The binding protein can comprise both the immunoglobulin light chain and the immunoglobulin heavy chain sequences or the fragments thereof, described above. The binding protein can be an intact antibody or an antigen binding fragment thereof, or a biosynthetic antibody site.

In some embodiments, the CDR sequences of the immunoglobulin light chain and the immunoglobulin heavy chain are interposed with framework regions (FR). The framework regions optionally can be humanized or fully human.

In some embodiments of the invention, the binding protein comprises: (a) an immunoglobulin heavy chain variable region comprising the structure $CDR_{H1}$-$CDR_{H2}$-$CDR_{H3}$ and (b) immunoglobulin light chain variable region, wherein the heavy chain variable region and the light chain variable region together define a single binding site for binding human FGFR3. The $CDR_{H1}$ comprises a sequence selected from the group consisting of SEQ ID NO: 17 (15D8, 27H2, 4E7 (7D12), 2G4) and SEQ ID NO: 29 (20B4). The $CDR_{H2}$ comprises a sequence selected from the group consisting of SEQ ID NO: 18 (15D8, 20B4), SEQ ID NO: 20 (15D8-2), SEQ ID NO: 21 (15D8-3), SEQ ID NO: 25 (27H2, 4E7(7D12)), and SEQ ID NO: 28 (2G4). The $CDR_{H3}$ comprises a sequence selected from the group consisting of SEQ ID NO: 19 (15D8, 27H2, 4E7(7D12), 2G4) and SEQ ID NO: 30 (20B4). Throughout the specification a particular SEQ ID NO. is followed in parentheses by the antibody that was the origin of that sequence. For example, "SEQ ID NO: 29 (20B4)" means SEQ ID NO: 29 comes from antibody 20B4.

In certain embodiments, the binding protein comprises an immunoglobulin heavy chain variable region comprising a $CDR_{H1}$ comprising the sequence of SEQ ID NO: 17 (15D8), a $CDR_{H2}$ comprising an amino acid sequence selected from the group consisting of SEQ ID NO: 18 (15D8), SEQ ID NO: 20 (15D8-2), and SEQ ID NO: 21 (15D8-3), and a $CDR_{H3}$ comprising the sequence of SEQ ID NO: 19 (15D8). In a preferred embodiment, the binding protein comprises an immunoglobulin heavy chain variable region comprising a $CDR_{H1}$ comprising the sequence of SEQ ID NO: 17 (15D8), a $CDR_{H2}$ comprising an amino acid sequence selected from the group consisting of SEQ ID NO: 18 (15D8), and a $CDR_{H3}$ comprising the sequence of SEQ ID NO: 19 (15D8).

In some embodiments, the binding protein comprises an immunoglobulin heavy chain variable region comprising a $CDR_{H1}$ comprising the sequence of SEQ ID NO: 17 (27H2, 4E7(7D12)), a $CDR_{H2}$ comprising an amino acid sequence selected from the group consisting of SEQ ID NO: 25 (27H2, 4E7(7D12)), and a $CDR_{H3}$ comprising the sequence of SEQ ID NO: 19 (27H2, 4E7(7D12)).

In some embodiments, the binding protein comprises an immunoglobulin heavy chain variable region comprising a $CDR_{H1}$ comprising the sequence of SEQ ID NO: 17 (2G4), a $CDR_{H2}$ comprising the sequence of SEQ ID NO: 28 (2G4), and a $CDR_{H3}$ comprising the sequence of SEQ ID NO: 19 (2G4).

In one embodiment, the binding protein comprises an immunoglobulin heavy chain variable region comprising a $CDR_{H1}$ comprising the sequence of SEQ ID NO: 29 (20B4), a $CDR_{H2}$ comprising the sequence of SEQ ID NO: 18 (20B4), and a $CDR_{H3}$ comprising the sequence of SEQ ID NO: 30 (20B4).

Preferably, the $CDR_{H1}$, $CDR_{H2}$, and $CDR_{H3}$ sequences are interposed between human or humanized immunoglobulin FRs. The binding protein can be an intact antibody, an antigen-binding antibody fragment, or a biosynthetic antibody site.

In some embodiments, the binding protein comprises (a) an immunoglobulin light chain variable region comprising the structure $CDR_{L1}$-$CDR_{L2}$-$CDR_{L3}$, and (b) an immunoglobulin heavy chain variable region, wherein the immunoglobulin light chain variable region and the immunoglobulin heavy chain variable region together define a single binding site for binding human FGFR3. The $CDR_{L1}$ comprises a sequence selected from the group consisting of SEQ ID NO: 22 (15D8, 27H2, 2G4, 4E7(7D12)) and SEQ ID NO: 31 (20B4); the $CDR_{L2}$ comprises a sequence selected from the group consisting of SEQ ID NO: 23 (15D8), SEQ ID NO: 26 (27H2, 2G4, 4E7(7D12)), and SEQ ID NO: 32 (20B4); and the $CDR_{L3}$ comprises a sequence selected from the group consisting of SEQ ID NO: 24 (15D8), SEQ ID NO: 27 (27H2, 2G4, 4E7(7D12)), and SEQ ID NO: 33 (20B4).

In some embodiments, the binding protein comprises an immunoglobulin light chain variable region comprising: a $CDR_{L1}$ comprising the sequence of SEQ ID NO: 22 (15D8); a $CDR_{L2}$ comprising an amino acid sequence selected from the group consisting of SEQ ID NO: 23 (15D8); and a $CDR_{L3}$ comprising the sequence of SEQ ID NO: 24 (15D8).

In one embodiment, the binding protein comprises an immunoglobulin light chain variable region comprising: a $CDR_{L1}$ comprising the sequence of SEQ ID NO: 22 (27H2, 2G4, 4E7(7D12)); a $CDR_{L2}$ comprising the sequence of SEQ ID NO: 26 (27H2, 2G4, 4E7(7D12)); and a $CDR_{L3}$ comprising the sequence of SEQ ID NO: 27 (27H2, 2G4, 4E7(7D12)).

In one embodiment, the binding protein comprises an immunoglobulin light chain variable region comprising: a $CDR_{L1}$ comprising the sequence of SEQ ID NO: 31 (20B4); a $CDR_{L2}$ comprising the sequence of SEQ ID NO: 32 (20B4); and a $CDR_{L3}$ comprising the sequence of SEQ ID NO: 33 (20B4).

Preferably, the $CDR_{L1}$, $CDR_{L2}$, and $CDR_{L3}$ sequences are interposed between human or humanized immunoglobulin FRs. The binding protein can be an intact antibody, an antigen-binding antibody fragment, or a biosynthetic antibody site.

In some embodiments of the invention, the binding protein comprises: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding human FGFR3. The $CDR_{H1}$ comprises SEQ ID NO: 17 (15D8, 27H2, 2G4, 4E7(7D12)); a $CDR_{H2}$ is selected from the group consisting of SEQ ID NO: 18 (15D8), SEQ ID NO: 20 (15D8-2), SEQ ID NO: 21 (15D8-3), SEQ ID NO: 25 (27H2, 4E7(7D12)), and SEQ ID NO: 28 (2G4); and the $CDR_{H3}$ comprises SEQ ID NO: 19 (15D8, 27H2, 2G4, 4E7(7D12)). The $CDR_{L1}$ comprises SEQ ID NO: 22 (15D8, 27H2, 2G4, 4E7(7D12)); a $CDR_{L2}$ is selected from the group consisting SEQ ID NO: 23 (15D8) and SEQ ID NO: 26 (27H2, 2G4, 4E7(7D12)); and a $CDR_{L3}$ is selected from the group consisting SEQ ID NO: 24 (15D8) and SEQ ID NO: 27 (27H2, 2G4, 4E7(7D12)).

In another embodiment, the binding protein comprises an immunoglobulin heavy chain variable region selected from the group consisting of SEQ ID NO: 2 (15D8), SEQ ID NO: 6 (27H2), SEQ ID NO: 10 (2G4), SEQ ID NO: 12 (4E7 (7D12)), and SEQ ID NO: 14 (20B4), and an immunoglobulin light chain variable region selected from the group consisting of SEQ ID NO: 4 (15D8), SEQ ID NO: 8 (27H2, 2G4, 4E7(7D12)), and SEQ ID NO: 16 (20B4).

In another embodiment, the binding protein comprises an immunoglobulin heavy chain variable region comprising SEQ ID NO: 2 (15D8), and an immunoglobulin light chain variable region comprising SEQ ID NO: 4 (15D8).

In another embodiment, the binding protein comprises an immunoglobulin heavy chain variable region comprising SEQ ID NO: 6 (27H2), and an immunoglobulin light chain variable region comprising SEQ ID NO: 8 (27H2).

In another embodiment, the binding protein comprises an immunoglobulin heavy chain variable region comprising SEQ ID NO: 10 (2G4), and an immunoglobulin light chain variable region comprising SEQ ID NO: 8 (2G4).

In another embodiment, the binding protein comprises an immunoglobulin heavy chain variable region comprising SEQ ID NO: 12 (4E7(7D12)), and an immunoglobulin light chain variable region comprising SEQ ID NO: 8 (4E7 (7D12)).

In another embodiment, the binding protein comprises an immunoglobulin heavy chain variable region comprising SEQ ID NO: 14 (20B4), and an immunoglobulin light chain variable region comprising SEQ ID NO: 16 (20B4).

In each of the foregoing embodiments, the binding protein can be an intact antibody, an antigen-binding antibody fragment, or a biosynthetic antibody site.

In other embodiments, the binding protein comprises (i) an immunoglobulin heavy chain selected from the group consisting of SEQ ID NO: 39 (15D8), SEQ ID NO: 43 (27H2), SEQ ID NO: 47 (2G4), SEQ ID NO: 51 (4E7(7D12)), and SEQ ID NO: 55 (20B4), and (ii) an immunoglobulin light chain selected from the group consisting of SEQ ID NO: 41 (15D8), SEQ ID NO: 45 (27H2), SEQ ID NO: 49 (2G4), SEQ ID NO: 53 (4E7(7D12)) and SEQ ID NO: 57 (20B4).

In another embodiment, the binding protein comprises an immunoglobulin heavy chain comprising SEQ ID NO: 39 (15D8), and an immunoglobulin light chain comprising SEQ ID NO: 41 (15D8).

In another embodiment, the binding protein comprises an immunoglobulin heavy chain comprising SEQ ID NO: 43 (27H2), and an immunoglobulin light chain comprising SEQ ID NO: 45 (27H2).

In another embodiment, the binding protein comprises an immunoglobulin heavy chain comprising SEQ ID NO: 47 (2G4), and an immunoglobulin light chain comprising SEQ ID NO: 49 (2G4).

In another embodiment, the binding protein comprises an immunoglobulin heavy chain comprising SEQ ID NO: 51 (4E7(7D12)), and an immunoglobulin light chain comprising SEQ ID NO: 53 (4E7(7D12)).

In another embodiment, the binding protein comprises an immunoglobulin heavy chain comprising SEQ ID NO: 55 (20B4), and an immunoglobulin light chain comprising SEQ ID NO: 57 (20B4).

Each of the binding proteins described above can be an intact antibody, e.g., a monoclonal antibody. Alternatively, the binding protein can be an antigen binding fragment of an antibody, or can be a biosynthetic antibody binding site. Antibody fragments include Fab, Fab', (Fab')$_2$ and Fv fragments. Techniques for making antibody fragments are known in the art. Biosynthetic antibody binding sites are known in the art, e.g., single Fv and sFv molecules. See, e.g., U.S. Pat. No. 5,476,786. Other biosynthetic antibody binding sites include bispecific or bifunctional binding proteins, e.g., antibodies or antibody fragments that bind at least two different antigens. For example, bispecific binding proteins can bind human FGFR3 and another antigen of interest. Methods for making bispecific antibodies are known in art. Such methods include fusing hybridomas or by linking Fab' fragments. See, e.g., Songsivilai et al. (1990) CLIN. EXP. IMMUNOL. 79: 315-325; Kostelny et al. (1992) J. IMMUNOL. 148: 1547-1553.

In some embodiments of the invention, an isolated binding protein binds human FGFR3 with a $K_D$ of 10 nM, 5 nM, 4 nM, 3 nM, 2 nM, or lower, wherein the $K_D$ values are determined by surface plasmon resonance methods under the conditions described in Example 3.

In some embodiments of the invention, an isolated binding protein binds human FGFR3 with a $K_D$ of 200 pM, 150 pM, 100 pM, 90 pM, 80 pM, 70 pM, 60 pM, 50 pM, 40 pM, 30 pM, 20 pM, 10 pM, or lower, wherein the $K_D$ values are determined by a kinetic exclusion assay (See, e.g., Darling and Brault (2004) ASSAY AND DRUG DEVELOPMENT TECHNOLOGIES 2: 647-657) under the conditions described in Example 7.

In some embodiments, the binding proteins inhibit hFGFR3 from binding to FGF1. For example, the binding proteins can have an $IC_{50}$ (concentration at 50% of maximum inhibition) of about 10, 11, 12, 13, 14, 15, 16, 17 or 18 nM, when assayed using the protocol described in Example 4.

II—Production of Binding Proteins

Methods for producing binding proteins of the invention are known in the art. For example, DNA molecules encoding light chain variable regions and heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired binding proteins. Production of defined gene constructs is within routine skill in the art. Alternatively, the sequences provided herein can be cloned out of hybridomas by conventional hybridization techniques or PCR techniques, using synthetic nucleic acid probes whose sequences are based on sequence information provided herein or prior art sequence information regarding genes encoding the heavy and light chains of murine antibodies in hybridoma cells.

The nucleic acids encoding the desired binding proteins can be introduced (ligated) into expression vectors, which can be introduced into a host cell through conventional transfection or transformation techniques. Exemplary host cells include E. coli cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce immunoglobulin protein. Transfected host cells are grown under conditions that permit the host cells to express the genes of interest, e.g., genes that encode the immunoglobulin light or heavy chain variable regions.

Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a signal sequence, e.g., a sequence encoding fragment B of protein A (FB). The expressed fusion protein accumulates in refractile or inclusion bodies in the bacterial cytoplasm, and may be harvested after disruption of the cells by French press or sonication. The refractile bodies then are solubilized, and the proteins refolded and cleaved by methods already established for other recombinant proteins.

If the engineered gene is to be expressed in eukaryotic host cells, e.g., myeloma cells or CHO cells, it is first inserted into an expression vector containing a suitable eukaryotic promoter, a secretion signal, immunoglobulin enhancers, and various introns. This expression vector optionally contains sequences encoding all or part of a constant region, enabling an entire, or a part of, a heavy or light chain to be expressed. The gene construct can be transfected into myeloma cells or CHO cells using established transfection protocols. Such transfected cells can express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a protein domain having another function (e.g., cytotoxicity).

III—Modifications to the Binding Proteins

The binding proteins can be modified to optimize performance, depending upon the intended use of the binding proteins. For example, when the binding protein is being used as a therapeutic agent, the binding protein can be modified to reduce its immunogenicity in a human patient. Alternatively or in addition, the binding protein can be fused or chemically conjugated to another protein or peptide, e.g., a growth factor, cytokine, or cytotoxin.

Various techniques for reducing or eliminating the antigenicity of antibodies and antibody fragments are known in the art. When the binding proteins are to be administered to a human, the binding proteins preferably are engineered ("humanized") to reduce or eliminate antigenicity in humans. Preferably, the humanized binding proteins have the same or substantially the same affinity for the antigen as the original non-humanized binding protein from which it was derived.

In one humanization approach, chimeric proteins are created in which mouse immunoglobulin constant regions are replaced with human immunoglobulin constant regions. See, e.g., Morrison, et al. (1984) PROC. NAT. ACAD. SCI. 81: 6851-6855, Neuberger et al. (1984) NATURE 312: 604-608; U.S. Pat. No. 6,893,625 (Robinson); U.S. Pat. No. 5,500,362 (Robinson); and U.S. Pat. No. 4,816,567 (Cabilly).

In another approach, known as CDR grafting, the CDRs of the light and heavy chain variable regions are grafted into frameworks from another species. For example, murine CDRs can be grafted into human FR sequences. In some embodiments of the invention, the CDRs of the light and heavy chain variable regions of an anti-FGFR3 antibody are grafted into human FRs or consensus human FRs. In order to create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In an approach called "superhumanization," human immunogenicity is reduced or eliminated by an alternative form of grafting. In superhumanization, human CDR sequences are chosen from a set of human germline genes based on the structural similarity of the human CDRs to those of the mouse antibody to be humanized. See, e.g., U.S. Pat. No. 6,881,557 (Foote); and Tan et al. (2002) J. IMMUNOL 169:1119-1125.

Other methods to reduce immunogenicity include "reshaping," "hyperchimerization," and veneering/resurfacing." See, e.g., Vaswami et al. (1998) ANNALS OF ALLERGY, ASTHMA, & IMMUNOL. 81: 105; Roguska et al. (1996) PROT. ENGINEER 9: 895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of immunoglobulin heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another approach for modifying a mouse antibody into a form suitable for medical use in humans is HUMAN ENGINEERING™ (HE™) technology, which is practiced commercially by XOMA (US) LLC. See, e.g., International Application Publication No. WO 93/11794 and U.S. Pat. Nos. 5,766,886; 5,770,196; 5,821,123; and 5,869,619.

Any suitable approach, including any of the above approaches, can be used to reduce or eliminate human immunogenicity of a binding protein of the invention.

Binding proteins of the invention can be conjugated to, or fused with, other molecules, depending upon their intended use. For example, if the binding protein is going to be used as a therapeutic, then the binding protein can be conjugated with another agent, for example, an effector molecule that modulates or otherwise promotes the therapy. A small molecule drug, a radiolabel or toxin, then, the agent can be chemically coupled to the binding protein using standard in vitro coupling chemistries. If the effector molecule is a protein or peptide, the binding protein can be chemically coupled to the effector using in vitro coupling chemistries or can be coupled to the effector as a fusion protein. Fusion proteins can be constructed and expressed using the techniques similar to those discussed in section II.

IV—Use of Binding Proteins

Binding proteins of the invention can be used as a research agent, diagnostic agent or therapeutic agent.

(1) Therapeutic Applications

Because the binding proteins of the invention prevent or inhibit the activation of FGFR3, they can be used in therapeutic applications. For example, certain binding proteins of the invention are useful in the prevention or treatment of hyperproliferative diseases or disorders, e.g., various forms of cancer and skeletal disorders.

The binding proteins can be used to inhibit or reduce the proliferation of cancer cells. In such an approach, the cancer cells are exposed to a therapeutically effective amount of the binding protein so as to inhibit or reduce proliferation of the cancer cell. In some embodiments, the binding proteins inhibit cancer cell proliferation by at least 50%, 60%, 70%, 80%, 90%, or 95%.

In some embodiments, the binding protein is used to inhibit or reduce proliferation of a tumor cell wherein the binding protein inhibits binding of hFGFR3 to an FGF ligand, e.g., FGF1.

The binding protein can be used in a method to inhibit tumor growth in a mammal, e.g., a human patient. The method comprises administering to the mammal a therapeutically effective amount of the binding protein.

Cancers associated with FGFR3 activation include bladder cancer, cervical cancer, oral squamous cell cancer, non-small cell lung cancer, breast cancer, lymphoma, and multiple myeloma.

Exemplary skeletal disorders that are associated with FGFR3 activation include achondroplasia, hypochondroplasia, dwarfism, thanatophoric dysplasia (TD) (clinical forms TD I and TD II), and craniosynostosis syndromes.

As used herein, "treat, "treating" and "treatment" mean the treatment of a disease in a mammal, e.g., in a human. This includes: (a) inhibiting the disease, i.e., arresting its development; (b) relieving the disease, i.e., causing regression of the disease state; and (c) curing the disease.

Generally, a therapeutically effective amount of active component will be in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the binding protein, the pharmaceutical formulation, and the route of administration. The initial dosage may be increased beyond the upper level in order to rapidly achieve the desired blood-level or tissue level. Alternatively, the initial dosage may be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount and the disease being treated. Exemplary dosing frequencies are once per day, once per week and once every two weeks. A preferred route of administration is parenteral, e.g., intravenous infusion. Formulation of monoclonal antibody-based drugs is within ordinary skill in the art. In some embodiments of the invention, the binding protein, e.g., monoclonal antibody, is lyophilized and reconstituted in buffered saline at the time of administration.

The binding proteins may be administered either alone or in combination with other pharmaceutically active ingredients, e.g., a chemotherapeutic drug. The other active ingredients, e.g., immunomodulators, can be administered together with the binding protein, before or after the binding protein.

For therapeutic use, the binding proteins preferably are combined with a pharmaceutically acceptable carrier. As used herein, "pharmaceutically acceptable carrier" means buffers, carriers, and excipients, that are suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing binding proteins of the invention can be presented in a dosage unit form and can be prepared by any suitable method. A pharmaceutical composition should be formulated to be compatible with its intended route of administration. Examples of routes of administration are intravenous (IV), intradermal, inhalation, transdermal (topical), transmucosal, and rectal administration. A preferred route of administration for monoclonal antibodies is IV infusion. Useful formulations can be prepared by any of the methods well known in the pharmaceutical art, described, for example, in *Remington's Pharmaceutical Sciences*, 18th ed. (Mack Publishing Company, 1990).

Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene-diamine-tetra-acetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

In general, pharmaceutical compositions suitable for injection include aqueous solutions (where water soluble) or dispersions and powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished, for example, by filtration through sterile filtration membranes. Where the composition is lyophilized, sterilization using this method can be conducted prior to or following lyophilization and reconstitution. Once the pharmaceutical composition has been formulated, it can be stored, for example, in vials as a solution, suspension, gel, emulsion, solid, or as a dehydrated or lyophilized powder.

(2) Diagnostic Applications

When the binding proteins are used for diagnostic purposes, either in vitro or in vivo, the binding proteins typically are labeled either directly or indirectly with a detectable moiety. The detectable moiety can be any moiety that produces, either directly or indirectly, a detectable signal. The detectable moiety can be a radioisotope, e.g., $^3H$, $^{14}C$, $^{32}P$, $^{35}S$, $^{125}I$ or $^{131}I$; a fluorescent or chemiluminescent compound, e.g., fluorescein isothiocyanate, rhodamine, or luciferin; an enzyme, e.g., alkaline phosphatase, beta-galactosidase, or horseradish peroxidase; a spin label; or a colored particle, e.g., a latex particle or gold particle. The binding protein can be conjugated to the detectable moiety by any suitable method. See, e.g., Hunter et al. (1962) NATURE 144: 945; David et al. (1974) BIOCHEMISTRY 13:1014; Pain et al. (1981) J. IMMUNOL. METH. 40: 219; and Nygren (1982) J. HISTOCHEM. AND CYTOCHEM. 30: 407.

The binding proteins can be employed in immunoassay techniques. Exemplary immunoassays include sandwich immunoassays, competitive immunoassays, and immunohistochemical procedures.

In a sandwich immunoassay, two antibodies that bind an analyte or antigen of interest are used, e.g., one immobilized onto a solid support, and one free in solution and labeled with a detectable moiety. When a sample containing the antigen is introduced into this system, the antigen binds to both the immobilized antibody and the labeled antibody, to form a "sandwich" immune complex on the surface of the support. The complexed protein is detected by washing away non-bound sample components and excess labeled antibody, and measuring the amount of labeled antibody complexed to protein on the support's surface. Alternatively, the antibody free in solution can be detected by a third antibody labeled with a detectable moiety which binds the free antibody. See, e.g., Butt, ed., (1984) PRACTICAL IMMUNOLOGY, Marcel Dekker, New York; Harlow et al. eds. (1988) ANTIBODIES, A LABORATORY APPROACH, Cold Spring Harbor Laboratory; and Diamandis et al., eds. (1996) IMMUNOASSAY, Academic Press, Boston.

Labeled binding proteins are useful as in vivo imaging agents, whereby the binding proteins can target the imaging agents to tissues of interest. An exemplary remotely detectable moiety for in vivo imaging is the radioactive atom Technetium$^{-99m}$ ($^{99m}Tc$), a gamma emitter with a half-life of about six hours. Non-radioactive moieties useful in in vivo imaging include nitroxide spin labels, lanthanide and transition metal ions, all of which induce proton relaxation in situ. In addition to immunoimaging, the complexed radioactive moieties may be used in radioimmunotherapy protocols to destroy the targeted cell. Suitable isotopes for radioimmunotherapy include the radioactive atoms $^{90}Y$t, $^{131}I$ and $^{111}In$.

EXAMPLES

The following Examples are merely illustrative and are not intended to limit the scope or content of the invention in any way.

Example 1

Production of Anti-hFGFR3 Monoclonal Antibodies

This Example describes the production of a number of anti-hFGFR3 monoclonal antibodies.

Immunizations, fusions, and primary screens were conducted at Maine Biotechnology Services Inc. following the Repetitive Immunization Multiple Sites (RIMMS) protocol. Five AJ mice and five Balb/c mice were immunized with recombinant human FGFR3 IIIb (R&D Systems, Catalog No. 1264-FR-050) and FGFR3 IIIc (R&D Systems, Catalog No. 766-FR-050) where the Fc fragment was removed from each by Factor Xa protease cleavage. Two Balb/c mice with sera displaying highest anti-FGFR3 activity by Enzyme Linked Immunosorbent Assay (ELISA) were chosen for subsequent fusion. Spleens and lymph nodes from the appropriate mice were harvested. B-cells then were harvested and fused with a myeloma line. Fusion products were serially diluted onto forty 96-well plates to near clonality. Three thousand seven hundred and sixty-three supernatants from the resulting fusions were screened for their binding to recombinant human FGFR3 IIIb and IIIc by ELISA. Three hundred fifty-six supernatants identified to contain antibodies to FGFR3 were further characterized by in vitro biochemical and cell-based assays as discussed in the following examples. A panel of hybridomas was selected and the hybridomas were sub-cloned and expanded. Hybridoma cell lines were transferred to BioXCell (formerly Bio-Express) for antibody expression and purification by affinity chromatography on Protein G resin under standard conditions.

Example 2

Sequence Analysis of Anti-hFGFR3 Monoclonal Antibodies

This Example describes isotype and sequence analysis of the anti-FGFR3 monoclonal antibodies produced in Example 1.

a. Determination of FGFR3 Murine Monoclonal Antibody Isotypes

The light-chain isotype and heavy chain isotype of each monoclonal antibody was determined using the IsoStrip Mouse Monoclonal Antibody Isotyping Kit according the manufacturer's instructions (Roche Applied Science).

All antibodies were determined to be Kappa immunoglobulin light chain and IgG1 immunoglobulin heavy chain.

b. Determination of Nucleotide Sequences Encoding Immunoglobulin Heavy and Light Chain Variable Regions The heavy and light chain variable regions of the mouse monoclonal antibodies were sequenced using 5' RACE. Total RNA was extracted from each monoclonal hybridoma cells line using the RNeasy Miniprep kit according to the manufacturer's instructions (Qiagen). Full-length first strand cDNA containing 5' ends was generated using the GeneRacer™ Kit according to the manufacturer's instructions (Invitrogen) using random primers for the purpose of 5' RACE (Rapid Amplification of cDNA Ends).

The variable regions of the Kappa and Heavy (IgG1) immunoglobulin chains were amplified by PCR (Polymerase Chain Reaction) using the Expand High-Fidelity PCR System (Roche Applied Science) according the manufacturer's instructions. Heavy chain variable regions were amplified with the GeneRacer™ 5' Primer, 5'-cgactggagcacgagga-cactga-3' (SEQ ID NO: 58) (Invitrogen), and a 3' IgG1 Constant Region specific primer, either 5' tatgcaaggcttacaaccaca 3' (SEQ ID NO: 59) or 5' gccagtggatagacagatgggggtgtcg 3' (SEQ ID NO: 60). Kappa chain variable regions were amplified with the GeneRacer™ 5' Primer and a 3' Kappa Constant Region specific primer, either 5' ctcattcctgttgaagctcttgacaat 3' (SEQ ID NO: 61) or 5' cgactgaggcacctccagatgtt 3' (SEQ ID NO: 62).

Individual PCR products were isolated by agarose gel electrophoresis and purified using the Qiaquick Gel Purification kit according to the manufacturer's instructions (Qiagen). The PCR products were subsequently cloned into the pCR2.1 TOPO plasmid using the topoisomerase based cloning kit TOPO TA Cloning® Kit (with pCR®2.1-TOPO® vector) according to the manufacturer's instructions (Invitrogen) and transformed into DH5-alpha bacteria through standard molecular biology techniques. Plasmid DNA isolated from transformed bacterial clones was sequenced using M13 Forward (5' GTAAAACGACGGCCAGT 3') (SEQ ID NO: 63) and M13 Reverse primers (5' CAGGAAACAGCTATGACC 3') (SEQ ID NO: 64) by Agencourt Bioscience using standard dideoxy DNA sequencing methods to identify the sequence of the variable region sequences. The sequences were analyzed using Vector NTI software (Invitrogen) and the IMGT/V-Quest web server to identify and confirm variable region sequences.

The nucleic acid sequences encoding and the protein sequences defining each of the immunoglobulin heavy chain and light chain variable regions are summarized below (amino terminal signal peptide sequences are not shown). CDR sequences are shown in bold and are underlined in the amino acid sequences.

```
Nucleic Acid Sequence Encoding the 15D8 Heavy Chain Variable Region
                                                              (SEQ ID NO: 1)
   1 gagatccagc tgcagcagtc tggacctgag ctggtgaagc ctggggcttc agtgaaggta 61 tcctgcaagg cttctggtta tgcattcact agctacaaca tgtactgggt gaagcagagc 121 catggaaaga gccttgagtg gattggatat attgatcctt acaatggtgg tactagctac 181 aaccagaagt tcaagggcaa ggccacattg actgttgaca gtcctccag cacagcctac 241 atgcatctca acagcctgac atctgaggac tctgcagtct attactgtgc aagagaggg 301 ggtaactacg aggcctggtt tgcttactgg ggccaaggga ctctggtcac tgtctctgca Protein Sequence Defining the 15D8 Heavy Chain Variable Region
                                                              (SEQ ID NO: 2)
   1 eiqlqqsgpe lvkpgasvkv sckasgyaft synmywvkqs hgkslewigy idpynggtsy

61 ngkfkgkatl tvdkssstay mhlnsltsed savyycareg gnyeawfayw gqgtlvtvsa
```

Nucleic Acid Sequence Encoding the 15D8 Kappa Chain Variable Region
(SEQ ID NO: 3)
```
  1 caaattgttc tcacccagtc tccagcactc atgtctgcat ctccagggga gaaggtcacc 61 atgacctgca gtgccagctc aagtgtaagt tacatgtact ggtaccagca gaagccaaga 121 tcctccccca aaccctggat ttatctcaca tcctacctgg cttctggagt ccctgctcgc 181 ttcagtggca gtggatctgg gacctcttac tctctcacaa tcagcagcat ggaggctgaa 241 gatgctgcca cttattactg ccagcagtgg agtagttacc cgctcacgtt cggtgctgga 301 accaagctgg agctgaaa
```

Protein Sequence Defining the 15D8 Kappa Chain Variable Region
(SEQ ID NO: 4)
```
  1 qivltqspal msaspgekvt mtcsasssvs ymywyqqkpr sspkpwiylt sylasgvpar 61 fsgsgsgtsy sltissmeae daatyycqqw ssypltfgag tklelk
```

Nucleic Acid Sequence Encoding the 27H2 Heavy Chain Variable Region
(SEQ ID NO: 5)
```
  1 gagatccagc tgcagcagtc tggacctgag ctggtgaagc ctggggcttc agtgaaggta 61 tcctgcaagg cttctggtta tgcattcact agctacaaca tgtactggqq gaagcagagc 121 catggaaaga gccttgagtg gattggatat attgatcctt acaatggtgg tactaggtac 181 aaccagaagt tcaagggcaa ggccacaatg actgttgaca gtcctccag cacagcctac 241 atgcatctca acagcctgac atctgaggac tctgcagtct attactgtgc aagagagggg 301 ggtaactacg aggcctggtt tgcttactgg ggccaaggga ctctggtcac tgtctctgca
```

Protein Sequence Defining the 27H2 Heavy Chain Variable Region
(SEQ ID NO: 6)
```
  1 eiqlqqsgpe lvkpgasvkv sckasgyaft synmywvkqs hgkslewigy idpynggtry 61 ngkfkgkatm tvdkssstay mhlnsltsed savyycareg gnyeawfayw gqgtlvtvsa
```

Nucleic Acid Sequence Encoding the 27H2 Kappa Chain Variable Region
(SEQ ID NO: 7)
```
  1 caaattgttc tcacccagtc tccagcactc atgtctgcat ctccagggga gaaggtcacc 61 atgacctgca gtgccagctc aagtgtaagt tacatgtact ggtaccagca gaagccaaga 121 tcctccccca aaccctggat ttatctcaca tccaacctgg cttctggagt ccctgctcgc 181 ttcagtggca gtgggtctgg gacctcttac tctctcacaa tcagcagcat ggaggctgaa 241 gatgctgcca cttattactg ccagcagtgg agtagtaacc cgctcacgtt cggtgctggg 301 accaagctgg agctgaaa
```

Protein Sequence Defining the 27H2 Kappa Chain Variable Region
(SEQ ID NO: 8)
```
  1 qivltqspal msaspgekvt mtcsasssvs ymywyqqkpr sspkpwiylt snlasgvpar 61 fsgsgsgtsy sltissmeae daatyycqqw ssnpltfgag tklelk
```

Nucleic Acid Sequence Encoding the 2G4 Heavy Chain Variable Region
(SEQ ID NO: 9)
```
  1 gagatccagc tgcagcagtc tggacctgag ctggtgaagc ctggggcttc agtgaaggta 61 tcctgcaagg cttctggtta tgcattcaca agctacaaca tgtactgggg gaagcagagc 121 catggaaaga gccttgagtg gattggatat attgatcctt acaatggtgg tactagggac 181 aaccagaagt tcaagggcaa ggccacattg actgttgaca gtcctccag tacagcctac 241 atgcatctca acagcctgac atctgaggac tctgcagtct attactgtgc aagagagggg 301 ggtaactacg aggcctggtt tgcttactgg ggccaaggga ctctggtcac tgtctctgca
```

Protein Sequence Defining the 2G4 Heavy Chain Variable Region
(SEQ ID NO: 10)
```
  1 eiqlqqsgpe lvkpgasvkv sckasgyaft synmywvkqs hgkslewigy idpynggtrd 61 ngkfkgkatl tvdkssstay mhlnsltsed savyycareg gnyeawfayw gqgtlvtvsa
```

Nucleic Acid Sequence Encoding the 2G4 Kappa Chain Variable Region
(SEQ ID NO: 7)

```
  1 caaattgttc tcacccagtc tccagcactc atgtctgcat ctccagggga gaaggtcacc 61 atgacctgca gtgccagctc aagtgtaagt tacatgtact ggtaccagca gaagccaaga 121 tcctccccca aaccctggat ttatctcaca tccaacctgg cttctggagt ccctgctcgc 181 ttcagtggca gtgggtctgg gacctcttac tctctcacaa tcagcagcat ggaggctgaa 241 gatgctgcca cttattactg ccagcagtgg agtagtaacc cgctcacgtt cggtgctggg 301 accaagctgg agctgaaa
```

Protein Sequence Defining the 2G4 Kappa Chain Variable Region
(SEQ ID NO: 8)

```
  1 qivltqspal msaspgekvt mtcsasssvs ymywyqqkpr sspkpwiylt snlasgvpar 61 fsgsgsgtsy sltissmeae daatyycqqw ssnpltfgag tklelk
```

Nucleic Acid Sequence Encoding the 4E7 (7D12) Heavy Chain Variable Region
(SEQ ID NO: 11)

```
  1 gagatccagc tgcagcagtc tggacctgag ctggtgaagc ctggggcttc agtgaaggta 61 tcctgcaagg cttctggtta tgcattcact agctacaaca tgtactgggt gaagcagagc 121 catggaaaga gccttgagtg gattggatat attgatcctt acaatggtgg tactaggtac 181 aaccagaagt tcaagggcaa ggccacattg actgttgaca gtcctccag cacagcctac 241 atgcatctca acagcctgac atctgaggac tctgcagtct attactgtgc aagagaggg 301 ggtaactacg aggcctggtt tgcttactgg ggccaaggga ctctggtcac tgtctctgca
```

Protein Sequence Defining the 4E7 (7D12) Heavy Chain Variable Region
(SEQ ID NO: 12)

```
  1 eiqlqqsgpe lvkpgasvkv sckasgyaft synmywvkqs hgkslewigy idpynggtry

61 ngkfkgkatl tvdkssstay mhlnsltsed savyycareg gnyeawfayw gqgtlvtvsa
```

Nucleic Acid Sequence Encoding the 4E7 (7D12) Kappa Chain Variable Region
(SEQ ID NO: 7)

```
  1 caaattgttc tcacccagtc tccagcactc atgtctgcat ctccagggga gaaggtcacc 61 atgacctgca gtgccagctc aagtgtaagt tacatgtact ggtaccagca gaagccaaga 121 tcctccccca aaccctggat ttatctcaca tccaacctgg cttctggagt ccctgctcgc 181 ttcagtggca gtgggtctgg gacctcttac tctctcacaa tcagcagcat ggaggctgaa 241 gatgctgcca cttattactg ccagcagtgg agtagtaacc cgctcacgtt cggtgctggg 301 accaagctgg agctgaaa
```

Protein Sequence Defining the 4E7 (7D12) Kappa Chain Variable Region
(SEQ ID NO: 8)

```
  1 qivltqspal msaspgekvt mtcsasssvs ymywyqqkpr sspkpwiylt snlasgvpar 61 fsgsgsgtsy sltissmeae daatyycqqw ssnpltfgag tklelk
```

Nucleic Acid Sequence Encoding the 20B4 Heavy Chain Variable Region
(SEQ ID NO: 13)

```
  1 gagatccagc tgcagcagtc tggacctgag ctggtgaagc ctggggcttc agtgaaggta 61 tcctgcaagg cttctggtta ctcactcact gactacaaca tgtactgggt gaagcagagc 121 catggaaaga gccttgagtg gattggatat attgatcctt acaatggtgg tactagctac 181 aaccagaagt tcaagggcaa ggccacattg actgttgaca gtcctccag cacagcctt c 241 atgcatctca acagcctgac atctgaggac tctgcagtct attactgtgc aagatcgttg 301 ggacctgatt ttgactactg gggccaaggc accactctca cagtctcctc a
```

Protein Sequence Defining the 20B4 Heavy Chain Variable Region
(SEQ ID NO: 14)

```
  1 eiqlqqsgpe lvkpgasvkv sckasgyslt dynmywvkqs hgkslewigy idpynggtsy
 61 ngkfkgkatl tvdkssstaf mhlnsltsed savyycarsl gpdfdywgqg ttltvss
```

Nucleic Acid Sequence Encoding the 20B4 Kappa Chain Variable Region
(SEQ ID NO: 15)

```
  1 caaattgttc tcacccagtc tccagcaatc atgtctgcat ctccagggga agggtcacc
 61 atgacctgca gtgccagctc aagtgtaaat tacatgcact ggtaccagca gaagtcaggc
121 acctccccca aagatggat ttatgacaca tccaaactgg cttctggagt ccctgctcgc
181 ttcagtggca gtgggtctgg gacctcttac tctctcacaa tcagcagcat ggaggctgaa
241 gatactgcca cttattactg tcaacagtgg aatagtaacc cactcacgtt cggtgcgggg
301 accaagctgg agctgaaa
```

Protein Sequence Defining the 20B4 Kappa Chain Variable Region
(SEQ ID NO: 16)

```
  1 qivltqspai msaspgekvt mtcsasssvn ymhwyqqksg tspkrwiydt sklasgvpar
 61 fsgsgsgtsy sltissmeae dtatyycqqw nsnpltfgag tklelk
```

Nucleic Acid Sequence Encoding the Murine IgG1 Heavy Chain Constant
Region Determined for 15D8, 20B4, 27H2, 2G4, and 4E7 (7D12)
(SEQ ID NO: 34)

```
  1 gccaaaacga cacccccatc tgtctatcca ctggcccctg gatctgctgc ccaaactaac
 61 tccatggtga ccctgggatg cctggtcaag ggctatttcc ctgagccagt gacagtgacc
121 tggaactctg gatccctgtc cagcggtgtg cacaccttcc cagctgtcct gcagtctgac
181 ctctacactc tgagcagctc agtgactgtc ccctccagca cctggcccag cgagaccgtc
241 acctgcaacg ttgccccacc ggccagcagc accaaggtgg acaagaaaat tgtgcccagg
301 gattgtggtt gtaagccttg catatgtaca gtcccagaag tatcatctgt cttcatcttc
361 cccccaaagc caaggatgt gctcaccatt actctgactc taaggtcac gtgtgttgtg
421 gtagacatca gcaaggatga tcccgaggtc cagttcagct ggtttgtaga tgatgtggag
481 gtgcacacag ctcagacgca accccgggag gagcagttca acagcacttt ccgctcagtc
541 agtgaacttc ccatcatgca ccaggactgg ctcaatggca aggagttcaa atgcagggtc
601 aacagtgcag ctttccctgc ccccatcgag aaaaccatct ccaaaaccaa aggcagaccg
661 aaggctccac aggtgtacac cattccacct cccaaggagc agatggccaa ggataaagtc
721 agtctgacct gcatgataac agacttcttc cctgaagaca ttactgtgga gtggcagtgg
781 aatgggcagc cagcggagaa ctacaagaac actcagccca tcatggacac agatggctct
841 tacttcgtct acagcaagct caatgtgcag aagagcaact gggaggcagg aaatactttc
901 acctgctctg tgttacatga gggcctgcac aaccaccata ctgagaagag cctctcccac
961 tctcctggta aa
```

Protein Sequence Defining the Murine IgG1 Heavy Chain Constant
Region Determined for 15D8, 20B4, 27H2, 2G4, and 4E7 (7D12)
(SEQ ID NO: 35)

```
  1 aktttppsvyp lapgsaaqtn smvtlgclvk gyfpepvtvt wnsgslssgv htfpavlqsd
 61 lytlsssvtv psstwpsetv tcnvahpass tkvdkkivpr dcgckpcict vpevssvfif
121 ppkpkdvlti tltpkvtcvv vdiskddpev qfswfvddve vhtaqtqpre eqfnstfrsv
181 selpimhqdw lngkefkcrv nsaafpapie ktisktkgrp kapqvytipp pkeqmakdkv
241 sltcmitdff peditvewqw ngqpaenykn tqpimdtdgs yfvysklnvq ksnweagntf
301 tcsvlheglh nhhtekslsh spgk
```

-continued

Nucleic Acid Sequence Encoding the Murine Kappa Light Chain Constant
Region Determined for 15D8, 20B4, 27H2, 2G4, and 4E7 (7D12)
(SEQ ID NO: 36)

```
  1 cgggctgatg ctgcaccaac tgtatccatc ttcccaccat ccagtgagca gttaacatct 61 ggaggtgcct cagtcgtgtg cttcttgaac aacttctacc ccaaagacat caatgtcaag 121 tggaagattg atggcagtga acgacaaaat ggcgtcctga acagttggac tgatcaggac 181 agcaaagaca gcacctacag catgagcagc accctcacgt tgaccaagga cgagtatgaa 241 cgacataaca gctatacctg tgaggccact cacaagacat caacttcacc cattgtcaag 301 agcttcaaca ggaatgagtg t
```

Protein Sequence Defining the Murine Kappa Light Chain Constant
Region Determined for 15D8, 20B4, 27H2, 2G4, and 4E7 (7D12)
(SEQ ID NO: 37)

```
  1 radaaptvsi fppsseqlts ggasvvcfln nfypkdinvk wkidgserqn gvlnswtdqd 61 skdstysmss tltltkdeye rhnsytceat hktstspivk sfnrnec
```

The amino acid sequences defining the immunoglobulin heavy chain variable regions for the antibodies produced in Example 1 are aligned in FIG. 2. Amino terminal signal peptide sequences (for proper expression/secretion) are not shown. The sequences defining Complementary Determining Region (CDR) sequences (Kabat definition), CDR$_1$, CDR$_2$, and CDR$_3$, are identified by boxes. FIG. 3 shows an alignment of the separate CDR$_1$, CDR$_2$, and CDR$_3$ sequences for each of the antibodies.

The amino acid sequences defining the immunoglobulin light chain variable regions for the antibodies produced in Example 1 are aligned in FIG. 4. Amino terminal signal peptide sequences (for proper expression/secretion) are not shown. The sequences defining CDR$_1$, CDR$_2$, and CDR$_3$ are identified by boxes. FIG. 5 shows an alignment of the separate CDR$_1$, CDR$_2$, and CDR$_3$ sequences for each of the antibodies.

Monoclonal antibodies 4E7 and 7D12 have identical heavy chain sequences and identical light chain sequences.

Table 1 is a concordance chart showing the SEQ ID NO. of each sequence discussed in this Example.

TABLE 1

| SEQ. ID NO. | Protein or Nucleic Acid |
| --- | --- |
| 1 | Heavy Chain Variable Region 15D8-nucleic acid |
| 2 | Heavy Chain Variable Region 15D8-protein |
| 3 | Light (kappa) Chain Variable Region 15D8-nucleic acid |
| 4 | Light (kappa) Chain Variable Region 15D8-protein |
| 17 | Heavy Chain CDR$_1$ 15D8 |
| 18 | Heavy Chain CDR$_2$ 15D8 |
| 20 | Heavy Chain CDR$_2$ 15D8-2 |
| 21 | Heavy Chain CDR$_2$ 15D8-3 |
| 19 | Heavy Chain CDR$_3$ 15D8 |
| 22 | Light (kappa) Chain CDR$_1$ 15D8 |
| 23 | Light (kappa) Chain CDR$_2$ 15D8 |
| 24 | Light (kappa) Chain CDR$_3$ 15D8 |
| 5 | Heavy Chain Variable Region 27H2-nucleic acid |
| 6 | Heavy Chain Variable Region 27H2-protein |
| 7 | Light (kappa) Chain Variable Region 27H2-nucleic acid |
| 8 | Light (kappa) Chain Variable Region 27H2-protein |
| 17 | Heavy Chain CDR$_1$ 27H2 |
| 25 | Heavy Chain CDR$_2$ 27H2 |
| 19 | Heavy Chain CDR$_3$ 27H2 |
| 22 | Light (kappa) Chain CDR$_1$ 27H2 |
| 26 | Light (kappa) Chain CDR$_2$ 27H2 |
| 27 | Light (kappa) Chain CDR$_3$ 27H2 |
| 9 | Heavy Chain Variable Region 2G4-nucleic acid |
| 10 | Heavy Chain Variable Region 2G4-protein |
| 7 | Light (kappa) Chain Variable Region 2G4-nucleic acid |

TABLE 1-continued

| SEQ. ID NO. | Protein or Nucleic Acid |
| --- | --- |
| 8 | Light (kappa) Chain Variable Region 2G4-protein |
| 17 | Heavy Chain CDR$_1$ 2G4 |
| 28 | Heavy Chain CDR$_2$ 2G4 |
| 19 | Heavy Chain CDR$_3$ 2G4 |
| 22 | Light (kappa) Chain CDR$_1$ 2G4 |
| 26 | Light (kappa) Chain CDR$_2$ 2G4 |
| 27 | Light (kappa) Chain CDR$_3$ 2G4 |
| 11 | Heavy Chain Variable Region 4E7 (7D12)-nucleic acid |
| 12 | Heavy Chain Variable Region 4E7 (7D12)-protein |
| 7 | Light (kappa) Chain Variable Region 4E7 (7D12)-nucleic acid |
| 8 | Light (kappa) Chain Variable Region 4E7 (7D12)-protein |
| 17 | Heavy Chain CDR$_1$ 4E7 (7D12) |
| 25 | Heavy Chain CDR$_2$ 4E7 (7D12) |
| 19 | Heavy Chain CDR$_3$ 4E7 (7D12) |
| 22 | Light (kappa) Chain CDR$_1$ 4E7 (7D12) |
| 26 | Light (kappa) Chain CDR$_2$ 4E7 (7D12) |
| 27 | Light (kappa) Chain CDR$_3$ 4E7 (7D12) |
| 13 | Heavy Chain Variable Region 20B4-nucleic acid |
| 14 | Heavy Chain Variable Region 20B4-protein |
| 15 | Light (kappa) Chain Variable Region 20B4-nucleic acid |
| 16 | Light (kappa) Chain Variable Region 20B4-protein |
| 29 | Heavy Chain CDR$_1$ 20B4 |
| 18 | Heavy Chain CDR$_2$ 20B4 |
| 30 | Heavy Chain CDR$_3$ 20B4 |
| 31 | Light (kappa) Chain CDR$_1$ 20B4 |
| 32 | Light (kappa) Chain CDR$_2$ 20B4 |
| 33 | Light (kappa) Chain CDR$_3$ 20B4 |

To create the complete heavy or kappa chain antibody sequences, each variable sequence above is combined with its respective constant region. For example, a complete heavy chain comprises a heavy variable sequence followed by the murine IgG1 heavy chain constant sequence and a complete kappa chain comprises a kappa variable sequence followed by the murine kappa light chain constant sequence.

The following sequences represent the actual or contemplated full length heavy and light chain sequences (i.e., containing both the variable and constant regions sequences) for each antibody described in this Example. The variable region sequences described herein can be ligated to each of a number of other constant region sequences known to those skilled in the art to produce active full length immunoglobulin heavy and light chains.

Nucleic Acid Sequence Encoding the Full Length 15D8 Heavy Chain
Sequence (15D8 Heavy Chain Variable Region and IgG1 Constant
Region)

(SEQ ID NO: 38)

```
   1 gagatccagc tgcagcagtc tggacctgag ctggtgaagc ctggggcttc agtgaaggta
  61 tcctgcaagg cttctggtta tgcattcact agctacaaca tgtactgggt gaagcagagc
 121 catggaaaga gccttgagtg gattggatat attgatcctt acaatggtgg tactagctac
 181 aaccagaagt tcaagggcaa ggccacattg actgttgaca gtcctccag cacagcctac
 241 atgcatctca acagcctgac atctgaggac tctgcagtct attactgtgc aagagagggg
 301 ggtaactacg aggcctggtt tgcttactgg ggccaaggga ctctggtcac tgtctctgca
 361 gccaaaacga cacccccatc tgtctatcca ctggcccctg gatctgctgc ccaaactaac
 421 tccatggtga ccctgggatg cctggtcaag gctatttcc ctgagccagt gacagtgacc
 481 tggaactctg gatccctgtc cagcggtgtg cacaccttcc cagctgtcct gcagtctgac
 541 ctctacactc tgagcagctc agtgactgtc ccctccagca cctggcccag cgagaccgtc
 601 acctgcaacg ttgcccaccc ggccagcagc accaaggtgg acaagaaaat tgtgcccagg
 661 gattgtggtt gtaagccttg catatgtaca gtcccagaag tatcatctgt cttcatcttc
 721 cccccaaagc ccaaggatgt gctcaccatt actctgactc ctaaggtcac gtgtgttgtg
 781 gtagacatca gcaaggatga tcccgaggtc cagttcagct ggtttgtaga tgatgtggag
 841 gtgcacacag ctcagacgca accccgggag gagcagttca acagcacttt ccgctcagtc
 901 agtgaacttc ccatcatgca ccaggactgg ctcaatggca aggagttcaa atgcagggtc
 961 aacagtgcag ctttccctgc ccccatcgag aaaaccatct ccaaaaccaa aggcagaccg
1021 aaggctccac aggtgtacac cattccacct cccaaggagc agatggccaa ggataaagtc
1081 agtctgacct gcatgataac agacttcttc cctgaagaca ttactgtgga gtggcagtgg
1141 aatgggcagc cagcggagaa ctacaagaac actcagccca tcatggacac agatggctct
1201 tacttcgtct acagcaagct caatgtgcag aagagcaact gggaggcagg aaatactttc
1261 acctgctctg tgttacatga gggcctgcac aaccaccata ctgagaagag cctctcccac
1321 tctcctggta aa
```

Protein Sequence Defining the Full Length 15D8 Heavy Chain Sequence
(15D8 Heavy Chain Variable Region and IgG1 Constant Region)

(SEQ ID NO: 39)

```
   1 eiqlqqsgpe lvkpgasvkv sckasgyaft synmywvkqs hgkslewigy idpyngtsy
  61 nqkfkgkatl tvdkssstay mhlnsltsed savyycareg gnyeawfayw gqgtlvtvsa
 121 akttppsvyp lapgsaaqtn smvtlgclvk gyfpepvtvt wnsgslssgv htfpavlqsd
 181 lytlsssvtv psstwpsetv tcnvahpass tkvdkkivpr dcgckpcict vpevssvfif
 241 ppkpkdvlti tltpkvtcvv vdiskddpev qfswfvddve vhtaqtqpre eqfnstfrsv
 301 selpimhqdw lngkefkcrv nsaafpapie ktisktkgrp kapqvytipp pkeqmakdkv
 361 sltcmitdff peditvewqw ngqpaenykn tqpimdtdgs yfvysklnvq ksnweagntf
 421 tcsvlheglh nhhtekslsh spgk
```

Nucleic Acid Sequence Encoding the Full Length 15D8 Light Chain
Sequence (15D8 Kappa Chain Variable Region and Constant Region)

(SEQ ID NO: 40)

```
   1 caaattgttc tcacccagtc tccagcactc atgtctgcat ctccagggga agggtcacc
  61 atgacctgca gtgccagctc aagtgtaagt tacatgtact ggtaccagca gaagccaaga
 121 tcctccccca aaccctggat ttatctcaca tcctacctgg cttctggagt ccctgctcgc
 181 ttcagtggca gtgggatctgg gacctcttac tctctcacaa tcagcagcat ggaggctgaa
 241 gatgctgcca cttattactg ccagcagtgg agtagttacc cgctcacgtt cggtgctgga
```

-continued

```
301 accaagctgg agctgaaacg ggctgatgct gcaccaactg tatccatctt cccaccatcc 361 agtgagcagt taacatctgg aggtgcctca gtcgtgtgct tcttgaacaa cttctacccc 421 aaagacatca atgtcaagtg gaagattgat ggcagtgaac gacaaaatgg cgtcctgaac 481 agttggactg atcaggacag caaagacagc acctacagca tgagcagcac cctcacgttg 541 accaaggacg agtatgaacg acataacagc tatacctgtg aggccactca caagacatca 601 acttcaccca ttgtcaagag cttcaacagg aatgagtgt
```

Protein Sequence Defining the Full Length 15D8 Light Chain Sequence
(15D8 Kappa Chain Variable Region and Constant Region)
(SEQ ID NO: 41)

```
  1 qivltqspal msaspgekvt mtcsasssvs ymywyqqkpr sspkpwiylt sylasgvpar 61 fsgsgsgtsy sltissmeae daatyycqqw ssypltfgag tklelkrada aptvsifpps 121 seqltsggas vvcflnnfyp kdinvkwkid gserqngvln swtdqdskds tysmsstltl 181 tkdeyerhns ytceathkts tspivksfnr nec
```

Nucleic Acid Sequence Encoding the Full Length 27H2 Heavy Chain
Sequence (27H2 Heavy Chain Variable Region and IgG1 Constant Region)
(SEQ ID NO: 42)

```
   1 gagatccagc tgcagcagtc tggacctgag ctggtgaagc ctggggcttc agtgaaggta 61 tcctgcaagg cttctggtta tgcattcact agctacaaca tgtactgggt gaagcagagc 121 catggaaaga gccttgagtg gattggatat attgatcctt acaatggtgg tactaggtac 181 aaccagaagt tcaagggcaa ggccacaatg actgttgaca gtcctccag cacagcctac 241 atgcatctca acagcctgac atctgaggac tctgcagtct attactgtgc aagagagggg 301 ggtaactacg aggcctggtt tgcttactgg ggccaaggga ctctggtcac tgtctctgca 361 gccaaaacga cacccccatc tgtctatcca ctggcccctg gatctgctgc ccaaactaac 421 tccatggtga ccctgggatg cctggtcaag gctatttcc ctgagccagt gacagtgacc 481 tggaactctg gatccctgtc cagcggtgtg cacaccttcc cagctgtcct gcagtctgac 541 ctctacactc tgagcagctc agtgactgtc ccctccagca cctggcccag cgagaccgtc 601 acctgcaacg ttgcccaccc ggccagcagc accaaggtgg acaagaaaat tgtgcccagg 661 gattgtggtt gtaagccttg catatgtaca gtcccagaag tatcatctgt cttcatcttc 721 cccccaaagc caaggatgt gctcaccatt actctgactc ctaaggtcac gtgtgttgtg 781 gtagacatca gcaaggatga tcccgaggtc cagttcagct ggtttgtaga tgatgtggag 841 gtgcacacag ctcagacgca accccgggag gagcagttca acagcacttt ccgctcagtc 901 agtgaacttc ccatcatgca ccaggactgg ctcaatggca aggagttcaa atgcagggtc 961 aacagtgcag ctttccctgc ccccatcgag aaaaccatct ccaaaaccaa aggcagaccg 1021 aaggctccac aggtgtacac cattccacct cccaaggagc agatggccaa ggataaagtc 1081 agtctgacct gcatgataac agacttcttc cctgaagaca ttactgtgga gtggcagtgg 1141 aatgggcagc cagcggagaa ctacaagaac actcagccca tcatggacac agatggctct 1201 tacttcgtct acagcaagct caatgtgcag aagagcaact gggaggcagg aaatactttc 1261 acctgctctg tgttacatga gggcctgcac aaccaccata ctgagaagag cctctcccac 1321 tctcctggta aa
```

Protein Sequence Defining the Full Length 27H2 Heavy Chain Sequence
(27H2 Heavy Chain Variable Region and IgG1 Constant Region)
(SEQ ID NO: 43)

```
  1 eiqlqqsgpe lvkpgasvkv sckasgyaft synmwvkqs hgkslewigy idpynggtry 61 nqkfkgkatm tvdkssstay mhlnsltsed savyycareg gnyeawfayw gqgtlvtvsa 121 akttppsvyp lapgsaaqtn smvtlgclvk gyfpepvtvt wnsgslssgv htfpavlqsd
```

```
181 lytlsssvtv psstwpsetv tcnvahpass tkvdkkivpr dcgckpcict vpevssvfif 241 ppkpkdvlti tltpkvtcvv vdiskddpev qfswfvddve vhtaqtqpre eqfnstfrsv 301 selpimhqdw lngkefkcrv nsaafpapie ktisktkgrp kapqvytipp pkeqmakdkv 361 sltcmitdff peditvewqw ngqpaenykn tqpimdtdgs yfvysklnvq ksnweagntf 421 tcsvlheglh nhhtekslsh spgk
```

Nucleic Acid Sequence Encoding the Full Length 27H2 Light Chain
Sequence (27H2 Kappa Chain Variable Region and Constant Region)
(SEQ ID NO: 44)

```
  1 caaattgttc tcacccagtc tccagcactc atgtctgcat ctccagggga gaaggtcacc 61 atgacctgca gtgccagctc aagtgtaagt tacatgtact ggtaccagca gaagccaaga 121 tcctccccca aaccctggat ttatctcaca tccaacctgg cttctggagt ccctgctcgc 181 ttcagtggca gtgggtctgg gacctcttac tctctcacaa tcagcagcat ggaggctgaa 241 gatgctgcca cttattactg ccagcagtgg agtagtaacc cgctcacgtt cggtgctggg 301 accaagctgg agctgaaacg ggctgatgct gcaccaactg tatccatctt cccaccatcc 361 agtgagcagt taacatctgg aggtgcctca gtcgtgtgct tcttgaacaa cttctacccc 421 aaagacatca atgtcaagtg gaagattgat ggcagtgaac gacaaaatgg cgtcctgaac 481 agttggactg atcaggacag caaagacagc acctacagca tgagcagcac cctcacgttg 541 accaaggacg agtatgaacg acataacagc tatacctgtg aggccactca caagacatca 601 acttcaccca ttgtcaagag cttcaacagg aatgagtgt
```

Protein Sequence Defining the Full Length 27H2 Light Chain Sequence
(27H2 Kappa Chain Variable Region and Constant Region)
(SEQ ID NO: 45)

```
  1 qivltqspal msaspgekvt mtcsasssvs ymywyqqkpr sspkpwiylt snlasgvpar 61 fsgsgsgtsy sltissmeae daatyycqqw ssnpltfgag tklelkrada aptvsifpps 121 seqltsggas vvcflnnfyp kdinvkwkid gserqngvln swtdqdskds tysmsstltl 181 tkdeyerhns ytceathkts tspivksfnr nec
```

Nucleic Acid Sequence Encoding the Full Length 2G4 Heavy Chain
Sequence (2G4 Heavy Chain Variable Region and IgG1 Constant Region)
(SEQ ID NO: 46)

```
  1 gagatccagc tgcagcagtc tggacctgag ctggtgaagc ctggggcttc agtgaaggta 61 tcctgcaagg cttctggtta tgcattcaca agctacaaca tgtactgggt gaagcagagc 121 catggaaaga gccttgagtg gattggatat attgatcctt acaatggtgg tactagggac 181 aaccagaagt tcaagggcaa ggccacattg actgttgaca gtcctccag tacagcctac 241 atgcatctca acagcctgac atctgaggac tctgcagtct attactgtgc aagagagggg 301 ggtaactacg aggcctggtt tgcttactgg ggccaaggga ctctggtcac tgtctctgca 361 gccaaaacga cacccccatc tgtctatcca ctggcccctg gatctgctgc ccaaactaac 421 tccatggtga ccctgggatg cctggtcaag ggctatttcc ctgagccagt gacagtgacc 481 tggaactctg gatccctgtc cagcggtgtg cacaccttcc cagctgtcct gcagtctgac 541 ctctacactc tgagcagctc agtgactgtc ccctccagca cctggcccag cgagaccgtc 601 acctgcaacg ttgcccaccc ggccagcagc accaaggtgg acaagaaaat tgtgcccagg 661 gattgtggtt gtaagccttg catatgtaca gtcccagaag tatcatctgt cttcatcttc 721 cccccaaagc ccaaggatgt gctcaccatt actctgactc ctaaggtcac gtgtgttgtg 781 gtagacatca gcaaggatga tcccgaggtc cagttcagct ggtttgtaga tgatgtggag 841 gtgcacacag ctcagacgca accccgggag gagcagttca acagcacttt ccgctcagtc 901 agtgaacttc ccatcatgca ccaggactgg ctcaatggca aggagttcaa atgcagggtc
```

```
 961 aacagtgcag ctttccctgc ccccatcgag aaaaccatct ccaaaaccaa aggcagaccg 1021 aaggctccac aggtgtacac cattccacct cccaaggagc agatggccaa ggataaagtc 1081 agtctgacct gcatgataac agacttcttc cctgaagaca ttactgtgga gtggcagtgg 1141 aatgggcagc cagcggagaa ctacaagaac actcagccca tcatggacac agatggctct 1201 tacttcgtct acagcaagct caatgtgcag aagagcaact gggaggcagg aaatactttc 1261 acctgctctg tgttacatga gggcctgcac aaccaccata ctgagaagag cctctcccac 1321 tctcctggta aa
```

Protein Sequence Defining the Full Length 2G4 Heavy Chain Sequence
(2G4 Heavy Chain Variable Region and IgG1 Constant Region)
(SEQ ID NO: 47)
```
  1 eiqlqqsgpe lvkpgasvkv sckasgyaft synmywvkqs hgkslewigy idpynggtrd 61 nqkfkgkatl tvdkssstay mhlnsltsed savyycareg gnyeawfayw gqgtlvtvsa 121 akttppsvyp lapgsaaqtn smvtlgclvk gyfpepvtvt wnsgslssgv htfpavlqsd 181 lytlsssvtv psstwpsetv tcnvahpass tkvdkkivpr dcgckpcict vpevssvfif 241 ppkpkdvlti tltpkvtcvv vdiskddpev qfswfvddve vhtaqtqpre eqfnstfrsv 301 selpimhqdw lngkefkcrv nsaafpapie ktisktkgrp kapqvytipp pkeqmakdkv 361 sltcmitdff peditvewqw ngqpaenykn tqpimdtdgs yfvysklnvq ksnweagntf 421 tcsvlheglh nhhtekslsh spgk
```

Nucleic Acid Sequence Encoding the Full Length 2G4 Light Chain
Sequence (2G4 Kappa Chain Variable Region and Constant Region)
(SEQ ID NO: 48)
```
  1 caaattgttc tcacccagtc tccagcactc atgtctgcat ctccagggga gaaggtcacc 61 atgacctgca gtgccagctc aagtgtaagt tacatgtact ggtaccagca gaagccaaga 121 tcctccccca aaccctggat ttatctcaca tccaacctgg cttctggagt ccctgctcgc 181 ttcagtggca gtgggtctgg gacctcttac tctctcacaa tcagcagcat ggaggctgaa 241 gatgctgcca cttattactg ccagcagtgg agtagtaacc cgctcacgtt cggtgctggg 301 accaagctgg agctgaaacg ggctgatgct gcaccaactg tatccatctt cccaccatcc 361 agtgagcagt taacatctgg aggtgcctca gtcgtgtgct tcttgaacaa cttctacccc 421 aaagacatca atgtcaagtg gaagattgat ggcagtgaac gacaaaatgg cgtcctgaac 481 agttggactg atcaggacag caaagacagc acctacagca tgagcagcac cctcacgttg 541 accaaggacg agtatgaacg acataacagc tatacctgtg aggccactca caagacatca 601 acttcaccca ttgtcaagag cttcaacagg aatgagtgt
```

Protein Sequence Defining the Full Length 2G4 Light Chain Sequence
(2G4 Kappa Chain Variable Region and Constant Region)
(SEQ ID NO: 49)
```
  1 qivltqspal msaspgekvt mtcsasssvs ymywyqqkpr sspkpwiylt snlasgvpar 61 fsgsgsgtsy sltissmeae daatyycqqw ssnpltfgag tklelkrada aptvsifpps 121 seqltsggas vvcflnnfyp kdinvkwkid gserqngvln swtdqdskds tysmsstltl 181 tkdeyerhns ytceathkts tspivksfnr nec
```

Nucleic Acid Sequence Encoding the Full Length 4E7 (7D12) Heavy
Chain Sequence (4E7 (7D12) Heavy Chain Variable Region and IgG1
Constant Region)
(SEQ ID NO: 50)
```
  1 gagatccagc tgcagcagtc tggacctgag ctggtgaagc ctggggcttc agtgaaggta 61 tcctgcaagg cttctggtta tgcattcact agctacaaca tgtactgggt gaagcagagc 121 catggaaaga gccttgagtg gattggatat attgatcctt acaatggtgg tactaggtac 181 aaccagaagt tcaagggcaa ggccacattg actgttgaca agtcctccag cacagcctac
```

-continued

```
 241 atgcatctca acagcctgac atctgaggac tctgcagtct attactgtgc aagagagggg
 301 ggtaactacg aggcctggtt tgcttactgg ggccaaggga ctctggtcac tgtctctgca
 361 gccaaaacga cccccccatc tgtctatcca ctggcccctg gatctgctgc ccaaactaac
 421 tccatggtga ccctgggatg cctggtcaag ggctatttcc ctgagccagt gacagtgacc
 481 tggaactctg gatccctgtc cagcggtgtg cacaccttcc cagctgtcct gcagtctgac
 541 ctctacactc tgagcagctc agtgactgtc ccctccagca cctggcccag cgagaccgtc
 601 acctgcaacg ttgcccaccc ggccagcagc accaaggtgg acaagaaaat tgtgcccagg
 661 gattgtggtt gtaagccttg catatgtaca gtcccagaag tatcatctgt cttcatcttc
 721 cccccaaagc ccaaggatgt gctcaccatt actctgactc taaggtcac gtgtgttgtg
 781 gtagacatca gcaaggatga tcccgaggtc cagttcagct ggtttgtaga tgatgtggag
 841 gtgcacacag ctcagacgca accccgggag gagcagttca acagcacttt ccgctcagtc
 901 agtgaacttc ccatcatgca ccaggactgg ctcaatggca aggagttcaa atgcagggtc
 961 aacagtgcag ctttccctgc ccccatcgag aaaaccatct ccaaaaccaa aggcagaccg
1021 aaggctccac aggtgtacac cattccacct cccaaggagc agatggccaa ggataaagtc
1081 agtctgacct gcatgataac agacttcttc cctgaagaca ttactgtgga gtggcagtgg
1141 aatgggcagc cagcggagaa ctacaagaac actcagccca tcatggacac agatggctct
1201 tacttcgtct acagcaagct caatgtgcag aagagcaact gggaggcagg aaatactttc
1261 acctgctctg tgttacatga gggcctgcac aaccaccata ctgagaagag cctctcccac
1321 tctcctggta aa
```

Protein Sequence Defining the Full Length 4E7 (7D12) Heavy Chain Sequence (4E7 (7D12) Heavy Chain Variable Region and IgG1 Constant Region)

(SEQ ID NO: 51)
```
  1 eiqlqqsgpe lvkpgasvkv sckasgyaft synmywvkqs hgkslewigy idpynggtry
 61 nqkfkgkatl tvdkssstay mhlnsltsed savyycareg gnyeawfayw gqgtlvtvsa
121 akttppsvyp lapgsaaqtn smvtlgclvk gyfpepvtvt wnsgslssgv htfpavlqsd
181 lytlsssvtv psstwpsetv tcnvahpass tkvdkkivpr dcgckpcict vpevssvfif
241 ppkpkdvlti tltpkvtcvv vdiskddpev qfswfvddve vhtaqtqpre eqfnstfrsv
301 selpimhqdw lngkefkcrv nsaafpapie ktisktkgrp kapqvytipp pkeqmakdkv
361 sltcmitdff peditvewqw ngqpaenykn tqpimdtdgs yfvysklnvq ksnweagntf
421 tcsvlheglh nhhtekslsh spgk
```

Nucleic Acid Sequence Encoding the Full Length 4E7 (7D12) Light Chain Sequence (4E7 (7D12) Kappa Chain Variable Region and Constant Region)

(SEQ ID NO: 52)
```
  1 caaattgttc tcacccagtc tccagcactc atgtctgcat ctccagggga aaggtcacc
 61 atgacctgca gtgccagctc aagtgtaagt tacatgtact ggtaccagca gaagccaaga
121 tcctccccca aaccctggat ttatctcaca tccaacctgg cttctggagt ccctgctcgc
181 ttcagtggca gtgggtctgg gacctcttac tctctcacaa tcagcagcat ggaggctgaa
241 gatgctgcca cttattactg ccagcagtgg agtagtaacc cgctcacgtt cggtgctggg
301 accaagctgg agctgaaacg ggctgatgct gcaccaactg tatccatctt cccaccatcc
361 agtgagcagt taacatctgg aggtgcctca gtcgtgtgct tcttgaacaa cttctacccc
421 aaagacatca atgtcaagtg gaagattgat ggcagtgaac gacaaaatgg cgtcctgaac
481 agttggactg atcaggacag caaagacagc acctacagca tgagcagcac cctcacgttg
```

```
541 accaaggacg agtatgaacg acataacagc tatacctgtg aggccactca caagacatca 601 acttcaccca ttgtcaagag cttcaacagg aatgagtgt
```

Protein Sequence Defining the Full Length 4E7 (7D12) Light Chain
Sequence (4E7 (7D12) Kappa Chain Variable Region and Constant Region)
(SEQ ID NO: 53)

```
  1 qivltqspal msaspgekvt mtcsasssvs ymywyqqkpr sspkpwiylt snlasgvpar 61 fsgsgsgtsy sltissmeae daatyycqqw ssnpltfgag tklelkrada aptvsifpps 121 seqltsggas vvcflnnfyp kdinvkwkid gserqngvln swtdqdskds tysmsstltl 181 tkdeyerhns ytceathkts tspivksfnr nec
```

Nucleic Acid Sequence Encoding the Full Length 20B4 Heavy Chain
Sequence (20B4 Heavy Chain Variable Region and IgG1 Constant Region)
(SEQ ID NO: 54)

```
   1 gagatccagc tgcagcagtc tggacctgag ctggtgaagc ctggggcttc agtgaaggta 61 tcctgcaagg cttctggtta ctcactcact gactacaaca tgtactgggt gaagcagagc 121 catggaaaga gccttgagtg gattggatat attgatcctt acaatggtgg tactagctac 181 aaccagaagt tcaagggcaa ggccacattg actgttgaca agtcctccag cacagccttc 241 atgcatctca cagcctgac atctgaggac tctgcagtct attactgtgc aagatcgttg 301 ggacctgatt ttgactactg gggccaaggc accactctca cagtctcctc agccaaaacg 361 acaccccat ctgtctatcc actggcccct ggatctgctg cccaaactaa ctccatggtg 421 accctgggat gcctggtcaa gggctatttc cctgagccag tgacagtgac ctggaactct 481 ggatccctgt ccagcggtgt gcacaccttc ccagctgtcc tgcagtctga cctctacact 541 ctgagcagct cagtgactgt cccctccagc acctggccca cgagaccgt cacctgcaac 601 gttgcccacc cggccagcag caccaaggtg gacaagaaaa ttgtgcccag ggattgtggt 661 tgtaagcctt gcatatgtac agtcccagaa gtatcatctg tcttcatctt ccccccaaag 721 cccaaggatg tgctcaccat tactctgact cctaaggtca cgtgtgttgt ggtagacatc 781 agcaaggatg atcccgaggt ccagttcagc tggtttgtag atgatgtgga ggtgcacaca 841 gctcagacgc aaccccggga ggagcagttc aacagcactt tccgctcagt cagtgaactt 901 cccatcatgc accaggactg gctcaatggc aaggagttca atgcagggt caacagtgca 961 gctttccctg cccccatcga gaaaaccatc tccaaaacca aaggcagacc gaaggctcca 1021 caggtgtaca ccattccacc tcccaaggag cagatggcca aggataaagt cagtctgacc 1081 tgcatgataa cagacttctt ccctgaagac attactgtgg agtggcagtg gaatgggcag 1141 ccagcggaga actacaagaa cactcagccc atcatggaca cagatggctc ttacttcgtc 1201 tacagcaagc tcaatgtgca gaagagcaac tgggaggcag gaaatacttt cacctgctct 1261 gtgttacatg agggcctgca caaccaccat actgagaaga gcctctccca ctctcctggt 1321 aaa
```

Protein Sequence Defining the Full Length 20B4 Heavy Chain Sequence
(20B4 Heavy Chain Variable Region and IgG1 Constant Region)
(SEQ ID NO: 55)

```
  1 eiqlqqsgpe lvkpgasvkv sckasgyslt dynmywvkqs hgkslewigy idpynggtsy 61 nqkfkgkatl tvdkssstaf mhlnsltsed savyycarsl gpdfdywgqg ttltvssakt 121 tppsvyplap gsaaqtnsmv tlgclvkgyf pepvtvtwns gslssgvhtf pavlqsdlyt 181 lsssvtvpss twpsetvtcn vahpasstkv dkkivprdcg ckpcictvpe vssvfifppk 241 pkdvltitlt pkvtcvvvdi skddpevqfs wfvddvevht aqtqpreeqf nstfrsvsel 301 pimhqdwlng kefkcrvnsa afpapiekti sktkgrpkap qvytipppke qmakdkvslt
```

```
361 cmitdffped itvewqwngq paenykntqp imdtdgsyfv ysklnvqksn weagntftcs 421 vlheglhnhh tekslshspg k Nucleic Acid Sequence Encoding the Full Length 20B4 Light Chain
Sequence (20B4 Kappa Chain Variable Region and Constant Region)
                                                       (SEQ ID NO: 56)
  1 caaattgttc tcacccagtc tccagcaatc atgtctgcat ctccagggga gaaggtcacc 61 atgacctgca gtgccagctc aagtgtaaat tacatgcact ggtaccagca gaagtcaggc 121 acctccccca aagatggat  ttatgacaca tccaaactgg cttctggagt ccctgctcgc 181 ttcagtggca gtgggtctgg gacctcttac tctctcacaa tcagcagcat ggaggctgaa 241 gatactgcca cttattactg tcaacagtgg aatagtaacc cactcacgtt cggtgcgggg 301 accaagctgg agctgaaacg ggctgatgct gcaccaactg tatccatctt cccaccatcc 361 agtgagcagt taacatctgg aggtgcctca gtcgtgtgct tcttgaacaa cttctacccc 421 aaagacatca atgtcaagtg gaagattgat ggcagtgaac gacaaaatgg cgtcctgaac 481 agttggactg atcaggacag caaagacagc acctacagca tgagcagcac cctcacgttg 541 accaaggacg agtatgaacg acataacagc tatacctgtg aggccactca caagacatca 601 acttcaccca ttgtcaagag cttcaacagg aatgagtgt Protein Sequence Defining the Full Length 20B4 Light Chain Sequence
(20B4 Kappa Chain Variable Region and Constant Region)
                                                       (SEQ ID NO: 57)
  1 qivltqspai msaspgekvt mtcsassssvn ymhwyqqksg tspkrwiydt sklasgvpar 61 fsgsgsgtsy sltissmeae dtatyycqqw nsnpltfgag tklelkrada aptvsifpps 121 seqltsggas vvcflnnfyp kdinvkwkid gserqngvln swtdqdskds tysmsstltl 181 tkdeyerhns ytceathkts tspivksfnr nec
```

For convenience, Table 2 provides a concordance chart showing the correspondence between the full length sequences of the antibodies discussed in this Example with those presented in the Sequence Listing.

TABLE 2

| SEQ. ID NO. | Protein or Nucleic Acid |
|---|---|
| 38 | 15D8 Heavy Variable + IgG1 constant-nucleic acid |
| 39 | 15D8 Heavy Variable + IgG1 constant-protein |
| 40 | 15D8 Kappa Variable + constant-nucleic acid |
| 41 | 15D8 Kappa Variable + constant -protein |
| 42 | 27H2 Heavy Variable + IgG1 constant-nucleic acid |
| 43 | 27H2 Heavy Variable + IgG1 constant-protein |
| 44 | 27H2 Kappa Variable + constant-nucleic acid |
| 45 | 27H2 Kappa Variable + constant -protein |
| 46 | 2G4 Heavy Variable + IgG1 constant-nucleic acid |
| 47 | 2G4 Heavy Variable + IgG1 constant-protein |
| 48 | 2G4 Kappa Variable + constant-nucleic acid |
| 49 | 2G4 Kappa Variable + constant -protein |
| 50 | 4E7 (7D12) Heavy Variable + IgG1 constant-nucleic acid |
| 51 | 4E7 (7D12) Heavy Variable + IgG1 constant-protein |
| 52 | 4E7 (7D12) Kappa Variable + constant-nucleic acid |
| 53 | 4E7 (7D12) Kappa Variable + constant -protein |
| 54 | 20B4 Heavy Variable + IgG1 constant-nucleic acid |
| 55 | 20B4 Heavy Variable + IgG1 constant-protein |
| 56 | 20B4 Kappa Variable + constant-nucleic acid |
| 57 | 20B4 Kappa Variable + constant -protein |

Example 3

Binding Affinities of Anti-FGFR3 Monoclonal Antibodies

The binding affinities and kinetics of interaction of the monoclonal antibodies (15D8, 27H2, 2G4, and 4E7(7D12)) produced in Example 1 against recombinant human FGFR3 (IIIb and IIIc isoforms) Fc fusion protein (rhFGFR3 IIIb Fc or rhFGFR3 IIIc Fc) were measured by surface plasmon resonance using a Biacore™ T100 (Biacore) instrument.

Rabbit anti-mouse immunoglobulins (Biacore, Catalog No. BR-1005-14) were immobilized on carboxymethylated dextran CM4 sensor chips (Biacore, Catalog No. BR-1005-34) by amine coupling (Biacore, Catalog No. BR-1000-50) using a standard coupling protocol according to manufacturer's instructions. The analyses were performed at 25° C. and 37° C. using PBS (Invitrogen, Catalog No. 14040-133) containing 0.05% surfactant P20 (Biacore, Catalog No. BR-1000-54) as running buffer.

The antibodies were captured in an individual flow cell at a flow rate of 10 μl/min. Injection time was varied for each antibody to yield approximately 40-50 RU of antibody captured for each cycle. Buffer or rhFGFR3 IIIb Fc (R&D Systems, Catalog No. 1264-FR-050) or rhFGFR3 IIIc Fc (R&D Systems, Catalog No. 766-FR-050) diluted in running buffer was injected sequentially over a reference surface (no antibody captured) and the active surface (antibody to be tested) for 300 sec at 60 μl/min. The dissociation phase was monitored for 30 minutes. The surface was then regenerated with two 60-seconds injection of 10 mM Glycine-HCl, pH 1.7 (made from Glycine pH 1.5 (Biacore, Catalog No. BR-1003-

54) and pH 2.0 (Biacore, Catalog No. BR-1003-55)) at a flow rate of 60 μl/min. rhFGFR3 Fc concentrations tested were 0.62 nM to 40 nM.

Kinetic parameters were determined using the kinetic function of the BIAevalutation software (Biacore) with a double reference subtraction. Kinetic parameters for each antibody, $k_a$ (association rate constant), $k_d$ (dissociation rate constant) and $K_D$ (equilibrium dissociation constant) were determined. Kinetic values of the monoclonal antibodies at 25° C. are summarized in Table 3.

TABLE 3

| FGFR3 isoform | Antibody | ka (1/Ms) | Standard Deviation | kd (1/s) | Standard Deviation | KD (M) | Standard Deviation | n |
|---|---|---|---|---|---|---|---|---|
| FGFR3 IIIb | 4E7 | 1.5E+05 | 1.6E+05 | 3.7E−04 | 2.3E−04 | 3.3E−09 | 1.7E−09 | 3 |
|  | 15D8 | 2.0E+05 | 1.3E+05 | 3.3E−04 | 6.5E−05 | 2.6E−09 | 2.2E−09 | 3 |
|  | 27H2 | 9.0E+04 | 4.5E+04 | 2.6E−04 | 1.0E−04 | 3.0E−09 | 6.8E−10 | 3 |
|  | 2G4 | 1.2E+05 | * | 3.2E−04 | * | 3.2E−09 | * | 2 |
| FGFR3 IIIc | 4E7 | 1.1E+05 | 7.1E+04 | 1.9E−04 | 6.4E−05 | 2.6E−09 | 2.0E−09 | 4 |
|  | 15D8 | 9.3E+04 | 3.0E+04 | 2.0E−04 | 6.7E−05 | 2.2E−09 | 1.0E−09 | 4 |
|  | 27H2 | 7.5E+04 | 1.3E+03 | 1.6E−04 | 7.8E−05 | 2.1E−09 | 1.0E−09 | 3 |
|  | 2G4 | 1.0E+05 | * | 1.1E−04 | * | 1.1E−09 | * | 1 |

* Standard deviation not calculated when n < 3

Kinetic values of the monoclonal antibodies at 37° C. are summarized in Table 4.

TABLE 4

| FGFR3 isoform | Antibody | ka (1/Ms) | kd (1/s) | KD (M) | n |
|---|---|---|---|---|---|
| FGFR3 IIIb | 4E7 | 7.4E+04 | 2.3E−04 | 3.3E−09 | 2 |
|  | 15D8 | 9.4E+04 | 3.0E−04 | 3.2E−09 | 2 |
|  | 27H2 | 1.0E+05 | 1.9E−04 | 2.1E−09 | 2 |
|  | 2G4 | 1.5E+05 | 2.3E−04 | 1.4E−09 | 2 |
| FGFR3 IIIc | 4E7 | 9.4E+04 | 1.7E−04 | 2.2E−09 | 2 |
|  | 15D8 | 1.2E+05 | 1.8E−04 | 1.8E−09 | 2 |
|  | 27H2 | 9.6E+04 | 2.0E−04 | 2.1E−09 | 2 |
|  | 2G4 | 1.0E+05 | 2.6E−04 | 2.6E−09 | 1 |

Example 4

Neutralization Activity of Anti-hFGFR3 Antibodies

The antibodies produced in Example 1 were characterized for their ability to inhibit recombinant hFGFR3 IIIb binding to FGF1 (also known as FGF acidic).

The antibodies were tested by ECL (Electrochemiluminescence) assay for inhibition of hFGFR3 IIIB binding to FGF-1. MA2400 96-well high binding plates (Meso Scale Discovery, Catalog No. L15XB-6) were coated with 25 μl of 0.8 μg/mL FGF-1 (R&D Systems, Catalog No. 232-FA-025) in PBS (Invitrogen, Catalog No. 14040-133) for 1 hour at room temperature with agitation. The plates then were washed 3 times with PBS and blocked with 200 μl of PBS containing 5% BSA (Sera Care Life Sciences, Catalog No. AP-4510-80) and 5 μg/mL heparin (Sigma, Catalog No. H4784) for 1 hour at room temperature. The antibodies (concentration range: 0.029-30 μg/mL) were incubated for 1 hour at room temperature with 1.7 μg/mL rhFGFR3 IIIb Fc (R&D Systems, Catalog No. 1264-FR-050) and 5 μg/mL heparin. After washing the plates 3 times with PBS, 25 μl of the antibody-receptor mixture was added to the plates for another hour at room temperature with agitation. The plates were washed three times with PBS and incubated with 25 μl of 1 μg/mL ST-anti- human IgG antibody (Meso Scale Discovery, Catalog No. R32AJ-1) for 1 hour at room temperature with agitation. The plates then were washed 3 times with PBS, and 150 μl of 1× read buffer (Meso Scale Discovery, Catalog No. R92TC-1) was added to each well before the plates were analyzed on a Sector Imager 2400 (Meso Scale Discovery) instrument.

Figure 6:
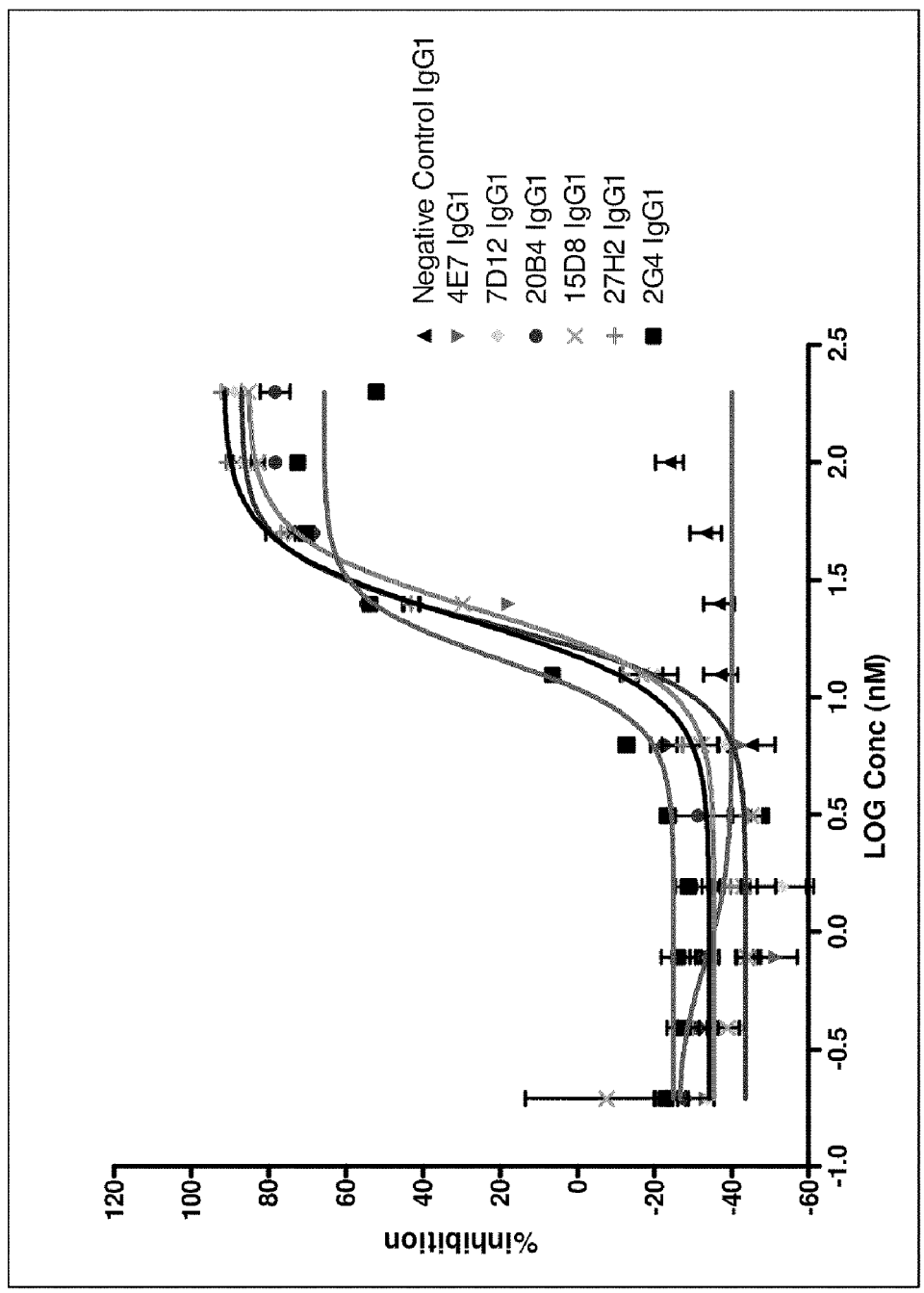
FIG. 6 is a graph summarizing results from an experiment to measure neutralization activity of negative control IgG1 (▲) and anti-FGFR3 monoclonal antibodies 15D8 (X), 27H2 (+), 2G4 (■), 4E7 (▼), 7D12 (◊), and 20B4 (●) to inhibit FGFR3 binding to FGF1.
Figure 7:
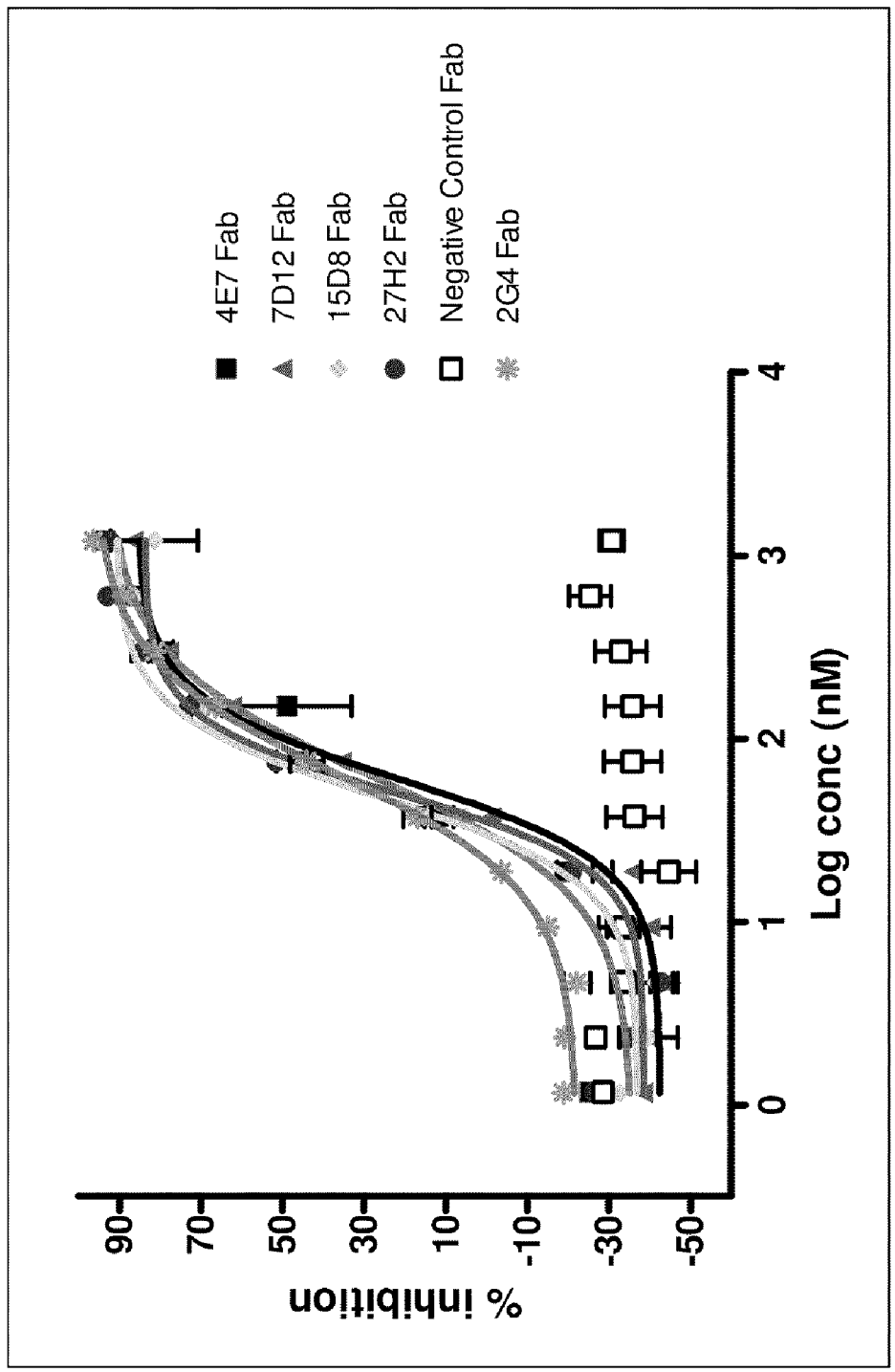
FIG. 7 is a graph summarizing results from an experiment to measure neutralization activity of negative control IgG1 Fab (□) and anti-FGFR3 Fab fragments 15D8 (◊), 27H2 (●), 2G4 (*), 4E7 (■), and 7D12 (▲) to inhibit FGFR3 binding to FGF1.

The interaction of FGF1 with FGFR3 was inhibited by 4E7, 7D12, 15D8, 27H2, 2G4, and 20B4 IgG1 as shown in FIG. 6. The interaction of FGF1 with FGFR3 was also inhibited by Fab fragments as shown in FIG. 7 (20B4 not shown).

The $IC_{50}$ and maximum percent inhibition values for the murine anti-human FGFR3 antibodies (IgG1) and Fab fragments (Fab) were calculated and are summarized in Table 5.

TABLE 5

| | $IC_{50}$ (nM) | | Maximum Neutralization (%) | | |
|---|---|---|---|---|---|
| Antibody | Average | Standard Deviation | Average | Standard Deviation | n |
| 15D8 IgG1 | 15.4 | 7.0 | 80.5 | 24.5 | 3 |
| 20B4 IgG1 | 46.4 | 62.1 | 58.4 | 36.2 | 3 |
| 27H2 IgG1 | 15.4 | 5.4 | 99.6 | 8.2 | 3 |
| 2G4 IgG1 | 11.1 | * | 64.9 | * | 2 |
| 4E7 IgG1 | 18.5 | 7.0 | 91.2 | 7.0 | 3 |
| 7D12 IgG1 | 13.3 | 6.6 | 93.9 | 5.9 | 3 |
| 15D8 Fab | 63.8 | 28.7 | 91.7 | 6.9 | 3 |
| 20B4 Fab | 161.5 | * | 101.2 | * | 2 |
| 27H2 Fab | 53.5 | 22.9 | 95.8 | 4.5 | 3 |
| 2G4 Fab | 65.0 | * | 96.2 | * | 1 |
| 4E7 Fab | 69.5 | 32.4 | 92.2 | 6.2 | 3 |
| 7D12 Fab | 50.0 | 11.3 | 88.8 | 8.7 | 3 |

* Standard deviation not calculated when n < 3

The results demonstrate that all the antibodies (i.e., 15D8, 27H2, 2G4, 4E7, 7D12) except for 20B4 efficiently neutralize hFGFR3 binding to FGF1. The 2G4 Fab fragment neutralized hFGFR3 binding to FGF1 better than the 2G4 IgG1 antibody.

Example 5

Anti-Proliferative Activity of Anti-hFGFR3 Antibodies

In this Example, the antibodies produced in Example 1 were characterized for their ability to inhibit FGF1 dependent proliferation of cells.

FDCP-1 cells (mouse bone marrow cells obtained from German Collection of Microorganisms and Cell Cultures) were transfected with plasmids encoding human FGFR3 IIIb, FGFR3 IIIc, or a mutant variant G380R (an activating mutation associated with the skeletal disorder, achondroplasia (Webster and Donoghue (1996) EMBO J. 15:520-527) by electroporation and selected with G418 (600 μg/mL). Single clones were isolated and tested for their FGF1-dependent proliferation in the absence of IL3 containing WEHI-conditioned medium. FDCP-FGFR3 IIIb #122, FDCP-FGFR3 IIIc #109, FGFR3 IIIc G380R #1 exhibited FGF-1 induced proliferation in the absence of IL3.

To screen for antagonistic FGFR3 antibodies, hybridoma supernatants containing FGFR3 antibodies were added to FDCP-FGFR3 IIIb #122 or FDCP-FGFR3 IIIc #109 cells cultured in basic growth medium (70% ISCOVE's Modified Dulbecco's Medium (Invitrogen, Catalog No. 12440-053), 20% horse serum (Invitrogen, Catalog No. 26050-088) and 10% WEHI-culture medium (90% ISCOVE's MDM+10% FBS (Invitrogen, Catalog No. 10438-026)+2 mM L-glutamine (Invitrogen, Catalog No. 25030-081)+0.0025 mM mercaptoethanol (Invitrogen, Catalog No. 21985-023))) at a 1:1 ratio (volume) in a 96-well plate (70,000 cells/well) in the absence or presence of FGF1 (8 ng/mL) and heparin (5 μg/mL). MTT (3-(4,5-Dimethylthiazol-2-yl)-2,5-diphenyltetrazolium bromide) assays were conducted two to three days post FGF1 stimulation. Top antagonistic antibodies were selected for further characterization.

To test the effect of FGFR3 antibodies on the proliferation of various FGFR3-driven FDCP cells, varying amounts of antibodies were added to the cells along with FGF1 (8 ng/mL) and heparin (50 μg/mL). The cells were cultured in basic growth medium (70% ISCOVE'S, 20% horse serum and 10% WEHI-culture medium (90% Iscove's MDM+10% FBS+2 mM L-glutamine+0.0025 mM mercaptoethanol)) in a 96-well plate (70,000 cells/well). The final concentration of FGF1 and heparin used in the assay is 8 ng/mL and 5 μg/mL, respectively. MTT assay was conducted one to three days post FGF1 stimulation.

Figure 8:
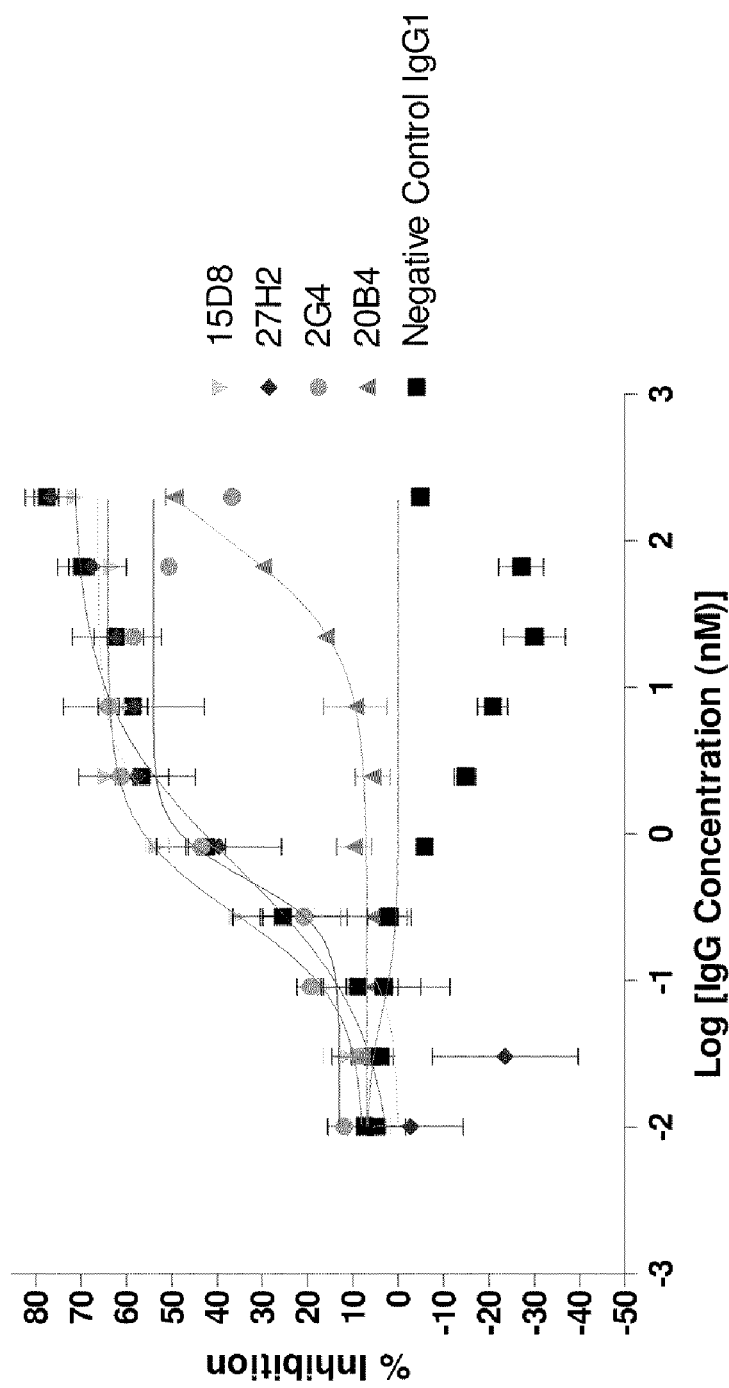
FIG. 8 is a graph summarizing results from an experiment to measure anti-proliferation activity of negative control (murine IgG1) (■) and anti-FGFR3 monoclonal antibodies 15D8 (▼), 27H2 (♦), 2G4 (●), and 20B4 (▲) in FDCP-FGFR3 IIIc-109 cells.

An example of the dose dependent inhibition of FDCP-FGFR3c cell proliferation by murine anti-human FGFR3 antibodies is shown in FIG. 8. Inhibition data of FDCP-FGFR3 cell line proliferation with monoclonal antibodies (15D8, 27H2, 4E7, 2G4, and 20B4) are summarized in Table 6.

TABLE 6

| | FDCP Proliferation IC$_{50}$ | | |
|---|---|---|---|
| Antibody | FGFR3 IIIb (nM) | PGFR3 IIIc (nM) | FGFR3 IIIc G380R (nM) |
| 15D8 | 0.14 | 0.28 | 3.1 |
| 27H2 | 0.56 | 0.59 | 8.8 |
| 4E7 | 0.9 | 0.62 | 3.5 |
| 2G4 | 0.63 | 0.5 | 11.7 |
| 20B4 | 1.51 | 102.1 | N/A |

The results in Table 6 demonstrate that all the antibodies (i.e., 15D8, 27H2, 4E7, 2G4) except for 20B4 strongly inhibited FGF1 induced proliferation in FDCP-FGFR3 IIIb and FDCP-FGFR3 IIIc cell lines. Inhibition by 20B4 was maximally 40% and an IC$_{50}$ value was not calculated. The antibodies also have an inhibitory effect on FGFR3 IIIc G380R, a mutant variant that is correlated with the skeletal disorder, achondroplasia.

Example 6

Tumor Inhibition in OPM-2 Xenograft Model

The ability of murine monoclonal antibodies of the invention to inhibit tumor growth was tested in an OPM-2 xenograft model. OPM-2 cells were grown in culture at 37° C. in an atmosphere containing 5% $CO_2$, using RMPI medium (Invitrogen) containing 10% fetal bovine serum (Invitrogen). Cells were inoculated subcutaneously into the flank of 8-week old female CB.17 SCID mice (Taconic Labs) with $5\times10^6$ cells per mouse in 50% matrigel (BD Biosciences, Cat No. 356237).

Tumor measurements were taken twice weekly using vernier calipers. Tumor volume was calculated using the formula: width×width×length/2. When tumors reached approximately 150 mm$^3$, the mice were randomized into 4 groups of 10 mice each.

Figure 9:
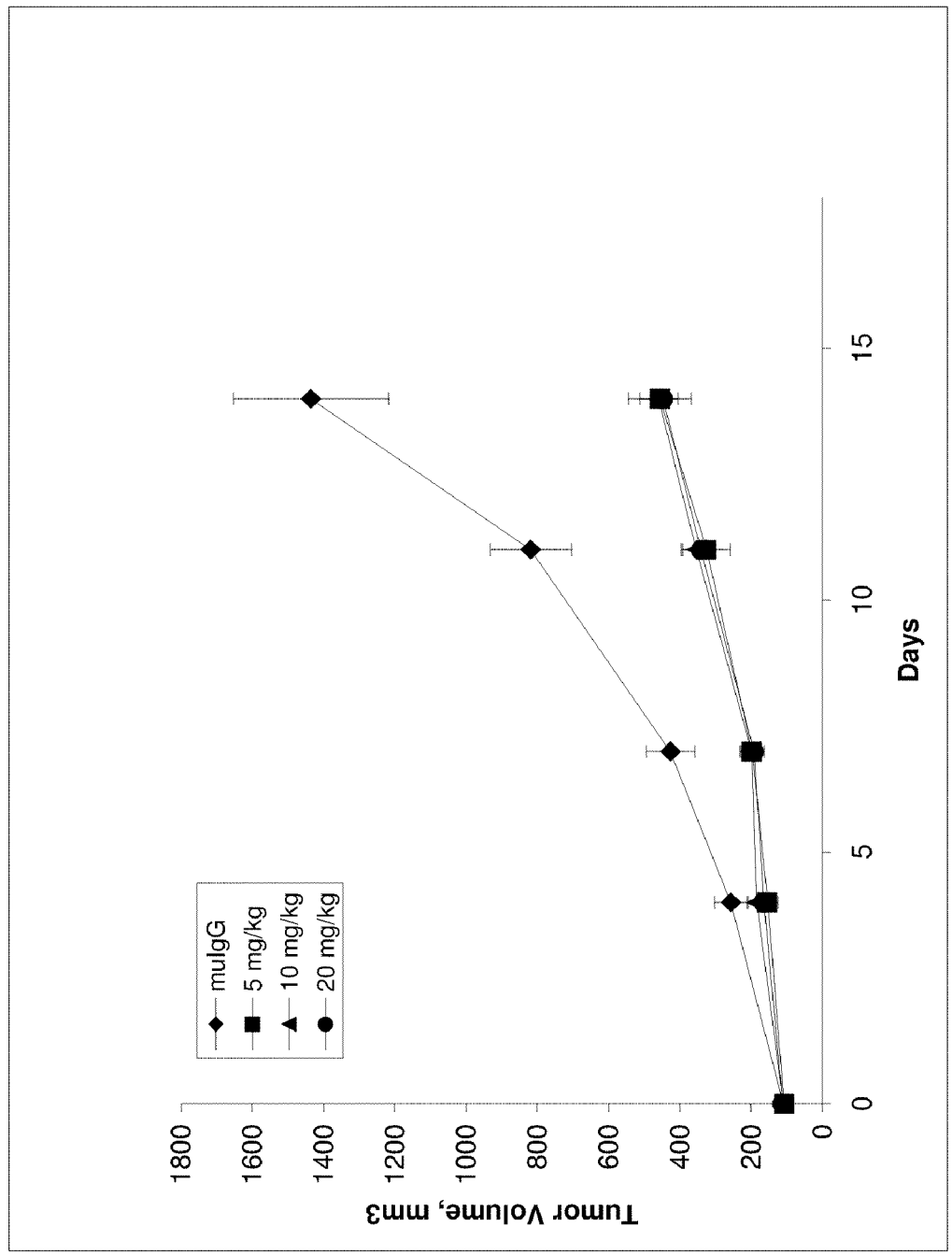
FIG. 9 is a graph summarizing results from an experiment to measure tumor inhibitory activity of a murine IgG control at 20 mg/kg (♦) and anti-FGFR3 antibody 15D8 in a OPM-2 xenograft tumor model (antibody 15D8 at 5 mg/kg (■); antibody 15D8 at 10 mg/kg (▲); and antibody 15D8 at 20 mg/kg (●)).

Each group (10 mice each) received one of the following treatments: murine IgG control at 20 mg/kg, or 15D8 at 5, 10 or 20 mg/kg. Treatment was given intra-peritoneal twice weekly for 2 weeks. Each 15D8 treatment group demonstrated similar tumor growth inhibition of 70% (p<0.001) as shown in FIG. 9. All 15D8 treatments were well-tolerated with no significant body weight loss.

Figure 10:
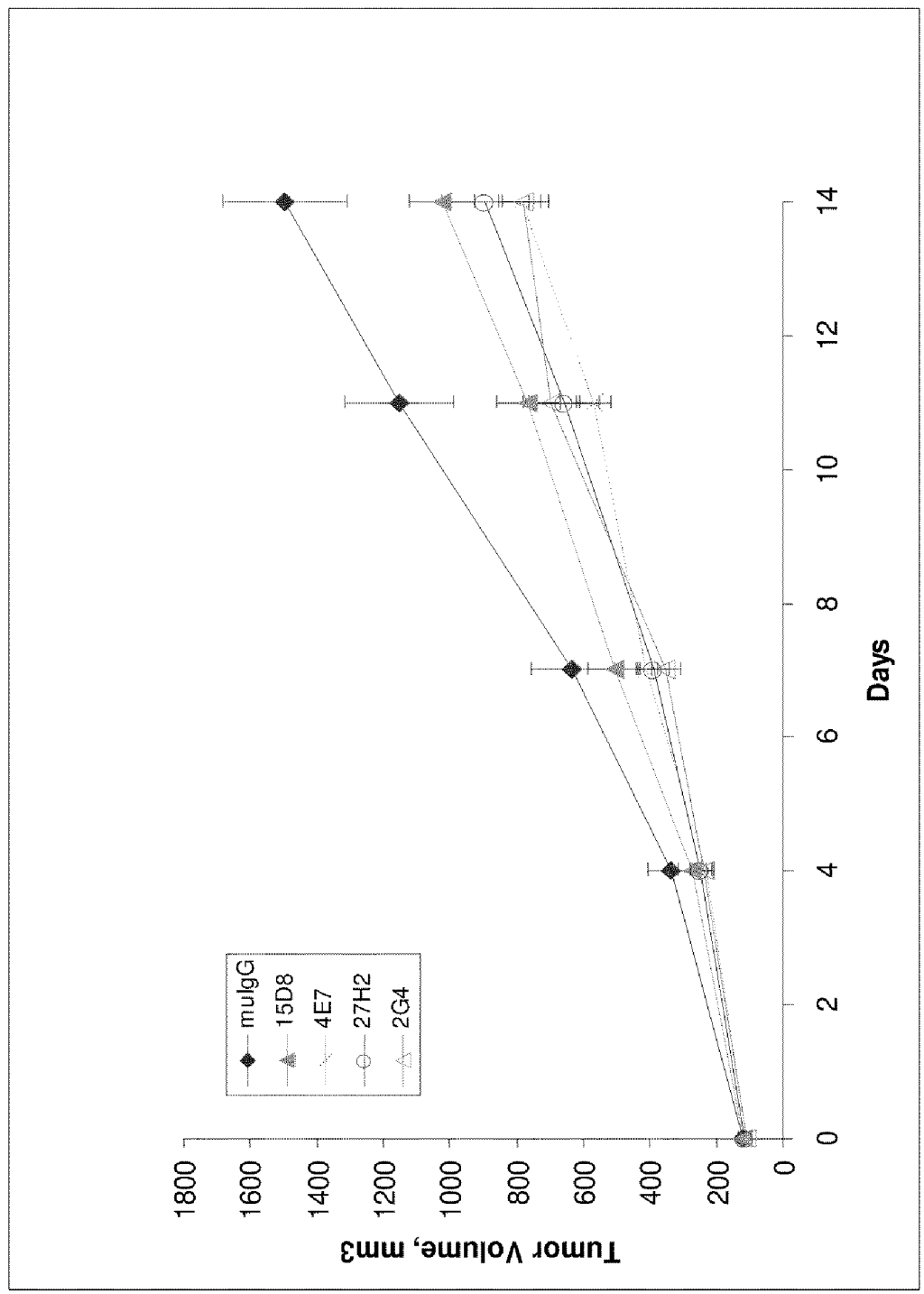
FIG. 10 is a graph summarizing results from an experiment to measure tumor inhibitory activity of a murine IgG control at 1 mg/kg (♦) and anti-FGFR3 antibodies dosed in an OPM-2 xenograft tumor model (murine antibody 15D8 at 1 mg/kg (▲); murine antibody 4E7 at 1 mg/kg (X); murine antibody 27H2 at 1 mg/kg (○); and murine antibody 2G4 at 1 mg/kg (Δ)).

A study was performed to compare four of the murine antibodies. Each group (10 mice each) received one of the following treatments: murine IgG, 15D8, 4E7, 27H2, or 2G4, each dosed at 1 mg/kg. As can be seen in FIG. 10, the four murine antibodies demonstrated similar efficacy at approximately 40% tumor growth inhibition in this model.

Thus, these results demonstrate that treatment with the murine 15D8, 4E7, 27H2, and 2G4 antibodies slows tumor development.

Example 7

Humanization of Anti-FGFR3 Antibodies a. Construction of Humanized and Chimeric Anti-FGFR3 Antibodies This Example describes the humanization of the murine antibody designated 15D8, and the characterization of the resulting humanized antibody. The humanized anti-FGFR3 antibody was designed using the SUPERHUMANIZATION™ method (Arana Therapeutics Ltd. and Hwang, W. Y. et al. (2005) METHODS 36:35-42). Certain framework residues were converted to murine 15D8 residues to improve the antibody's affinity toward FGFR3, and the antibody's activity in inhibiting the biological activity of FGFR3, or both. The designed amino acid sequences were converted to codon-optimized DNA sequences, including (in the following order): 5' HindIII restriction site, Kozak consensus sequence, amino terminal signal sequence, humanized variable region, human IgG1 or Kappa constant region, stop codon, and a 3' EcoRI restriction site.

Chimeric (murine variable region and human constant region) 15D8 heavy (human IgG1) and light (human Kappa) chains were also constructed. The murine variable regions were fused to the human constant region using overlap extension PCR, including (in the following order): 5' HindIII restriction site, Kozak consensus sequence, amino terminal signal sequence, mouse variable region, human IgG1 or Kappa constant region, stop codon, and 3' EcoRI restriction site.

The humanized and chimeric IgG1 heavy chains were subcloned into pEE6.4 (Lonza Biologics) via HindIII and EcoRI sites. The humanized and chimeric Kappa light chains were subcloned into pEE14.4 (Lonza Biologics) via HindIII and EcoRI sites.

Humanized antibody chains or chimeric antibody chains were transiently transfected into 293T cells to produce antibody for purification and subsequent in vitro analysis. Binding of the chimeric and humanized antibodies to human FGFR3 was measured as described below. The results are summarized in Table 9. Additionally, the chimeric and humanized antibodies were tested for inhibition of FGF-stimulated proliferation of FDCP-FGFR3b cells (as described in Example 5). The results are summarized in Table 10.

Each of the possible combinations of immunoglobulin heavy chain and immunoglobulin light chain variable regions are set forth in Table 7A.

TABLE 7A

| Heavy Chain Variable Region | Light Chain Variable Region |
|---|---|
| Chimeric 15D8 (SEQ ID NO: 2) | Chimeric 15D8 (SEQ ID NO: 4) |
| Chimeric 15D8 (SEQ ID NO: 2) | Hu15D8 (SEQ ID NO: 72) |
| Hu15D8 (SEQ ID NO: 70) | Chimeric 15D8 (SEQ ID NO: 4) |
| Hu15D8 (SEQ ID NO: 70) | Hu15D8 (SEQ ID NO: 72) |

Each of the possible combinations of immunoglobulin heavy chains and immunoglobulin light chains are set forth in Table 7B.

TABLE 7B

| Immunoglobulin Heavy Chain | Immunoglobulin Light Chain |
|---|---|
| Chimeric 15D8 (SEQ ID NO: 66) | Chimeric 15D8 (SEQ ID NO: 68) |
| Chimeric 15D8 (SEQ ID NO: 66) | Hu15D8 (SEQ ID NO: 76) |

TABLE 7B-continued

| Immunoglobulin Heavy Chain | Immunoglobulin Light Chain |
|---|---|
| Hu15D8 (SEQ ID NO: 74) | Chimeric 15D8 (SEQ ID NO: 68) |
| Hu15D8 (SEQ ID NO: 74) | Hu15D8 (SEQ ID NO: 76) |

The antibody constructs containing the full length chimeric or humanized immunoglobulin heavy and light chains are designated below:

Chimeric 15D8=Full Length Chimeric 15D8 Heavy Chain (Mouse Variable Region and Human IgG1 Constant Region) (SEQ ID NO: 66) plus Full Length Chimeric 15D8 Light Chain (Mouse Variable Region and Human Kappa Constant Region) (SEQ ID NO: 68)

Humanized 15D8=Full Length Humanized 15D8 Heavy Chain (Humanized Variable Region and Human IgG1 Constant Region) (SEQ ID NO: 74) plus Full Length Humanized 15D8 Light Chain (Humanized Variable Region and Human Kappa Constant Region) (SEQ ID NO: 76)

The nucleic acid sequences encoding and the polypeptide sequences defining the chimeric and humanized antibodies are summarized below (amino terminal signal sequences are not shown). CDR sequences (Kabat definition) are shown in bold/underlined in the amino acid sequences.

```
Nucleic Acid Sequence Encoding the Full Length Chimeric 15D8 Heavy
Chain (Mouse Variable Region and Human IgG1 Constant Region)
                                                        (SEQ ID NO: 65)
   1 gagatccagc tgcagcagtc tggacctgag ctggtgaagc ctggggcttc agtgaaggta 61 tcctgcaagg cttctggtta tgcattcact agctacaaca tgtactgggt gaagcagagc 121 catggaaaga gccttgagtg gattggatat attgatcctt acaatggtgg tactagctac 181 aaccagaagt tcaagggcaa ggccacattg actgttgaca gtcctccag cacagcctac 241 atgcatctca acagcctgac atctgaggac tctgcagtct attactgtgc aagagagggg 301 ggtaactacg aggcctggtt tgcttactgg ggccaaggga ctctggtcac tgtctctgca 361 gcctccacca agggcccatc ggtcttcccc ctggcaccct cctccaagag cacctctggg 421 ggcacagcgg ccctgggctg cctggtcaag gactacttcc ccgaaccggt gacggtgtcg 481 tggaactcag gcgccctgac cagcggcgtg cacaccttcc cggctgtcct acagtcctca 541 ggactctact ccctcagcag cgtggtgacc gtgccctcca gcagcttggg cacccagacc 601 tacatctgca acgtgaatca caagcccagc aacaccaagg tggacaagag agttgagccc 661 aaatcttgtg acaaaactca cacatgccca ccgtgcccag cacctgaact cctgggggga 721 ccgtcagtct tcctcttccc cccaaaaccc aaggacaccc tcatgatctc ccggacccct 781 gaggtcacat gcgtggtggt ggacgtgagc cacgaagacc ctgaggtcaa gttcaactgg 841 tacgtggacg gcgtggaggt gcataatgcc aagacaaagc cgcgggagga gcagtacaac 901 agcacgtacc gtgtggtcag cgtcctcacc gtcctgcacc aggactggct gaatggcaag 961 gagtacaagt gcaaggtctc caacaaagcc ctcccagccc ccatcgagaa gaccatctcc 1021 aaagccaaag gcagccccg agaaccacag gtgtacaccc tgcccccatc ccgggaggag 1081 atgaccaaga accaggtcag cctgacctgc ctggtcaaag gcttctatcc cagcgacatc 1141 gccgtggagt gggagagcaa tgggcagccg gagaacaact acaagaccac gcctcccgtg 1201 ctggactccg acggctcctt cttcctctac agcaagctca ccgtggacaa gagcaggtgg
```

```
1261 cagcagggga acgtcttctc atgctccgtg atgcatgagg ctctgcacaa ccactacacg 1321 cagaagagcc tctccctgtc tccgggtaaa
```

Protein Sequence Defining the Full Length Chimeric 15D8 Heavy Chain
(Mouse Variable Region and Human IgG1 Constant Region)

(SEQ ID NO: 66)
```
  1 eiqlqqsgpe lvkpgasvkv sckasgyaft synmywvkqs hgkslewigy idpynggtsy 61 nqkfkgkatl tvdkssstay mhlnsltsed savyycareg gnyeawfayw gqgtlvtvsa 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvflfppkp kdtlmisrtp evtcvvvdvs hedpevkfnw yvdgvevhna ktkpreeqyn 301 styrvvsvlt vlhqdwlngk eykckvsnka lpapiektis kakgqprepq vytlppsree 361 mtknqvsltc lvkgfypsdi avewesngqp ennykttppv ldsdgsffly skltvdksrw 421 qqgnvfscsv mhealhnhyt qkslslspgk
```

Nucleic Acid Sequence Encoding the Full Length Chimeric 15D8 Light
Chain (Mouse Variable Region and Human Kappa Constant Region)

(SEQ ID NO: 67)
```
  1 caaattgttc tcacccagtc tccagcactc atgtctgcat ctccagggga aaggtcacc 61 atgacctgca gtgccagctc aagtgtaagt tacatgtact ggtaccagca gaagccaaga 121 tcctccccca aaccctggat ttatctcaca tcctacctgg cttctggagt ccctgctcgc 181 ttcagtggca gtggatctgg gacctcttac tctctcacaa tcagcagcat ggaggctgaa 241 gatgctgcca cttattactg ccagcagtgg agtagttacc cgctcacgtt cggtgctgga 301 accaagctgg agctgaaacg aactgtggct gcaccatctg tcttcatctt cccgccatct 361 gatgagcagt tgaaatctgg aactgcctct gttgtgtgcc tgctgaataa cttctatccc 421 agagaggcca aagtacagtg gaaggtggat aacgccctcc aatcgggtaa ctcccaggag 481 agtgtcacag agcaggacag caaggacagc acctacagcc tcagcagcac cctgacgctg 541 agcaaagcag actacgagaa acacaaagtc tacgcctgcg aagtcaccca tcagggcctg 601 agctcgcccg tcacaaagag cttcaacagg ggagagtgt
```

Protein Sequence Defining the Full Length Chimeric 15D8 Light Chain
(Mouse Variable Region and Human Kappa Constant Region)

(SEQ ID NO: 68)
```
  1 qivltqspal msaspgekvt mtcsasssvs ymywyqqkpr sspkpwiylt sylasgvpar 61 fsgsgsgtsy sltissmeae daatyycqqw ssypltfgag tklelkrtva apsvfifpps 121 deqlksgtas vvcllnnfyp reakvqwkvd nalqsgnsqe svteqdskds tyslsstltl 181 skadyekhkv yacevthqgl sspvtksfnr gec
```

Nucleic Acid Sequence Encoding Humanized 15D8 (Hu15D8) Heavy Chain
Variable Region (SEQ ID NO: 69)
```
  1 gaggtccaac tggtgcaatc tggggctgag gtcaagaaac ccggggaatc tctcaaaatt 61 tcatgcaaag gttctggtta cagtttcacc tcatataaca tgtactgggt taggcagatg 121 cctggtaaag gcttggagtg gatggggtac attgatccct ataacggcgg cactagttac 181 aatcagaagt tcaagggcaa ggccacattg actgttgaca gtccatctc aactgcttac 241 ctgcaatggt cctctctcaa agccagcgac actgctatgt actactgcgc aagggaggga 301 ggcaattacg aggcttggtt cgcttattgg ggacaaggca ctcttgtcac cgtctcctca
```

Protein Sequence Defining Humanized 15D8 (Hu15D8) Heavy Chain
Variable Region (SEQ ID NO: 70)
```
  1 evqlvqsgae vkkpgeslki sckgsgysft synmywvrqm pgkglewmgy idpynggtsy 61 nqkfkgkatl tvdksistay lqwsslkasd tamyycareg gnyeawfayw gqgtlvtvss
```

Nucleic Acid Sequence Encoding Humanized 15D8 (Hu15D8) Light Chain
Variable Region
(SEQ ID NO: 71)

```
  1 gatatccaac tcacccagtc cccttcatcc ctgtctgcat cagtcgggga cagagtgaca 61 attacttgtt ccgccagctc tagtgtctca tacatgtatt ggtttcagca aaagccagga 121 aaagctccca aaccctgat ctatctgacc agctatctgg caagcggcgt gccttctcgg 181 ttcagtggat cagggtccgg tacagacttt accctgacta ttagcagtct gcaaccagag 241 gacttcgcca cttattactg ccaacagtgg agttcatatc ccctgacttt tggcggaggg 301 accaaggtcg agatcaag
```

Protein Sequence Defining Humanized 15D8 (Hu15D8) Light Chain
Variable Region
(SEQ ID NO: 72)

```
  1 diqltqspss lsasvgdrvt itcsasssvs ymywfqqkpg kapkpliylt sylasgvpsr 61 fsgsgsgtdf tltisslqpe dfatyycqqw ssypltfggg tkveik
```

Nucleic Acid Sequence Defining the Full Length Humanized 15D8
(Hu15D8) Heavy Chain (Humanized Variable Region and Human IgG1
Constant Region)
(SEQ ID NO: 73)

```
  1 gaggtccaac tggtgcaatc tggggctgag gtcaagaaac cgggggaatc tctcaaaatt 61 tcatgcaaag gttctggtta cagtttcacc tcatataaca tgtactgggt taggcagatg 121 cctggtaaag gcttggagtg gatggggtac attgatccct ataacggcgg cactagttac 181 aatcagaagt tcaagggcaa ggccacattg actgttgaca agtccatctc aactgcttac 241 ctgcaatggt cctctctcaa agccagcgac actgctatgt actactgcgc aagggaggga 301 ggcaattacg aggcttggtt cgcttattgg ggacaaggca ctcttgtcac cgtctcctca 361 gcctcaacaa aaggaccaag tgtgttccca ctcgccccta gcagcaagag tacatccggg 421 ggcactgcag cactcggctg cctcgtcaag gattattttc cagagccagt aaccgtgagc 481 tggaacagtg gagcactcac ttctggtgtc cactttttc ctgctgtcct gcaaagctct 541 ggcctgtact cactcagctc cgtcgtgacc gtgccatctt catctctggg cactcagacc 601 tacatctgta atgtaaacca caagcctagc aatactaagg tcgataagcg ggtggaaccc 661 aagagctgcg acaagactca cacttgtccc ccatgccctg cccctgaact tctgggcggt 721 cccagcgtct ttttgttccc accaaagcct aaagatactc tgatgataag tagaacaccc 781 gaggtgacat gtgttgttgt agacgtttcc cacgaggacc cagaggttaa gttcaactgg 841 tacgttgatg gagtcgaagt acataatgct aagaccaagc ctagagagga gcagtataat 901 agtacatacc gtgtagtcag tgttctcaca gtgctgcacc aagactggct caacggcaaa 961 gaatacaaat gcaaagtgtc caacaaagca ctcccagccc ctatcgagaa gactattagt 1021 aaggcaaagg gcagcctcg tgaaccacag gtgtacactc tgccacccag tagagaggaa 1081 atgacaaaga ccaagtctct attgacctgc ctggtgaaag gcttctaccc cagcgacatc 1141 gccgttgagt gggagagtaa cggtcagcct gagaacaatt acaagacaac ccccccagtg 1201 ctggatagtg acgggtcttt ctttctgtac agtaagctga ctgtggacaa gtcccgctgg 1261 cagcagggta acgtcttcag ctgttccgtg atgcacgagg cattgcacaa ccactacacc 1321 cagaagtcac tgagcctgag cccagggaag
```

Protein Sequence Defining the Full Length Humanized 15D8 (Hu15D8)
Heavy Chain (Humanized Variable Region and Human IgG1 Constant
Region)
(SEQ ID NO: 74)

```
  1 evqlvqsgae vkkpgeslki sckgsgysft synmywvrqm pgkglewmgy idpynggtsy

61 nqkfkgkatl tvdksistay lqwsslkasd tamyycareg gnyeawfayw gqgtlvtvss
```

```
121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvflfppkp kdtlmisrtp evtcvvvdvs hedpevkfnw yvdgvevhna ktkpreeqyn 301 styrvvsvlt vlhqdwlngk eykckvsnka lpapiektis kakgqprepq vytlppsree 361 mtknqvsltc lvkgfypsdi avewesngqp ennykttppv ldsdgsffly skltvdksrw 421 qqgnvfscsv mhealhnhyt qkslslspgk
```

Nucleic Acid Sequence Encoding the Full Length Humanized 15D8 (Hu15D8) Light Chain (Humanized Variable Region and Human Kappa Constant Region)

(SEQ ID NO: 75)
```
  1 gatatccaac tcacccagtc cccttcatcc ctgtctgcat cagtcgggga cagagtgaca 61 attacttgtt ccgccagctc tagtgtctca tacatgtatt ggtttcagca aaagccagga 121 aaagctccca accccctgat ctatctgacc agctatctgg caagcggcgt gccttctcgg 181 ttcagtggat cagggtccgg tacagacttt accctgacta ttagcagtct gcaaccagag 241 gacttcgcca cttattactg caacagtgg agttcatatc cctgactttt ggcggaggg 301 accaaggtcg agatcaagcg cacagtcgcc gctccctccg tgttcatctt tccaccaagt 361 gatgagcaac tgaagtctgg tactgcttca gtcgtgtgtc tgctgaacaa tttctacccct 421 cgagaagcca agtccaatg gaaggtagac aacgcactgc agtccggcaa tagccaagaa 481 tcagttaccg aacaggattc aaaggacagt acatattccc tgagcagcac tctgaccctg 541 tcaaaggccg attacgagaa acacaaggtc tatgcttgcg aagtgacaca tcagggactg 601 tccagcccag tgacaaaatc ttttaaccgt ggggagtgt
```

Protein Sequence Defining the Full Length Humanized 15D8 (Hu15D8) Light Chain (Humanized Variable Region and Human Kappa Constant Region)

(SEQ ID NO: 76)
```
  1 diqltqspss lsasvgdrvt itcsasssvs ymywfqqkpg kapkpliylt sylasgvpsr 61 fsgsgsgtdf tltisslqpe dfatyycqqw ssypltfggg tkveikrtva apsvfifpps 121 deqlksgtas vvcllnnfyp reakvqwkvd nalqsgnsqe svteqdskds tyslsstltl 181 skadyekhkv yacevthqgl sspvtksfnr gec
```

Nucleic Acid Sequence Encoding Human IgG1 Heavy Chain Constant Region (SEQ ID NO: 77)
```
  1 gcctccacca agggcccatc ggtcttcccc ctggcaccct cctccaagag cacctctggg 61 ggcacagcgg ccctgggctg cctggtcaag gactacttcc ccgaaccggt gacggtgtcg 121 tggaactcag cgccctgac cagcggcgtg cacaccttcc cggctgtcct acagtcctca 181 ggactctact ccctcagcag cgtggtgacc gtgccctcca gcagcttggg cacccagacc 241 tacatctgca acgtgaatca caagcccagc aacaccaagg tggacaagag agttgagccc 301 aaatcttgtg acaaaactca cacatgccca ccgtgcccag cacctgaact cctggggga 361 ccgtcagtct tcctcttccc cccaaaaccc aaggacaccc tcatgatctc ccggacccct 421 gaggtcacat gcgtggtggt ggacgtgagc cacgaagacc ctgaggtcaa gttcaactgg 481 tacgtggacg gcgtggaggt gcataatgcc aagacaaagc cgcgggagga gcagtacaac 541 agcacgtacc gtgtggtcag cgtcctcacc gtcctgcacc aggactggct gaatggcaag 601 gagtacaagt gcaaggtctc caacaaagcc ctcccagccc ccatcgagaa gaccatctcc 661 aaagccaaag ggcagccccg agaaccacag gtgtacaccc tgcccccatc ccgggaggag 721 atgaccaaga accaggtcag cctgacctgc ctggtcaaag gcttctatcc cagcgacatc 781 gccgtggagt gggagagcaa tgggcagccg gagaacaact acaagaccac gcctcccgtg
```

-continued

```
841 ctggactccg acggctcctt cttcctctac agcaagctca ccgtggacaa gagcaggtgg 901 cagcagggga acgtcttctc atgctccgtg atgcatgagg ctctgcacaa ccactacacg 961 cagaagagcc tctccctgtc tccgggtaaa
```

Protein Sequence Defining Human IgG1 Heavy Chain Constant Region
(SEQ ID NO: 78)

```
  1 astkgpsvfp lapsskstsg gtaalgclvk dyfpepvtvs wnsgaltsgv htfpavlqss 61 glyslssvvt vpssslgtqt yicnvnhkps ntkvdkrvep kscdkthtcp pcpapellgg 121 psvflfppkp kdtlmisrtp evtcvvvdvs hedpevkfnw yvdgvevhna ktkpreeqyn 181 styrvvsvlt vlhqdwlngk eykckvsnka lpapiektis kakgqprepq vytlppsree 241 mtknqvsltc lvkgfypsdi avewesngqp ennykttppv ldsdgsffly skltvdksrw 301 qqgnvfscsv mhealhnhyt qkslslspgk
```

Nucleic Acid Sequence Encoding Human Kappa Chain Constant Region
(SEQ ID NO: 79)

```
  1 cgaactgtgg ctgcaccatc tgtcttcatc ttcccgccat ctgatgagca gttgaaatct 61 ggaactgcct ctgttgtgtg cctgctgaat aacttctatc ccagagaggc caaagtacag 121 tggaaggtgg ataacgccct ccaatcgggt aactcccagg agagtgtcac agagcaggac 181 agcaaggaca gcacctacag cctcagcagc accctgacgc tgagcaaagc agactacgag 241 aaacacaaag tctacgcctg cgaagtcacc catcagggcc tgagctcgcc cgtcacaaag 301 agcttcaaca ggggagagtg t
```

Protein Sequence Defining Human Kappa Chain Constant Region
(SEQ ID NO: 80)

```
  1 rtvaapsvfi fppsdeqlks gtasvvcllnn fypreakvq wkvdnalqsg nsqesvteqd 61 skdstyslss tltlskadye khkvyacevt hqglsspvtk sfnrgec
```

For convenience, Table 8 provides a concordance chart showing the SEQ ID NO. of each sequence discussed in this Example.

TABLE 8

| SEQ. ID NO. | Protein or Nucleic Acid |
|---|---|
| 65 | Chimeric 15D8 Mouse Heavy Chain Variable + Human IgG1 constant-nucleic acid |
| 66 | Chimeric 15D8 Mouse Heavy Chain Variable + Human IgG1 constant-protein |
| 67 | Chimeric 15D8 Mouse Light Chain Variable + Human Kappa constant-nucleic acid |
| 68 | Chimeric 15D8 Mouse Light Chain + Human Kappa constant-protein |
| 69 | Humanized 15D8 Heavy Chain Variable Region-nucleic acid |
| 70 | Humanized 15D8 Heavy Chain Variable Region-protein |
| 71 | Humanized 15D8 Light Chain Variable Region-nucleic acid |
| 72 | Humanized 15D8 Light Chain Variable Region-protein |
| 73 | Humanized 15D8 Heavy Human Variable + Human IgG1 constant-nucleic acid |
| 74 | Humanized 15D8 Heavy Human Variable + Human IgG1 constant-protein |
| 75 | Humanized 15D8 Human Variable + Human Kappa constant-nucleic acid |
| 76 | Humanized 15D8 Human Variable + Human Kappa constant-protein |
| 77 | Human IgG1 constant-nucleic acid |
| 78 | Human IgG1 constant-protein |
| 79 | Human Kappa constant-nucleic acid |
| 80 | Human Kappa constant-protein | b. Binding Affinities of Humanized and Chimeric Anti-FGFR3 Monoclonal Antibodies The binding affinities of monoclonal 15D8, chimeric 15D8, and humanized 15D8 antibodies for recombinant human FGFR3 IIIc Fc fusion protein was measured using a kinetic exclusion assay, KinExA® technology (Sapidyne Instruments, Inc.). First, beads were prepared for the purpose of detecting anti-FGFR3 antibody that is unbound to FGFR3 IIIc Fc. This was done by adding 1 ml recombinant human FGFR3IIIc Fc (R&D Systems, Inc.) 10 ug/ml in PBS to 200 mg polymethyl methacrylate (PMMA) hard beads. The suspension was mixed and rotated for two hours at room temperature. Next, the mixture was centrifuged and supernatant was discarded. The bead pellet was rinsed once with 1 ml BSA 10 mg/ml in PBS by incubation for 1 hour at room temperature with rotation. The beads were resuspended in 27 ml PBS with 0.02% NaN$_3$. Next, a fixed concentration of anti-FGFR3 antibody (0.5 nM) was incubated in solution with a series of FGFR3 IIIc Fc concentrations (started with 50 nM (in PBS BSA (1 mg/ml) and serially diluted 1:2 in PBS BSA(1 mg/ml)) to obtain 50 to 0.0122 nM FGFR3 III Fc) at room temperature for at least 4 hours to allow equilibrium to be reached. By measuring the amount of anti-FGFR3 antibody that is not bound to FGFR3 IIIc Fc, the KD was determined. Unbound anti-FGFR3 antibody was detected by allowing the anti-FGFR3 antibody/FGFR3 IIIc Fc solution to flow through the FGFR3 IIIc Fc PMMA beads. The anti-FGFR3 antibody captured by these beads was then detected with Cy5-conjugated anti-human secondary antibody 0.3 ug/ml (Jackson ImmunoResearch) or Cy5-conjugated anti-mouse secondary antibody (Jackson ImmunoResearch) 0.5 ug/ml in PBS BSA 1 mg/ml. The detected signal for captured anti-FGFR3 antibody is directly proportional to the remaining free binding sites, thus allowing KD determination. The experiments were repeated, varying the concentrations of anti-FGFR3 antibody or FGFR3 III Fc used in solution, and the KD was calculated with the KinExA® software using n-curve analysis. The resulting data are shown in Table 9. These data demonstrated that 15D8, chimeric 15D8, and humanized 15D8 strongly bind FGFR3 with nearly equal affinity.

TABLE 9

| | | 95% Confidence Interval | | |
|---|---|---|---|---|
| | KD (M) | KD High (M) | KD Low (M) | n |
| 15D8 | 8.06E−11 | 1.54E−10 | 3.09E−11 | 3 |
| Chimeric 15D8 | 5.03E−11 | 7.36E−11 | 3.13E−11 | 2 |
| Humanized 15D8 | 7.72E−11 | 1.79E−10 | 1.71E−11 | 3 | c. Antiproliferative Activity of Humanized and Chimeric Anti-FGFR3 Monoclonal Antibodies The chimeric and humanized 15D8 antibodies were tested for inhibition of FGF1-induced proliferation of FDCP-FGFR3 IIIb #122, as described in Example 5. Inhibition data are summarized in Table 10.

TABLE 10

| | FDCP FGFR3 IIIb Proliferation $IC_{50}$ | | |
|---|---|---|---|
| Antibody | Average $IC_{50}$ (nM) | Standard Deviation (nM) | n |
| Chimeric 15D8 | 1.47 | 0.97 | 7 |
| Humanized 15D8 | 3.73 | 2.56 | 3 |

The results in Table 10 demonstrate that chimeric 15D8 and humanized 15D8 strongly inhibited FGF1-induced proliferation in FDCP-FGFR3 IIIb cells with nearly equal potency.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

We claim:

1. An isolated binding protein that binds human fibroblast growth factor receptor 3 (FGFR3) comprising an immunoglobulin heavy chain variable region and an immunoglobulin light chain variable region selected from the group consisting of:

(a) (i) an immunoglobulin heavy chain variable region comprising a $CDR_{H1}$ comprising the sequence SEQ ID NO: 17 (15D8), a $CDR_{Hb}$ comprising an amino acid sequence selected from the group consisting of SEQ ID NO: 18 (15D8), and a $CDR_{H3}$ comprising the sequence SEQ ID NO: 19 (15D8); and (ii) an immunoglobulin light chain variable region comprising a $CDR_{L1}$ comprising the sequence SEQ ID NO: 22 (15D8), a $CDR_{L2}$ comprising the sequence SEQ ID NO: 23 (15D8), and a $CDR_{L3}$ comprising the sequence SEQ ID NO: 24 (15D8);

(b) (i) an immunoglobulin heavy chain variable region comprising a $CDR_{H1}$ comprising the sequence SEQ ID NO: 17 (27H2, 4E7(7D12)), a $CDR_{H2}$ comprising an amino acid sequence selected from the group consisting of SEQ ID NO: 25 (27H2, 4E7(7D12)), and a $CDR_{H3}$ comprising the sequence SEQ ID NO: 19 (27H2, 4E7 (7D12)); and
- (ii) an immunoglobulin light chain variable region comprising a $CDR_{L1}$ comprising the sequence SEQ ID NO: 22 (27H2, 4E7(7D12)), a $CDR_{L2}$ comprising an amino acid sequence selected from the group consisting of SEQ ID NO: 26 (27H2, 4E7(7D12)), and a $CDR_{L3}$ comprising the sequence SEQ ID NO: 27 (27H2, 4E7(7D12));
- (c) (i) an immunoglobulin heavy chain variable region comprising a $CDR_{H1}$ comprising the sequence SEQ ID NO: 17 (2G4), a $CDR_{H2}$ comprising the sequence SEQ ID NO: 28 (2G4), and a $CDR_{H3}$ comprising the sequence SEQ ID NO: 19 (2G4); and
- (ii) an immunoglobulin light chain variable region comprising a $CDR_{L1}$ comprising the sequence SEQ ID NO: 22 (2G4), a $CDR_{L2}$ comprising the sequence SEQ ID NO: 26 (2G4), and a $CDR_{L3}$ comprising the sequence SEQ ID NO: 27 (2G4); and
- (d) (i) an immunoglobulin heavy chain variable region comprising a $CDR_{H1}$ comprising the sequence SEQ ID NO: 29 (20B4), a $CDR_{H2}$ comprising the sequence SEQ ID NO: 18 (20B4), and a $CDR_{H3}$ comprising the sequence SEQ ID NO: 30 (20B4); and
- (ii) an immunoglobulin light chain variable region comprising a $CDR_{L1}$ comprising the sequence SEQ ID NO: 31 (20B4), a $CDR_{L2}$ comprising the sequence SEQ ID NO: 32 (20B4), and a $CDR_{L3}$ comprising the sequence SEQ ID NO: 33 (20B4).

2. The binding protein of claim 1, wherein the CDR sequences are interposed between human and humanized framework sequences.

3. The binding protein of claim 1, wherein the binding protein is a monoclonal antibody or antigen binding protein fragment thereof.

4. An isolated binding protein that binds human fibroblast growth factor receptor 3 (FGFR3) comprising an immunoglobulin heavy chain variable region and an immunoglobulin light chain variable region selected from the group consisting of:
- (a) an immunoglobulin heavy chain variable region comprising the amino acid sequence of SEQ ID NO: 2 (15D8), and
    an immunoglobulin light chain variable region comprising the amino acid sequence of SEQ ID NO: 4 (15D8);
- (b) an immunoglobulin heavy chain variable region comprising the amino acid sequence of SEQ ID NO: 6 (27H2), and
    an immunoglobulin light chain variable region comprising the amino acid sequence of SEQ ID NO: 8 (27H2);
- (c) an immunoglobulin heavy chain variable region comprising the amino acid sequence of SEQ ID NO: 10 (2G4), and
    an immunoglobulin light chain variable region comprising the amino acid sequence of SEQ ID NO: 8 (2G4);
- (d) an immunoglobulin heavy chain variable region comprising the amino acid sequence of SEQ ID NO: 12 (4E7(7D12)), and
    an immunoglobulin light chain variable region comprising the amino acid sequence of SEQ ID NO: 8 (4E7 (7D12));
- (e) an immunoglobulin heavy chain variable region comprising the amino acid sequence of SEQ ID NO: 14 (20B4), and
    an immunoglobulin light chain variable region comprising the amino acid sequence of SEQ ID NO: 16 (20B4); and
- (f) an immunoglobulin heavy chain variable region comprising the amino acid sequence of SEQ ID NO: 70 (Hu15D8), and
    an immunoglobulin light chain variable region comprising the amino acid sequence of SEQ ID NO: 72 (Hu15D8).

5. The binding protein of claim 4, wherein the immunoglobulin heavy chain variable region comprises the amino acid sequence of SEQ ID NO: 2 (15D8), and the immunoglobulin light chain variable region comprises the amino acid sequence of SEQ ID NO: 4 (15D8).

6. The binding protein of claim 4, wherein the immunoglobulin heavy chain variable region comprises the amino acid sequence of SEQ ID NO: 70 (Hu15D8), and the immunoglobulin light chain variable region comprises the amino acid sequence of SEQ ID NO: 72 (Hu15D8).

7. An isolated binding protein that binds human fibroblast growth factor receptor 3 (FGFR3) comprising an immunoglobulin heavy chain and an immunoglobulin light chain selected from the group consisting of:
- (a) an immunoglobulin heavy chain of SEQ ID NO: 39 (15D8), and an immunoglobulin light chain of SEQ ID NO: 41 (15D8);
- (b) an immunoglobulin heavy chain of SEQ ID NO: 43 (27H2), and an immunoglobulin light chain of SEQ ID NO: 45 (27H2);
- (c) an immunoglobulin heavy chain of SEQ ID NO: 47 (2G4), and an immunoglobulin light chain of SEQ ID NO: 49 (2G4);
- (d) an immunoglobulin heavy chain of SEQ ID NO: 51 (4E7(7D12)), and an immunoglobulin light chain of SEQ ID NO: 53 (4E7(7D12));
- (e) an immunoglobulin heavy chain of SEQ ID NO: 55 (20B4), and an immunoglobulin light chain of SEQ ID NO: 57 (20B4);
- (f) an immunoglobulin heavy chain of SEQ ID NO: 66 (Chimeric 15D8), and an immunoglobulin light chain of SEQ ID NO: 68 (Chimeric 15D8); and
- (g) an immunoglobulin heavy chain of SEQ ID NO: 74 (Hu15D8), and an immunoglobulin light chain of SEQ ID NO: 76 (Hu15D8).

8. The binding protein of claim 7, wherein the immunoglobulin heavy chain comprises the amino acid sequence of SEQ ID NO: 39 (15D8), and the immunoglobulin light chain comprises the amino acid sequence of SEQ ID NO: 41 (15D8).

9. The binding protein of claim 7, wherein the immunoglobulin heavy chain comprises the amino acid sequence of SEQ ID NO: 66 (Chimeric 15D8), and the immunoglobulin light chain comprises the amino acid sequence of SEQ ID NO: 68 (Chimeric 15D8).

10. The binding protein of claim 7, wherein the immunoglobulin heavy chain comprises the amino acid sequence of SEQ ID NO: 74 (Hu15D8), and the immunoglobulin light chain comprises the amino acid sequence of SEQ ID NO: 76 (Hu15D8).

11. The binding protein of claim 4 or 7, wherein the binding protein is a monoclonal antibody or an antigen binding fragment thereof.

* * * * *